United States Patent
Spodsberg et al.

(10) Patent No.: US 10,336,993 B2
(45) Date of Patent: Jul. 2, 2019

(54) POLYPEPTIDES HAVING CELLULOLYTIC ENHANCING ACTIVITY AND POLYNUCLEOTIDES ENCODING SAME

(71) Applicants: Novozymes A/S, Bagsvaerd (DK); Novozymes, Inc., Davis, CA (US)

(72) Inventors: Nikolaj Spodsberg, Bagsvaerd (DK); Tarana Shaghasi, Davis, CA (US); Matt Sweeney, Davis, CA (US); Feng Xu, Davis, CA (US); Kirk Schnorr, Bagsvaerd (DK)

(73) Assignees: Novozymes A/S, Bagsvaerd (DK); Novozymes, Inc., Davis, CA (US)

( * ) Notice: Subject to any disclaimer, the term of this patent is extended or adjusted under 35 U.S.C. 154(b) by 0 days.

(21) Appl. No.: 16/123,482

(22) Filed: Sep. 6, 2018

(65) Prior Publication Data

US 2019/0002858 A1    Jan. 3, 2019

Related U.S. Application Data

(62) Division of application No. 14/437,472, filed as application No. PCT/US2013/065485 on Oct. 17, 2013, now abandoned.

(60) Provisional application No. 61/717,989, filed on Oct. 24, 2012, provisional application No. 61/717,999, filed on Oct. 24, 2012.

(51) Int. Cl.
| | | |
|---|---|---|
| *C12N 9/24* | (2006.01) | |
| *C12N 9/42* | (2006.01) | |
| *C12P 19/02* | (2006.01) | |
| *C12P 19/14* | (2006.01) | |

(52) U.S. Cl.
CPC ............ *C12N 9/2437* (2013.01); *C12P 19/02* (2013.01); *C12P 19/14* (2013.01); *Y02E 50/16* (2013.01)

(58) Field of Classification Search
None
See application file for complete search history.

(56) References Cited

FOREIGN PATENT DOCUMENTS

| | | |
|---|---|---|
| WO | 2005074647 A2 | 8/2005 |
| WO | 2005074656 A2 | 8/2005 |
| WO | 2007089290 A2 | 8/2007 |
| WO | 2008148131 A1 | 12/2008 |
| WO | 2008151043 A1 | 12/2008 |
| WO | 2009085859 A2 | 7/2009 |
| WO | 2009085864 A2 | 7/2009 |
| WO | 2009085868 A1 | 7/2009 |
| WO | 2009085935 A2 | 7/2009 |
| WO | 2010065830 A1 | 6/2010 |
| WO | 2010138754 A1 | 12/2010 |
| WO | 2011005867 A1 | 1/2011 |
| WO | 2011035027 A2 | 3/2011 |
| WO | 2011039319 A1 | 4/2011 |
| WO | 2011041397 A1 | 4/2011 |
| WO | 2011041504 A1 | 4/2011 |
| WO | 2012030799 A1 | 3/2012 |
| WO | 2012061517 A1 | 5/2012 |
| WO | 2012101206 A2 | 8/2012 |
| WO | 2012113340 A1 | 8/2012 |
| WO | 2012122477 A1 | 9/2012 |
| WO | 2012122518 A1 | 9/2012 |
| WO | 2012135659 A2 | 10/2012 |
| WO | 2012146171 A1 | 11/2012 |
| WO | 2012149344 A1 | 11/2012 |
| WO | 2013043910 A1 | 3/2013 |
| WO | 2012021394 A1 | 8/2013 |

OTHER PUBLICATIONS

Harris et al 2010 (Biochemistry 49: p. 3305-3316).*
Stajich et al, 2010, PNAS 107 (26) , 11889-11894.
Tajich et al, 2010, Uniport Access No. A8NUU4.
Harris et al, 2010, Biochem 49 (15), 3305-3316.
Wang et al, 2009, Microbiological Research 166, 650-657.

* cited by examiner

*Primary Examiner* — Matthew R Keogh
(74) *Attorney, Agent, or Firm* — Robert Starnes

(57) ABSTRACT

The present invention relates to isolated polypeptides having cellulolytic enhancing activity, catalytic domains, cellulose binding domains and polynucleotides encoding the polypeptides, catalytic domains or cellulose binding domains. The invention also relates to nucleic acid constructs, vectors, and host cells comprising the polynucleotides as well as methods of producing and using the polypeptides, catalytic domains or cellulose binding domains.

21 Claims, 7 Drawing Sheets

Specification includes a Sequence Listing.

SEQUENCE LISTING

<160> NUMBER OF SEQ ID NOS: 32

<210> SEQ ID NO 1
<211> LENGTH: 1461
<212> TYPE: DNA
<213> ORGANISM: Lentinus similis

<400> SEQUENCE: 1

```
atgcgcggat tcgcttctct catcgcgttt gcctctctgg caacatctgc ttttgctcat    60
```

-continued

```
tctatcttcc aggttcgtgt ttccgcgtat tggtgaacat accataacgg cagactttgg    120
catgcttata ggaagtctac atcaacggtg ttgatcaagg ccacatcaac ggtatccgtg    180
tacccgacta cgatggtgta cgtatacctt gacacctgct gtaactgaat aaactaacgt    240
caacttcatc aagccaatca ccgacgtaac ttccaacgat gttatttgca atggcggtat    300 caaccccta caccagccca tctcaaaaac ggttctacag gctcccgctg agctcaaat     360 cactacggaa tggcaccaca gtaagtcgtt atccctgaat tcttgtaat gaatagtatc    420 actgattgtc tttcagctct caatggtgcc gaccccctg acccggccga cccaatcgac    480
gctagtcaca agggccccgt gctcacgtat ctcgcgaaga tacccgatgc gactcagagc    540
actgtaactg gtcttaaatg gttcaagatt tacgaggatg gcctggactc tagcggaaag    600
tggggcgttg accgtatgat cgcaaacaag ggcaaggtca ccttcaattt gccaagctgc    660
attgaacctg ccaatacct ccttcgtcac gaactcattg gtgagtatac tgagggatgt    720
gagagtggag ttgctaactg cattttctta agccctacat gccgcatcca gctacccggg    780
tgctcaactc tacgtatgaa cagcctgggt ttccatgaca ttcgctctgc taactgatat    840
gctacagatg gagtgtgcgc agctcaacat cactggtggc ggtaacactc aacccgcgac    900
ggtcagcttc cctggtgcat acagcggtaa gaaaataacg cagatgcccg aagtgcgagt    960
tgacggctca ccgtgttctc aaggtaccga cccaggtatc aaaatcaaca tctatcaacc   1020
actctcgagc tacaccatcc ccggtgagct tctctttgac aaccacaatt agatgtgact   1080
aattgattac tctcaggtcc ccccgttttc acttgcgatg gctctccaac ttcgccatct   1140
cagccaacct ctcctgcatc cactcccaca catcccaata cgacgacgcc tccttctact   1200
cccccacccg cgcaaacttc gaccgcaaca gcagctcact acgccaatg cggtggtata   1260 gggtatgttc ttcgcctttt tcggtatcga ccgtgtgttg ttgtacttac accttttctc   1320
ccagttacac cggacccacc gtctgcgcgt ccccgtacac ctgcgtgaag tccagcgact   1380
acgtaagtct atcagccatc gaccctgcat tcatctgctg accagaagct tctgggtata   1440
cagtacagcc agtgtctatg a                                             1461
```

<210> SEQ ID NO 2
<211> LENGTH: 316
<212> TYPE: PRT
<213> ORGANISM: Lentinus similis

<400> SEQUENCE: 2

```
Met Arg Gly Phe Ala Ser Leu Ile Ala Phe Ala Ser Leu Ala Thr Ser
1               5                   10                  15

Ala Phe Ala His Ser Ile Phe Gln Glu Val Tyr Ile Asn Gly Val Asp
                20                  25                  30

Gln Gly His Ile Asn Gly Ile Arg Val Pro Asp Tyr Asp Gly Pro Ile
            35                  40                  45

Thr Asp Val Thr Ser Asn Asp Val Ile Cys Asn Gly Gly Ile Asn Pro
        50                  55                  60

Tyr His Gln Pro Ile Ser Lys Thr Val Leu Gln Ala Pro Ala Gly Ala
65                  70                  75                  80

Gln Ile Thr Thr Glu Trp His His Thr Leu Asn Gly Ala Asp Pro Ser
                85                  90                  95

Asp Pro Ala Asp Pro Ile Asp Ala Ser His Lys Gly Pro Val Leu Thr
            100                 105                 110

Tyr Leu Ala Lys Ile Pro Asp Ala Thr Gln Ser Thr Val Thr Gly Leu
```

|     | 115 |     |     | 120 |     |     |     | 125 |     |     |     |
| --- | --- | --- | --- | --- | --- | --- | --- | --- | --- | --- | --- |

Lys Trp Phe Lys Ile Tyr Glu Asp Gly Leu Asp Ser Ser Gly Lys Trp
130                 135                 140

Gly Val Asp Arg Met Ile Ala Asn Lys Gly Lys Val Thr Phe Asn Leu
145                 150                 155                 160

Pro Ser Cys Ile Glu Pro Gly Gln Tyr Leu Leu Arg His Glu Leu Ile
                165                 170                 175

Ala Leu His Ala Ala Ser Ser Tyr Pro Gly Ala Gln Leu Tyr Met Glu
                180                 185                 190

Cys Ala Gln Leu Asn Ile Thr Gly Gly Gly Asn Thr Gln Pro Ala Thr
                195                 200                 205

Val Ser Phe Pro Gly Ala Tyr Ser Gly Thr Asp Pro Gly Ile Lys Ile
210                 215                 220

Asn Ile Tyr Gln Pro Leu Ser Ser Tyr Thr Ile Pro Gly Pro Pro Val
225                 230                 235                 240

Phe Thr Cys Asp Gly Ser Pro Thr Ser Pro Ser Gln Pro Thr Ser Pro
                245                 250                 255

Ala Ser Thr Pro Thr His Pro Asn Thr Thr Thr Pro Pro Ser Thr Pro
                260                 265                 270

Pro Pro Ala Gln Thr Ser Thr Ala Thr Ala Ala His Tyr Ala Gln Cys
                275                 280                 285

Gly Gly Ile Gly Tyr Thr Gly Pro Thr Val Cys Ala Ser Pro Tyr Thr
290                 295                 300

Cys Val Lys Ser Ser Asp Tyr Tyr Ser Gln Cys Leu
305                 310                 315

<210> SEQ ID NO 3
<211> LENGTH: 988
<212> TYPE: DNA
<213> ORGANISM: Lentinus similis

<400> SEQUENCE: 3

```
atgaagctct cagctctcgt agctctcgcg gcggctctcg cccctctgt ctccgctcac      60
tgtgcgttcc attgtggcct aaagttgtct actgattggt tgttgacgt gaattcccat     120
tcagatcgtt ggacttctct tgtggagggt tcaaccgtca cttcacccta ccaattcgtc    180
cgacagaaca cgaactacaa ctctcccgtc accgatgtga cttccaccga ccttcgatgc    240
aatgtcggtg gtctggcttc tgcggcttca actcagaccg ctattgttca agctggatcc    300
accgtcggtc tcgcgcttga tcaggcgatt taccaccctg gtgtcgtcaa tagtaagcac    360
cctgatctca ataggaccgt atatcatcat cctgactctc gattcagtct atatggctaa    420
agcacccggc gccgcctccg cctttgacgg ttccggaact gtttggttca aggtcaaaga    480
aatctccgct gtcaccgacg gtggaaagtc tatcagctgg ccatccgtcg gtcagactca    540
agttacattc acgattccca agagtcttcc cagcggagac tacctgatcc gcgcggaaga    600
tatcgctctt cacgtaagtg cgtttctccg agcctcagta tgcttttgat ttacggtgct    660
tcccgtacta ggttgcgcaa tcgtacggcg gtgcccagtt ctacatctcc tgtgcccaag    720
taaccgtaca aggtggaggc aacggcaagc ccggccctct gtcgctatc ccgggtgtct    780
acaccggata tgagcccggt atcctcatca acatcaacta cccctattgta cgtgcctccc    840
tcgatatcaa agtacatcct ctaatcgtac attgtctgca gcctgcaaac tacactcagc    900
ctggaccctgt gaggatgatt tcgctacctc gtgatattag cacggtacta atcattcact    960
actttcacag cccgtctgga gcggttga                                       988
```

<210> SEQ ID NO 4
<211> LENGTH: 231
<212> TYPE: PRT
<213> ORGANISM: Lentinus similis

<400> SEQUENCE: 4

```
Met Lys Leu Ser Ala Leu Val Ala Leu Ala Ala Leu Ala Pro Ser
1               5                   10                  15

Val Ser Ala His Tyr Arg Trp Thr Ser Leu Val Glu Gly Ser Thr Val
            20                  25                  30

Thr Ser Pro Tyr Gln Phe Val Arg Gln Asn Thr Asn Tyr Asn Ser Pro
        35                  40                  45

Val Thr Asp Val Thr Ser Thr Asp Leu Arg Cys Asn Val Gly Gly Leu
    50                  55                  60

Ala Ser Ala Ala Ser Thr Gln Thr Ala Ile Val Gln Ala Gly Ser Thr
65                  70                  75                  80

Val Gly Leu Ala Leu Asp Gln Ala Ile Tyr His Pro Gly Val Val Asn
                85                  90                  95

Ile Tyr Met Ala Lys Ala Pro Gly Ala Ala Ser Ala Phe Asp Gly Ser
            100                 105                 110

Gly Thr Val Trp Phe Lys Val Lys Glu Ile Ser Ala Val Thr Asp Gly
        115                 120                 125

Gly Lys Ser Ile Ser Trp Pro Ser Val Gly Gln Thr Gln Val Thr Phe
    130                 135                 140

Thr Ile Pro Lys Ser Leu Pro Ser Gly Asp Tyr Leu Ile Arg Ala Glu
145                 150                 155                 160

Asp Ile Ala Leu His Val Ala Gln Ser Tyr Gly Gly Ala Gln Phe Tyr
                165                 170                 175

Ile Ser Cys Ala Gln Val Thr Val Gln Gly Gly Asn Gly Lys Pro
            180                 185                 190

Gly Pro Leu Val Ala Ile Pro Gly Val Tyr Thr Gly Tyr Glu Pro Gly
        195                 200                 205

Ile Leu Ile Asn Ile Asn Tyr Pro Ile Pro Ala Asn Tyr Thr Gln Pro
    210                 215                 220

Gly Pro Pro Val Trp Ser Gly
225                 230
```

<210> SEQ ID NO 5
<211> LENGTH: 1072
<212> TYPE: DNA
<213> ORGANISM: Lentinus similis

<400> SEQUENCE: 5

```
atgaagtact ccatcctcgg gctcacggca ctttccttcg tcgcgtcagc cgcggctcat      60
acgctcgttt ggggcgtatg ggtcaacggc gttgatcaag agatgggag gaacatctac     120 atcaggtctc ccccgaacaa taaccccgtc aagaacctga cttcgccgga tatgacgtgc     180
aatgtcgaca tcgcggtaa ggattgtatt ttcagacata ctatgtacaa agcggatatg     240
cgtattgaca tcatggttgc gcattccact agtcgtgccc aagagcgtgc cagtcaacgc     300
tggtgatacg cttactttcg aatggtacca caacacgtag gttacgctcc ttcgacccca     360
atagccctgc actgacatca tttactcgca gacgagtaag ttcattgacc agaatcatc     420 catacttgat gctcagcgag actaggacga cgatatcatc gcatcttctc atcacggacc     480
catcgccgta tacatcgcac ctgccgcttc gaacggtcaa gggaacgttt gggtgaagct     540
```

```
cttcgaggac gcctacaacg tcaccaatag cacttgggct gtcgatcgtc tcatcactgc    600
tcatggacaa cactccgttg tggtccccca tgttgcacct ggagactacc tatttagagg    660
tgcgccatac cacttcccta cttcttgatt ctacttgacg ggttatgtta ctacatttac    720
agctgagatc attgcgctac atgaggcaga ttctctgtac tcccagaacc ctatccgtgg    780
cgcggtacgt cttgattgtt taaaacatta tgtatagcgt ctgacatagg acgtgttcat    840
tcactagcaa ttttatatct cgtgcgctca aatcaccatc aactcttccg atgactcgac    900
acctctcccc gctggtgttc ccttccccgg tgcatacacc gactccacac ccggtattca    960
attcaatatc tacactaccc ccgcgacaag ctacgttgct cccctcccca gcgtatggtc    1020
tggagcgttg ggtgggtcga ttgctcaggt cggagatgct tctctcgagt ag            1072
```

<210> SEQ ID NO 6
<211> LENGTH: 254
<212> TYPE: PRT
<213> ORGANISM: Lentinus similis

<400> SEQUENCE: 6

```
Met Lys Tyr Ser Ile Leu Gly Leu Thr Ala Leu Ser Phe Val Ala Ser
1               5                   10                  15

Ala Ala Ala His Thr Leu Val Trp Gly Val Trp Val Asn Gly Val Asp
            20                  25                  30

Gln Gly Asp Gly Arg Asn Ile Tyr Ile Arg Ser Pro Asn Asn Asn
        35                  40                  45

Pro Val Lys Asn Leu Thr Ser Pro Asp Met Thr Cys Asn Val Asp Asn
    50                  55                  60

Arg Val Val Pro Lys Ser Val Pro Val Asn Ala Gly Asp Thr Leu Thr
65                  70                  75                  80

Phe Glu Trp Tyr His Asn Thr Arg Asp Asp Ile Ile Ala Ser Ser
                85                  90                  95

His His Gly Pro Ile Ala Val Tyr Ile Ala Pro Ala Ala Ser Asn Gly
            100                 105                 110

Gln Gly Asn Val Trp Val Lys Leu Phe Glu Asp Ala Tyr Asn Val Thr
        115                 120                 125

Asn Ser Thr Trp Ala Val Asp Arg Leu Ile Thr Ala His Gly Gln His
    130                 135                 140

Ser Val Val Val Pro His Val Ala Pro Gly Asp Tyr Leu Phe Arg Ala
145                 150                 155                 160

Glu Ile Ile Ala Leu His Glu Ala Asp Ser Leu Tyr Ser Gln Asn Pro
                165                 170                 175

Ile Arg Gly Ala Gln Phe Tyr Ile Ser Cys Ala Gln Ile Thr Ile Asn
            180                 185                 190

Ser Ser Asp Asp Ser Thr Pro Leu Pro Ala Gly Val Pro Phe Pro Gly
        195                 200                 205

Ala Tyr Thr Asp Ser Thr Pro Gly Ile Gln Phe Asn Ile Tyr Thr Thr
    210                 215                 220

Pro Ala Thr Ser Tyr Val Ala Pro Pro Ser Val Trp Ser Gly Ala
225                 230                 235                 240

Leu Gly Gly Ser Ile Ala Gln Val Gly Asp Ala Ser Leu Glu
                245                 250
```

<210> SEQ ID NO 7
<211> LENGTH: 969
<212> TYPE: DNA

<213> ORGANISM: Bulgaria inquinans

<400> SEQUENCE: 7

| | | | | |
|---|---|---|---|---|
| atgtccactt | tgttgggcct | cttggccacc | gccgcctccg | tatctgccca cggattcgtc | 60 |
| gacaagatca | ccattgacgg | caccgtgtac | actggctaca | tggtgaccga gtatccatac | 120 |
| gagagcgatc | accagcctc | cattggatgg | accgaggatg | ccactgatct tggttatatc | 180 |
| gcaccagatg | cctatgcctc | cggcgacatc | atctgccaca | agaatgccac caacgcccag | 240 |
| ctctccgcca | ccgtcgccgc | tggaggaact | gttgagttgc | agtggaacac ctggccaacc | 300 |
| tctcaccacg | tccagtcat | cgactacctc | gccaactgcg | acggtgactg cgccaccgtc | 360 |
| gacaagacct | ccttggagtt | cttcaagatc | gatgcctcgg | gtcttatcaa cgacaccacc | 420 |
| gccccaggta | cctgggcctc | cgacaacttg | atttccaaca | actacacttg gaccgtcacc | 480 |
| atccctgaca | ccatcgctgc | tggaaactat | gtcctccgtc | acgagatcat gccctccac | 540 |
| agtgcaagta | gcgaggatgg | tgctcagaac | tacccacagt | gcatcaacct tgaggtgact | 600 |
| ggaggtggat | ctgacacccc | aaccggtacc | cttggagagg | ccctctacaa cgaggacgac | 660 |
| cctggtatct | tgatcaacat | ctacaccact | ggcatcacct | acaccatccc tggcccatct | 720 |
| ctttacactg | gaggctctgg | ctccgctacc | tcagccgcga | cttctgctgc cagtgttgct | 780 |
| gcttctacca | ccgctgccgc | tgcctcctcc | gctgccgcca | cttcagttgc tgctgctgcc | 840 |
| tccagctcag | ctgttgcaac | cacctttgcc | acctcgattg | ttgcctcttc ctcctcttct | 900 |
| gttgtctcca | ctgccgctgc | tgcccagacc | agcgctccga | ctggggatga cgacacctgc | 960 |
| gatgcttag | | | | | 969 |

<210> SEQ ID NO 8
<211> LENGTH: 322
<212> TYPE: PRT
<213> ORGANISM: Bulgaria inquinans

<400> SEQUENCE: 8

Met Ser Thr Leu Leu Gly Leu Leu Ala Thr Ala Ala Ser Val Ser Ala
1               5                   10                  15

His Gly Phe Val Asp Lys Ile Thr Ile Asp Gly Thr Val Tyr Thr Gly
            20                  25                  30

Tyr Met Val Thr Glu Tyr Pro Tyr Glu Ser Asp Pro Ala Ser Ile
        35                  40                  45

Gly Trp Thr Glu Asp Ala Thr Asp Leu Gly Tyr Ile Ala Pro Asp Ala
    50                  55                  60

Tyr Ala Ser Gly Asp Ile Ile Cys His Lys Asn Ala Thr Asn Ala Gln
65                  70                  75                  80

Leu Ser Ala Thr Val Ala Ala Gly Gly Thr Val Glu Leu Gln Trp Asn
                85                  90                  95

Thr Trp Pro Thr Ser His His Gly Pro Val Ile Asp Tyr Leu Ala Asn
            100                 105                 110

Cys Asp Gly Asp Cys Ala Thr Val Asp Lys Thr Ser Leu Glu Phe Phe
        115                 120                 125

Lys Ile Asp Ala Ser Gly Leu Ile Asn Asp Thr Thr Ala Pro Gly Thr
    130                 135                 140

Trp Ala Ser Asp Asn Leu Ile Ser Asn Asn Tyr Thr Trp Thr Val Thr
145                 150                 155                 160

Ile Pro Asp Thr Ile Ala Ala Gly Asn Tyr Val Leu Arg His Glu Ile
                165                 170                 175

```
Ile Ala Leu His Ser Ala Ser Ser Glu Asp Gly Ala Gln Asn Tyr Pro
            180                 185                 190

Gln Cys Ile Asn Leu Glu Val Thr Gly Gly Ser Asp Thr Pro Thr
        195                 200                 205

Gly Thr Leu Gly Glu Ala Leu Tyr Asn Glu Asp Pro Gly Ile Leu
    210                 215                 220

Ile Asn Ile Tyr Thr Thr Gly Ile Thr Tyr Thr Ile Pro Gly Pro Ser
225                 230                 235                 240

Leu Tyr Thr Gly Gly Ser Gly Ser Ala Thr Ser Ala Ala Thr Ser Ala
                245                 250                 255

Ala Ser Val Ala Ala Ser Thr Thr Ala Ala Ala Ala Ser Ser Ala Ala
                260                 265                 270

Ala Thr Ser Val Ala Ala Ala Ser Ser Ser Ala Val Ala Thr Thr
    275                 280                 285

Phe Ala Thr Ser Ile Val Ala Ser Ser Ser Ser Val Val Ser Thr
    290                 295                 300

Ala Ala Ala Ala Gln Thr Ser Ala Pro Thr Gly Asp Asp Asp Thr Cys
305                 310                 315                 320

Asp Ala

<210> SEQ ID NO 9
<211> LENGTH: 39
<212> TYPE: DNA
<213> ORGANISM: Artificial Sequence
<220> FEATURE:
<223> OTHER INFORMATION: ARTIFICIAL DNA PRIMER

<400> SEQUENCE: 9
acacaactgg ggatccacca tgcgcggatt cgcttctct                              39

<210> SEQ ID NO 10
<211> LENGTH: 40
<212> TYPE: DNA
<213> ORGANISM: Artificial Sequence
<220> FEATURE:
<223> OTHER INFORMATION: ARTIFICIAL DNA PRIMER

<400> SEQUENCE: 10
ccctctagat ctcgaggctg aagctcccta tcacgaagta                             40

<210> SEQ ID NO 11
<211> LENGTH: 43
<212> TYPE: DNA
<213> ORGANISM: Artificial Sequence
<220> FEATURE:
<223> OTHER INFORMATION: ARTIFICIAL DNA PRIMER

<400> SEQUENCE: 11
acacaactgg ggatccacca tgaagctctc agctctcgta gct                         43

<210> SEQ ID NO 12
<211> LENGTH: 35
<212> TYPE: DNA
<213> ORGANISM: Artificial Sequence
<220> FEATURE:
<223> OTHER INFORMATION: ARTIFICIAL DNA PRIMER

<400> SEQUENCE: 12
ccctctagat ctcgagtcag cgtggcacat gggtt                                  35

<210> SEQ ID NO 13
```

```
<211> LENGTH: 42
<212> TYPE: DNA
<213> ORGANISM: Artificial Sequence
<220> FEATURE:
<223> OTHER INFORMATION: ARTIFICIAL DNA PRIMER

<400> SEQUENCE: 13
acacaactgg ggatccacca tgaagtactc catcctcggg ct                              42

<210> SEQ ID NO 14
<211> LENGTH: 38
<212> TYPE: DNA
<213> ORGANISM: Artificial Sequence
<220> FEATURE:
<223> OTHER INFORMATION: ARTIFICIAL DNA PRIMER

<400> SEQUENCE: 14
ccctctagat ctcgagcctt gtcgagcgac tctatcca                                  38

<210> SEQ ID NO 15
<211> LENGTH: 1849
<212> TYPE: DNA
<213> ORGANISM: Trichoderma reesei

<400> SEQUENCE: 15
tgccatttct gacctggata ggttttccta tggtcattcc tataagagac acgctctttc          60
gtcggcccgt agatatcaga ttggtattca gtcgcacaga cgaaggtgag ttgatcctcc         120
aacatgagtt ctatgagccc ccccttgcc cccccgtt caccttgacc tgcaatgaga           180
atcccacctt ttacaagagc atcaagaagt attaatggcg ctgaatagcc tctgctcgat         240
aatatctccc cgtcatcgac aatgaacaag tccgtggctc cattgctgct gcagcgtcc          300 atactatatg gcggcgccgt cgcacagcag actgtctggg gccagtgtgg aggtattggt         360
tggagcggac ctacgaattg tgctcctggc tcagcttgtt cgaccctcaa tccttattat         420
gcgcaatgta ttccgggagc cactactatc accacttcga cccggccacc atccggtcca         480
accaccacca ccagggctac ctcaacaagc tcatcaactc cacccacgag ctctggggtc         540
cgatttgccg gcgttaacat cgcgggtttt gactttggct gtaccacaga gtgagtaccc         600
ttgtttcctg gtgttgctgg ctggttgggc gggtatacag cgaagcggac gcaagaacac         660
cgccggtccg ccaccatcaa gatgtgggtg gtaagcggcg gtgttttgta caactacctg         720
acagctcact caggaaatga gaattaatgg aagtcttgtt acagtggcac ttgcgttacc         780
tcgaaggttt atcctccgtt gaagaacttc accggctcaa acaactaccc cgatggcatc         840
ggccagatgc agcacttcgt caacgaggac gggatgacta ttttccgctt acctgtcgga         900
tggcagtacc tcgtcaacaa caatttgggc ggcaatcttg attccacgag catttccaag         960
tatgatcagc ttgttcaggg gtgcctgtct ctgggcgcat actgcatcgt cgacatccac        1020
aattatgctc gatggaacgg tgggatcatt ggtcagggcg ccctactaa tgctcaattc        1080 acgagccttt ggtcgcagtt ggcatcaaag tacgcatctc agtcgagggt gtggttcggc        1140
atcatgaatg agccccacga cgtgaacatc aacacctggg ctgccacggt ccaagaggtt        1200
gtaaccgcaa tccgcaacgc tgtgctacg tcgcaattca tctctttgcc tggaaatgat        1260
tggcaatctg ctggggcttt catatccgat ggcagtgcag ccgccctgtc tcaagtcacg        1320
aacccggatg gtcaacaac gaatctgatt tttgacgtgc acaaatactt ggactcagac        1380
aactccggta ctcacgccga atgtactaca aataacattg acggcgcctt ttctccgctt        1440
gccacttggc tccgacagaa caatcgccag gctatcctga cagaaaccgg tggtggcaac        1500
```

-continued

```
gttcagtcct gcatacaaga catgtgccag caaatccaat atctcaacca gaactcagat    1560
gtctatcttg ctatgttgg ttggggtgcc ggatcatttg atagcacgta tgtcctgacg    1620
gaaacaccga ctggcagtgg taactcatgg acggacacat ccttggtcag ctcgtgtctc    1680
gcaagaaagt agcactctga gctgaatgca gaagcctcgc caacgtttgt atctcgctat    1740
caaacatagt agctactcta tgaggctgtc tgttctcgat ttcagcttta tatagtttca    1800
tcaaacagta catattccct ctgtggccac gcaaaaaaaa aaaaaaaaa              1849
```

<210> SEQ ID NO 16
<211> LENGTH: 418
<212> TYPE: PRT
<213> ORGANISM: Trichoderma reesei

<400> SEQUENCE: 16

```
Met Asn Lys Ser Val Ala Pro Leu Leu Leu Ala Ala Ser Ile Leu Tyr
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Glu
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
        195                 200                 205

Gly Pro Thr Asn Ala Gln Phe Thr Ser Leu Trp Ser Gln Leu Ala Ser
    210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
        275                 280                 285

Ala Ala Leu Ser Gln Val Thr Asn Pro Asp Gly Ser Thr Thr Asn Leu
    290                 295                 300

Ile Phe Asp Val His Lys Tyr Leu Asp Ser Asp Asn Ser Gly Thr His
```

```
                305                 310                 315                 320
Ala Glu Cys Thr Thr Asn Asn Ile Asp Gly Ala Phe Ser Pro Leu Ala
                    325                 330                 335

Thr Trp Leu Arg Gln Asn Asn Arg Gln Ala Ile Leu Thr Glu Thr Gly
                340                 345                 350

Gly Gly Asn Val Gln Ser Cys Ile Gln Asp Met Cys Gln Gln Ile Gln
            355                 360                 365

Tyr Leu Asn Gln Asn Ser Asp Val Tyr Leu Gly Tyr Val Gly Trp Gly
        370                 375                 380

Ala Gly Ser Phe Asp Ser Thr Tyr Val Leu Thr Glu Thr Pro Thr Gly
385                 390                 395                 400

Ser Gly Asn Ser Trp Thr Asp Thr Ser Leu Val Ser Ser Cys Leu Ala
                405                 410                 415

Arg Lys

<210> SEQ ID NO 17
<211> LENGTH: 3060
<212> TYPE: DNA
<213> ORGANISM: Aspergillus fumigatus

<400> SEQUENCE: 17
```

| | |
|---|---:|
| atgagattcg gttggctcga ggtggccgct ctgacggccg cttctgtagc caatgcccag | 60 |
| gtttgtgatg cttttcccgtc attgtttcgg atatagttga caatagtcat ggaaataatc | 120 |
| aggaattggc tttctctcca ccattctacc cttcgccttg ggctgatggc cagggagagt | 180 |
| gggcagatgc ccatcgacgc gccgtcgaga tcgtttctca gatgacactg gcggagaagg | 240 |
| ttaaccttac aacgggtact gggtgggttg cgactttttt gttgacagtg agctttcttc | 300 |
| actgaccatc tacacagatg ggaaatggac cgatgcgtcg gtcaaaccgg cagcgttccc | 360 |
| aggtaagctt gcaattctgc aacaacgtgc aagtgtagtt gctaaaacgc ggtggtgcag | 420 |
| acttggtatc aactggggtc tttgtggcca ggattcccct tgggtatccc gtttctgtga | 480 |
| gctataccccg cggagtcttt cagtccttgt attatgtgct gatgattgtc tctgtatagc | 540 |
| tgacctcaac tccgccttcc ctgctggtac taatgtcgcc gcgacatggg acaagacact | 600 |
| cgcctacctt cgtggcaagg ccatgggtga ggaattcaac gacaagggcg tggacatttt | 660 |
| gctgggcct gctgctggtc ctctcggcaa ataccggac ggcggcagaa tctgggaagg | 720 |
| cttctctcct gatccggttc tcactggtgt acttttcgcc gaaactatca agggtatcca | 780 |
| agacgcgggt gtgattgcta ctgccaagca ttacattctg aatgaacagg agcatttccg | 840 |
| acaggttggc gaggcccagg gatatggtta caacatcacg gagacgatca gctccaacgt | 900 |
| ggatgacaag accatgcacg agttgtacct tggtgagta gttgacactg caaatgagga | 960 |
| ccttgattga tttgactgac ctggaatgca ggcccctttgc agatgctgtg cgcggtaaga | 1020 |
| ttttccgtag acttgacctc gcgacgaaga aatcgctgac gaaccatcgt agctggcgtt | 1080 |
| ggcgctgtca tgtgttccta caatcaaatc aacaacagct acggttgtca aaacagtcaa | 1140 |
| actctcaaca agctcctcaa ggctgagctg gcttccaag gcttcgtcat gagtgactgg | 1200 |
| agcgctcacc acagcggtgt cggcgctgcc ctcgctgggt tggatatgtc gatgcctgga | 1260 |
| gacatttcct tcgacgacgg actctccttc tggggcacga acctaactgt cagtgttctt | 1320 |
| aacggcaccg ttccagcctg gcgtgtcgat gacatggctg ttcgtatcat gaccgcgtac | 1380 |
| tacaaggttg gtcgtgaccg tcttcgtatt cccctaact tcagctcctg gacccgggat | 1440 |
| gagtacggct gggagcattc tgctgtctcc gagggagcct ggaccaaggt gaacgacttc | 1500 |

-continued

```
gtcaatgtgc agcgcagtca ctctcagatc atccgtgaga ttggtgccgc tagtacagtg    1560
ctcttgaaga acacgggtgc tcttcctttg accggcaagg aggttaaagt gggtgttctc    1620
ggtgaagacg ctggttccaa cccgtggggt gctaacggct gccccgaccg cggctgtgat    1680
aacggcactc ttgctatggc ctggggtagt ggtactgcca acttcccta ccttgtcacc     1740 cccgagcagg ctatccagcg agaggtcatc agcaacggcg gcaatgtctt gctgtgact    1800 gataacgggc tctcagcca gatggcagat gttgcatctc aatccaggtg agtgcgggct    1860
cttagaaaaa gaacgttctc tgaatgaagt tttttaacca ttgcgaacag cgtgtctttg    1920
gtgtttgtca acgccgactc tggagagggt ttcatcagtg tcgacggcaa cgagggtgac    1980
cgcaaaaatc tcactctgtg gaagaacggc gaggccgtca ttgacactgt tgtcagccac    2040
tgcaacaaca cgattgtggt tattcacagt gttgggcccg tcttgatcga ccggtggtat    2100
gataacccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc gggagtctta cggggctccc ttgctcaccg agcctaacaa tggcaatggt    2280
gctccccagg atgatttcaa cgagggcgtc ttcattgact accgtcactt tgacaagcgc    2340
aatgagaccc ccatttatga gtttggccat ggcttgagct acaccacctt tggttactct    2400
caccttcggg ttcaggccct caatagttcg agttcggcat atgtcccgac tagcggagag    2460
accaagcctg cgccaaccta tggtgagatc ggtagtgccg ccgactacct gtatcccgag    2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaaccccc tcctgaaggct ggcggcgctc ctggtggtaa ccctaccctt    2700
tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc ctctgccccg tgtctactag    3060
```

<210> SEQ ID NO 18
<211> LENGTH: 863
<212> TYPE: PRT
<213> ORGANISM: Aspergillus fumigatus

<400> SEQUENCE: 18

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95
```

```
Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
        180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
        210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
        260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
        290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
    370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
        450                 455                 460

Gln Ala Ile Gln Arg Glu Val Ile Ser Asn Gly Gly Asn Val Phe Ala
465                 470                 475                 480

Val Thr Asp Asn Gly Ala Leu Ser Gln Met Ala Asp Val Ala Ser Gln
                485                 490                 495

Ser Ser Val Ser Leu Val Phe Val Asn Ala Asp Ser Gly Glu Gly Phe
            500                 505                 510

Ile Ser Val Asp Gly Asn Glu Gly Asp Arg Lys Asn Leu Thr Leu Trp
```

```
            515                 520                 525
Lys Asn Gly Glu Ala Val Ile Asp Thr Val Ser His Cys Asn Asn
            530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
                580                 585                 590

Pro Ser Ala Lys Thr Pro Phe Thr Trp Gly Lys Thr Arg Glu Ser Tyr
                595                 600                 605

Gly Ala Pro Leu Leu Thr Glu Pro Asn Asn Gly Asn Gly Ala Pro Gln
                610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
                660                 665                 670

Ser Ala Tyr Val Pro Thr Ser Gly Glu Thr Lys Pro Ala Pro Thr Tyr
                675                 680                 685

Gly Glu Ile Gly Ser Ala Ala Asp Tyr Leu Tyr Pro Glu Gly Leu Lys
                690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
                740                 745                 750

Gly Ala Pro Gly Gly Asn Pro Thr Leu Tyr Gln Asp Leu Val Arg Val
                755                 760                 765

Ser Ala Thr Ile Thr Asn Thr Gly Asn Val Ala Gly Tyr Glu Val Pro
770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
                820                 825                 830

Gln Asp Trp Val Ile Thr Lys Tyr Pro Lys Lys Val His Val Gly Ser
                835                 840                 845

Ser Ser Arg Lys Leu Pro Leu Arg Ala Pro Leu Pro Arg Val Tyr
                850                 855                 860

<210> SEQ ID NO 19
<211> LENGTH: 39
<212> TYPE: DNA
<213> ORGANISM: Artificial Sequence
<220> FEATURE:
<223> OTHER INFORMATION: ARTIFICIAL DNA PRIMER

<400> SEQUENCE: 19
acacaactgg ggatccacca tgtccacttt gttgggcct                    39

<210> SEQ ID NO 20
```

-continued

```
<211> LENGTH: 37
<212> TYPE: DNA
<213> ORGANISM: Artificial Sequence
<220> FEATURE:
<223> OTHER INFORMATION: ARTIFICIAL DNA PRIMER

<400> SEQUENCE: 20
agatctcgag aagcttacta agcatcgcag gtgtcgt                            37

<210> SEQ ID NO 21
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 21
gcaagggatg ccatgcttgg                                               20

<210> SEQ ID NO 22
<211> LENGTH: 19
<212> TYPE: DNA
<213> ORGANISM: Artificial Sequence
<220> FEATURE:
<223> OTHER INFORMATION: ARTIFICIAL DNA PRIMER

<400> SEQUENCE: 22
catataacca attgccctc                                                19

<210> SEQ ID NO 23
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 23
cacagtgcaa gtagcgagga                                               20

<210> SEQ ID NO 24
<211> LENGTH: 20
<212> TYPE: DNA
<213> ORGANISM: Artificial Sequence
<220> FEATURE:
<223> OTHER INFORMATION: ARTIFICIAL DNA PRIMER

<400> SEQUENCE: 24
tcgctacttg cactgtggag                                               20

<210> SEQ ID NO 25
<211> LENGTH: 1599
<212> TYPE: DNA
<213> ORGANISM: Aspergillus fumigatus

<400> SEQUENCE: 25
atgctggcct ccaccttctc ctaccgcatg tacaagaccg cgctcatcct ggccgccctt    60
ctgggctctg gccaggctca gcaggtcggt acttcccagg cggaagtgca tccgtccatg   120
acctggcaga gctgcacggc tggcggcagc tgcaccacca caacggcaa ggtggtcatc    180 gacgcgaact ggcgttgggt gcacaaagtc ggcgactaca ccaactgcta caccggcaac   240
acctgggaca cgactatctg ccctgacgat gcgacctgcg catccaactg cgcccttgag   300
ggtgccaact acgaatccac ctatggtgtg accgccagcg gcaattccct ccgcctcaac   360
ttcgtcacca ccagccagca gaagaacatt ggctcgcgtc tgtacatgat gaaggacgac   420
```

```
tcgacctacg agatgtttaa gctgctgaac caggagttca ccttcgatgt cgatgtctcc    480
aacctcccct gcggtctcaa cggtgctctg tactttgtcg ccatggacgc cgacggtggc    540
atgtccaagt acccaaccaa caaggccggt gccaagtacg gtactggata ctgtgactcg    600
cagtgccctc gcgacctcaa gttcatcaac ggtcaggcca acgtcgaagg gtggcagccc    660
tcctccaacg atgccaatgc gggtaccggc aaccacgggt cctgctgcgc ggagatggat    720
atctgggagg ccaacagcat ctccacggcc ttcaccccc atccgtgcga cacgcccggc     780
caggtgatgt gcaccggtga tgcctgcggt ggcacctaca gctccgaccg ctacggcggc    840
acctgcgacc ccgacggatg tgatttcaac tccttccgcc agggcaacaa gaccttctac    900
ggccctggca tgaccgtcga caccaagagc aagtttaccg tcgtcaccca gttcatcacc    960
gacgacggca cctccagcgg caccctcaag gagatcaagc gcttctacgt gcagaacggc   1020
aaggtgatcc ccaactcgga gtcgacctgg accggcgtca gcggcaactc catcaccacc   1080
gagtactgca ccgcccagaa gagcctgttc caggaccaga acgtcttcga aaagcacggc   1140
ggcctcgagg catgggtgc tgccctcgcc caggggtatgg ttctcgtcat gtccctgtgg   1200
gatgatcact cggccaacat gctctggctc gacagcaact acccgaccac tgcctcttcc   1260
accactcccg gcgtcgcccg tggtacctgc gacatctcct ccggcgtccc tgcggatgtc   1320
gaggcgaacc accccgacgc ctacgtcgtc tactccaaca tcaaggtcgg ccccatcggc   1380
tcgaccttca cagcggtgg ctcgaacccc ggtggcggaa ccaccacgac aactaccacc   1440
cagcctacta ccaccacgac cacggctgga accctggcg caccggagt cgcacagcac    1500
tatggccagt gtggtggaat cggatggacc ggacccacaa cctgtgccag cccttatacc   1560
tgccagaagc tgaatgatta ttactctcag tgcctgtag                          1599
```

<210> SEQ ID NO 26
<211> LENGTH: 532
<212> TYPE: PRT
<213> ORGANISM: Aspergillus fumigatus

<400> SEQUENCE: 26

```
Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160
```

-continued

Asn Leu Pro Cys Gly Leu Asn Gly Ala Leu Tyr Phe Val Ala Met Asp
            165                 170                 175
Ala Asp Gly Gly Met Ser Lys Tyr Pro Thr Asn Lys Ala Gly Ala Lys
        180                 185                 190
Tyr Gly Thr Gly Tyr Cys Asp Ser Gln Cys Pro Arg Asp Leu Lys Phe
    195                 200                 205
Ile Asn Gly Gln Ala Asn Val Glu Gly Trp Gln Pro Ser Ser Asn Asp
210                 215                 220
Ala Asn Ala Gly Thr Gly Asn His Gly Ser Cys Cys Ala Glu Met Asp
225                 230                 235                 240
Ile Trp Glu Ala Asn Ser Ile Ser Thr Ala Phe Thr Pro His Pro Cys
                245                 250                 255
Asp Thr Pro Gly Gln Val Met Cys Thr Gly Asp Ala Cys Gly Gly Thr
            260                 265                 270
Tyr Ser Ser Asp Arg Tyr Gly Gly Thr Cys Asp Pro Asp Gly Cys Asp
        275                 280                 285
Phe Asn Ser Phe Arg Gln Gly Asn Lys Thr Phe Tyr Gly Pro Gly Met
    290                 295                 300
Thr Val Asp Thr Lys Ser Lys Phe Thr Val Val Thr Gln Phe Ile Thr
305                 310                 315                 320
Asp Asp Gly Thr Ser Ser Gly Thr Leu Lys Glu Ile Lys Arg Phe Tyr
                325                 330                 335
Val Gln Asn Gly Lys Val Ile Pro Asn Ser Glu Ser Thr Trp Thr Gly
            340                 345                 350
Val Ser Gly Asn Ser Ile Thr Thr Glu Tyr Cys Thr Ala Gln Lys Ser
        355                 360                 365
Leu Phe Gln Asp Gln Asn Val Phe Glu Lys His Gly Gly Leu Glu Gly
    370                 375                 380
Met Gly Ala Ala Leu Ala Gln Gly Met Val Leu Val Met Ser Leu Trp
385                 390                 395                 400
Asp Asp His Ser Ala Asn Met Leu Trp Leu Asp Ser Asn Tyr Pro Thr
                405                 410                 415
Thr Ala Ser Ser Thr Thr Pro Gly Val Ala Arg Gly Thr Cys Asp Ile
            420                 425                 430
Ser Ser Gly Val Pro Ala Asp Val Glu Ala Asn His Pro Asp Ala Tyr
        435                 440                 445
Val Val Tyr Ser Asn Ile Lys Val Gly Pro Ile Gly Ser Thr Phe Asn
    450                 455                 460
Ser Gly Gly Ser Asn Pro Gly Gly Gly Thr Thr Thr Thr Thr Thr Thr
465                 470                 475                 480
Gln Pro Thr Thr Thr Thr Thr Thr Ala Gly Asn Pro Gly Gly Thr Gly
                485                 490                 495
Val Ala Gln His Tyr Gly Gln Cys Gly Gly Ile Gly Trp Thr Gly Pro
            500                 505                 510
Thr Thr Cys Ala Ser Pro Tyr Thr Cys Gln Lys Leu Asn Asp Tyr Tyr
        515                 520                 525
Ser Gln Cys Leu
    530

<210> SEQ ID NO 27
<211> LENGTH: 1713
<212> TYPE: DNA
<213> ORGANISM: Aspergillus fumigatus

<400> SEQUENCE: 27

```
atgaagcacc ttgcatcttc catcgcattg actctactgt tgcctgccgt gcaggcccag      60
cagaccgtat ggggccaatg tatgttctgg ctgtcactgg aataagactg tatcaactgc     120
tgatatgctt ctaggtggcg gccaaggctg gtctggcccg acgagctgtg ttgccggcgc     180
agcctgtagc acactgaatc cctgtatgtt agatatcgtc ctgagtggag acttatactg     240
acttccttag actacgctca gtgtatcccg ggagccaccg cgacgtccac caccctcacg     300
acgacgacgg cggcgacgac gacatcccag accaccacca aacctaccac gactggtcca     360
actacatccg cacccaccgt gaccgcatcc ggtaaccctt tcagcggcta ccagctgtat     420 gccaaccccct actactcctc cgaggtccat actctggcca tgccttctct gcccagctcg     480
ctgcagccca aggctagtgc tgttgctgaa gtgccctcat ttgtttggct gtaagtggcc     540
ttatcccaat actgagacca actctctgac agtcgtagcg acgttgccgc caaggtgccc     600
actatgggaa cctacctggc cgacattcag gccaagaaca aggccggcgc caaccctcct     660
atcgctggta tcttcgtggt ctacgacttg ccggaccgtg actgcgccgc tctggccagt     720
aatggcgagt actcaattgc caacaacggt gtggccaact acaaggcgta cattgacgcc     780
atccgtgctc agctggtgaa gtactctgac gttcacacca tcctcgtcat cggtaggccg     840
tacacctccg ttgcgcgccg cctttctctg acatcttgca gaacccgaca gcttggccaa     900
cctggtgacc aacctcaacg tcgccaaatg cgccaatgcg cagagcgcct acctggagtg     960
tgtcgactat gctctgaagc agctcaacct gcccaacgtc gccatgtacc tcgacgcagg    1020
tatgcctcac ttcccgcatt ctgtatccct tccagacact aactcatcag gccatgcggg    1080
ctggctcgga tggcccgcca acttgggccc cgccgcaaca ctcttcgcca agtctacac    1140 cgacgcgggt tcccccgcgg ctgttcgtgg cctggccacc aacgtcgcca actacaacgc    1200
ctggtcgctc agtacctgcc cctcctacac ccagggagac cccaactgcg acgagaagaa    1260
gtacatcaac gccatggcgc ctcttctcaa ggaagccggc ttcgatgccc acttcatcat    1320
ggatacctgt aagtgcttat ccaatcgcc gatgtgtgcc gactaatcaa tgtttcagcc    1380
cggaatggcg tccagcccac gaagcaaaac gcctggggtg actggtgcaa cgtcatcggc    1440
accggcttcg gtgttcgccc ctcgactaac accggcgatc cgctccagga tgcctttgtg    1500
tggatcaagc ccgtggaga gagtgatggc acgtccaact cgacttcccc ccggtatgac    1560
gcgcactgcg gatatagtga tgctctgcag cctgctcctg aggctggtac ttggttccag    1620
gtatgtcatc cattagccag atgagggata agtgactgac ggacctaggc ctactttgag    1680
cagcttctga ccaacgctaa cccgtccttt taa                                 1713
```

<210> SEQ ID NO 28
<211> LENGTH: 454
<212> TYPE: PRT
<213> ORGANISM: Aspergillus fumigatus

<400> SEQUENCE: 28

Met Lys His Leu Ala Ser Ser Ile Ala Leu Thr Leu Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Ser Gln Thr Thr Thr Lys
65                  70                  75                  80

Pro Thr Thr Thr Gly Pro Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
            165                 170                 175

Val Tyr Asp Leu Pro Asp Arg Asp Cys Ala Ala Leu Ala Ser Asn Gly
        180                 185                 190

Glu Tyr Ser Ile Ala Asn Asn Gly Val Ala Asn Tyr Lys Ala Tyr Ile
    195                 200                 205

Asp Ala Ile Arg Ala Gln Leu Val Lys Tyr Ser Asp Val His Thr Ile
210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
            245                 250                 255

Tyr Ala Leu Lys Gln Leu Asn Leu Pro Asn Val Ala Met Tyr Leu Asp
        260                 265                 270

Ala Gly His Ala Gly Trp Leu Gly Trp Pro Ala Asn Leu Gly Pro Ala
    275                 280                 285

Ala Thr Leu Phe Ala Lys Val Tyr Thr Asp Ala Gly Ser Pro Ala Ala
290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
            325                 330                 335

Lys Tyr Ile Asn Ala Met Ala Pro Leu Leu Lys Glu Ala Gly Phe Asp
        340                 345                 350

Ala His Phe Ile Met Asp Thr Ser Arg Asn Gly Val Gln Pro Thr Lys
    355                 360                 365

Gln Asn Ala Trp Gly Asp Trp Cys Asn Val Ile Gly Thr Gly Phe Gly
370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
            405                 410                 415

Pro Arg Tyr Asp Ala His Cys Gly Tyr Ser Asp Ala Leu Gln Pro Ala
        420                 425                 430

Pro Glu Ala Gly Thr Trp Phe Gln Ala Tyr Phe Glu Gln Leu Leu Thr
    435                 440                 445

Asn Ala Asn Pro Ser Phe
    450

<210> SEQ ID NO 29
<211> LENGTH: 1415
<212> TYPE: DNA

<213> ORGANISM: Aspergillus fumigatus

<400> SEQUENCE: 29

```
atggtccatc tatcttcatt ggcagcagcc ctggctgctc tgcctctgta tgtttaccca      60
ctcacgagag gaggaacagc tttgacattg ctatagtgta tatggagctg gcctgaacac     120
agcagccaaa gccaaaggac taaagtactt tggttccgcc acggacaatc cagagctcac     180
ggactctgcg tatgtcgcgc aactgagcaa caccgatgat tttggtcaaa tcacacccgg     240
aaactccatg aaggtttgct tacgtctgcc tccctggagc attgcctcaa aagctaattg     300
gttgttttgt ttggatagtg ggatgccacc gagccttctc agaattcttt ttcgttcgca     360
aatggagacg ccgtggtcaa tctggcgaac aagaatggcc agctgatgcg atgccatact     420
ctggtctggc acagtcagct accgaactgg ggtatgtaaa cgtcttgtct attctcaaat     480
actctctaac agttgacagt ctctagcggg tcatggacca atgcgaccct tttggcggcc     540
atgaagaatc atatcaccaa tgtggttact cactacaagg ggaagtgcta cgcctgggat     600
gttgtcaatg aaggtttgtt gctccatcta tcctcaatag ttcttttgaa actgacaagc     660
ctgtcaatct agccctgaac gaggacggta ctttccgtaa ctctgtcttc taccagatca     720
tcggcccagc atacattcct attgcgttcg ccacggctgc tgccgcagat cccgacgtga     780
aactctacta caacgactac aacattgaat actcaggcgc caaagcgact gctgcgcaga     840
atatcgtcaa gatgatcaag gcctacggcg cgaagatcga cggcgtcggc ctccaggcac     900
actttatcgt cggcagcact ccgagtcaat cggatctgac gaccgtcttg aagggctaca     960
ctgctctcgg cgttgaggtg gcctataccg aacttgacat ccgcatgcag ctgccctcga    1020
ccgccgcaaa gctggcccag cagtccactg acttccaagg cgtggccgca gcatgcgtta    1080
gcaccactgg ctgcgtgggt gtcactatct gggactggac cgacaagtac tcctgggtcc    1140
ccagcgtgtt ccaaggctac ggcgcccat tgccttggga tgagaactat gtgaagaagc    1200
cagcgtacga tggcctgatg cgggtcttg agcaagcgg ctccggcacc acaacgacca    1260
ctactactac ttctactacg acaggaggta cggaccctac tggagtcgct cagaaatggg    1320
gacagtgtgg cggtattggc tggaccgggc aacaacttg tgtcagtggt accacttgcc    1380
aaaagctgaa tgactggtac tcacagtgcc tgtaa                              1415
```

<210> SEQ ID NO 30
<211> LENGTH: 397
<212> TYPE: PRT
<213> ORGANISM: Aspergillus fumigatus

<400> SEQUENCE: 30

```
Met Val His Leu Ser Ser Leu Ala Ala Ala Leu Ala Ala Leu Pro Leu
1               5                   10                  15

Val Tyr Gly Ala Gly Leu Asn Thr Ala Ala Lys Ala Lys Gly Leu Lys
            20                  25                  30

Tyr Phe Gly Ser Ala Thr Asp Asn Pro Glu Leu Thr Asp Ser Ala Tyr
        35                  40                  45

Val Ala Gln Leu Ser Asn Thr Asp Asp Phe Gly Gln Ile Thr Pro Gly
    50                  55                  60

Asn Ser Met Lys Trp Asp Ala Thr Glu Pro Gln Asn Ser Phe Ser
65                  70                  75                  80

Phe Ala Asn Gly Asp Ala Val Val Asn Leu Ala Asn Lys Asn Gly Gln
                85                  90                  95

Leu Met Arg Cys His Thr Leu Val Trp His Ser Gln Leu Pro Asn Trp
```

100                 105                 110
Val Ser Ser Gly Ser Trp Thr Asn Ala Thr Leu Leu Ala Ala Met Lys
            115                 120                 125

Asn His Ile Thr Asn Val Val Thr His Tyr Lys Gly Lys Cys Tyr Ala
    130                 135                 140

Trp Asp Val Val Asn Glu Ala Leu Asn Glu Asp Gly Thr Phe Arg Asn
145                 150                 155                 160

Ser Val Phe Tyr Gln Ile Ile Gly Pro Ala Tyr Ile Pro Ile Ala Phe
                165                 170                 175

Ala Thr Ala Ala Ala Asp Pro Asp Val Lys Leu Tyr Tyr Asn Asp
            180                 185                 190

Tyr Asn Ile Glu Tyr Ser Gly Ala Lys Ala Thr Ala Ala Gln Asn Ile
        195                 200                 205

Val Lys Met Ile Lys Ala Tyr Gly Ala Lys Ile Asp Gly Val Gly Leu
    210                 215                 220

Gln Ala His Phe Ile Val Gly Ser Thr Pro Ser Gln Ser Asp Leu Thr
225                 230                 235                 240

Thr Val Leu Lys Gly Tyr Thr Ala Leu Gly Val Glu Val Ala Tyr Thr
                245                 250                 255

Glu Leu Asp Ile Arg Met Gln Leu Pro Ser Thr Ala Ala Lys Leu Ala
            260                 265                 270

Gln Gln Ser Thr Asp Phe Gln Gly Val Ala Ala Cys Val Ser Thr
        275                 280                 285

Thr Gly Cys Val Gly Val Thr Ile Trp Asp Trp Thr Asp Lys Tyr Ser
    290                 295                 300

Trp Val Pro Ser Val Phe Gln Gly Tyr Gly Ala Pro Leu Pro Trp Asp
305                 310                 315                 320

Glu Asn Tyr Val Lys Lys Pro Ala Tyr Asp Gly Leu Met Ala Gly Leu
                325                 330                 335

Gly Ala Ser Gly Ser Gly Thr Thr Thr Thr Thr Thr Thr Thr Ser Thr
            340                 345                 350

Thr Thr Gly Gly Thr Asp Pro Thr Gly Val Ala Gln Lys Trp Gly Gln
        355                 360                 365

Cys Gly Gly Ile Gly Trp Thr Gly Pro Thr Thr Cys Val Ser Gly Thr
    370                 375                 380

Thr Cys Gln Lys Leu Asn Asp Trp Tyr Ser Gln Cys Leu
385                 390                 395

<210> SEQ ID NO 31
<211> LENGTH: 2376
<212> TYPE: DNA
<213> ORGANISM: Aspergillus fumigatus

<400> SEQUENCE: 31
atggcggttg ccaaatctat tgctgccgtg ctggtagcac tgttgcctgg tgcgcttgct      60
caggcgaata caagctatgt tgattacaat gtggaggcga atccggatct caccccctcag    120 tcggtcgcta cgattgacct gtcctttccc gactgcgaga tggaccgct cagcaagact      180 ctcgtttgcg acacgtcggc tcggccgcat gaccgagctg ctgccctggt tccatgttc     240 accttcgagg agctggtgaa caacacaggc aacactagcc ctggtgttcc aagacttggt    300
ctccctccgt accaagtatg gagcgaggct ctccatggac ttgaccgcgc caacttcaca    360
aacgagggag agtacagctg gccaccctcg ttccccatgc ctatcctgac aatgtcggcc    420
ttgaaccgaa ccctgatcaa ccagatcgcg accatcatcg caactcaagg acgagctttc    480

```
aataacgttg ggcggtatgg gctggacgtg tacgccccga atataaatgc attcagatcg    540
gctatgtggg gaagaggtca agagaccccc ggagaagacg cttactgcct ggcatcggcg    600
tatgcgtacg agtatatcac tggcatccag ggtggtgttg atccggaaca cctcaagttg    660
gtggccactg ccaaacacta tgcgggctac gatcttgaga actgggacgg tcactcccgt    720
ttgggcaacg atatgaacat tacacagcag gaactttccg aatactacac ccctcagttc    780
cttgttgcag ccagagacgc caaagtgcac agtgtcatgt gctcctacaa cgcggtaaat    840
ggggtgccca gctgcgcaaa ctcgttcttc ctccagaccc tcctccgtga cacattcggc    900
ttcgtcgagt atggttatgt atccagcgac tgcgactcgg cgtacaatgt ctggaacccg    960
cacgagtttg cggccaacat cacgggggcc gctgcagact ctatccgggc ggggacggac   1020
attgattgcg gcactactta tcaatactat ttcggcgaag cctttgacga gcaagaggtc   1080
acccgtgcag aaatcgaaag aggtgtgatc cgcctgtaca gcaacttggt gcgtctcggc   1140
tatttcgatg gcaatggaag cgtgtatcgg gacctgacgt ggaatgatgt cgtgaccacg   1200
gatgcctgga atatctcata cgaagccgct gtagaaggca ttgtcctact gaagaacgat   1260
ggaaccttgc ctctcgccaa gtcggtccgc agtgttgcat tgattgggcc ctggatgaat   1320
gtgacgactc agcttcaggg caactacttt ggaccggcgc cttatctgat tagtccgttg   1380
aatgccttcc agaattctga cttcgacgtg aactacgctt tcggcacgaa catttcatcc   1440
cactccacag atgggttttc cgaggcgttg tctgctgcga agaaatccga cgtcatcata   1500
ttcgcgggcg ggattgacaa cacttttgga gcagaagcca tggatcgcat gaatatcaca   1560
tggcccggca atcagctaca gctcatcgac cagttgagcc aactcggcaa accgctgatc   1620
gtcctccaga tgggcggcgg ccaagtcgac tcctcctcgc tcaagtccaa caagaatgtc   1680
aactccctga tctggggtgg ataccccgga caatccggcg ggcaggctct cctagacatc   1740
atcaccggca agcgcgcccc cgccggccga ctcgtggtca cgcagtaccc ggccgaatac   1800
gcaacccagt tccccgccac cgacatgagc ctgcggcctc acggcaataa tcccggccag   1860
acctacatgt ggtacaccgg cacccccgtc tacgagtttg ccacgggct cttctacacg   1920
accttccacg cctccctccc tggcaccggc aaggacaaga cctccttcaa catccaagac   1980
ctcctcacgc agccgcatcc gggcttcgca acgtcgagc aaatgccttt gctcaacttc   2040
accgtgacga tcaccaatac cggcaaggtc gcttccgact acactgctat gctcttcgcg   2100
aacaccaccg cgggacctgc tccatacccg aacaagtggc tcgtcggctt cgaccggctg   2160
gcgagcctgg aaccgcacag gtcgcagact atgaccatcc ccgtgactat cgacagcgtg   2220
gctcgtacgg atgaggccgg caatcgggtt ctctacccgg aaagtacga gttggccctg    2280
aacaatgagc ggtcggttgt ccttcagttt gtgctgacag gccgagaggc tgtgattttc    2340
aagtggcctg tagagcagca gcagatttcg tctgcg                             2376
```

<210> SEQ ID NO 32
<211> LENGTH: 792
<212> TYPE: PRT
<213> ORGANISM: Aspergillus fumigatus

<400> SEQUENCE: 32

Met Ala Val Ala Lys Ser Ile Ala Ala Val Leu Val Ala Leu Leu Pro
1               5                   10                  15

Gly Ala Leu Ala Gln Ala Asn Thr Ser Tyr Val Asp Tyr Asn Val Glu
            20                  25                  30

```
Ala Asn Pro Asp Leu Thr Pro Gln Ser Val Ala Thr Ile Asp Leu Ser
         35                   40                  45

Phe Pro Asp Cys Glu Asn Gly Pro Leu Ser Lys Thr Leu Val Cys Asp
 50                  55                  60

Thr Ser Ala Arg Pro His Asp Arg Ala Ala Leu Val Ser Met Phe
 65                  70                  75                  80

Thr Phe Glu Glu Leu Val Asn Asn Thr Gly Asn Thr Ser Pro Gly Val
                 85                  90                  95

Pro Arg Leu Gly Leu Pro Pro Tyr Gln Val Trp Ser Glu Ala Leu His
             100                 105                 110

Gly Leu Asp Arg Ala Asn Phe Thr Asn Glu Gly Glu Tyr Ser Trp Ala
             115                 120                 125

Thr Ser Phe Pro Met Pro Ile Leu Thr Met Ser Ala Leu Asn Arg Thr
             130                 135                 140

Leu Ile Asn Gln Ile Ala Thr Ile Ile Ala Thr Gln Gly Arg Ala Phe
145                 150                 155                 160

Asn Asn Val Gly Arg Tyr Gly Leu Asp Val Tyr Ala Pro Asn Ile Asn
                 165                 170                 175

Ala Phe Arg Ser Ala Met Trp Gly Arg Gly Gln Glu Thr Pro Gly Glu
             180                 185                 190

Asp Ala Tyr Cys Leu Ala Ser Ala Tyr Ala Tyr Glu Tyr Ile Thr Gly
             195                 200                 205

Ile Gln Gly Gly Val Asp Pro Glu His Leu Lys Leu Val Ala Thr Ala
210                 215                 220

Lys His Tyr Ala Gly Tyr Asp Leu Glu Asn Trp Asp Gly His Ser Arg
225                 230                 235                 240

Leu Gly Asn Asp Met Asn Ile Thr Gln Gln Glu Leu Ser Glu Tyr Tyr
                 245                 250                 255

Thr Pro Gln Phe Leu Val Ala Ala Arg Asp Ala Lys Val His Ser Val
             260                 265                 270

Met Cys Ser Tyr Asn Ala Val Asn Gly Val Pro Ser Cys Ala Asn Ser
             275                 280                 285

Phe Phe Leu Gln Thr Leu Leu Arg Asp Thr Phe Gly Phe Val Glu Asp
 290                 295                 300

Gly Tyr Val Ser Ser Asp Cys Asp Ser Ala Tyr Asn Val Trp Asn Pro
305                 310                 315                 320

His Glu Phe Ala Ala Asn Ile Thr Gly Ala Ala Asp Ser Ile Arg
             325                 330                 335

Ala Gly Thr Asp Ile Asp Cys Gly Thr Thr Tyr Gln Tyr Tyr Phe Gly
             340                 345                 350

Glu Ala Phe Asp Glu Gln Glu Val Thr Arg Ala Glu Ile Glu Arg Gly
             355                 360                 365

Val Ile Arg Leu Tyr Ser Asn Leu Val Arg Leu Gly Tyr Phe Asp Gly
             370                 375                 380

Asn Gly Ser Val Tyr Arg Asp Leu Thr Trp Asn Asp Val Thr Thr
385                 390                 395                 400

Asp Ala Trp Asn Ile Ser Tyr Glu Ala Ala Val Glu Gly Ile Val Leu
                 405                 410                 415

Leu Lys Asn Asp Gly Thr Leu Pro Leu Ala Lys Ser Val Arg Ser Val
             420                 425                 430

Ala Leu Ile Gly Pro Trp Met Asn Val Thr Thr Gln Leu Gln Gly Asn
             435                 440                 445

Tyr Phe Gly Pro Ala Pro Tyr Leu Ile Ser Pro Leu Asn Ala Phe Gln
```

```
                    450                 455                 460
Asn Ser Asp Phe Asp Val Asn Tyr Ala Phe Gly Thr Asn Ile Ser Ser
465                 470                 475                 480

His Ser Thr Asp Gly Phe Ser Glu Ala Leu Ser Ala Ala Lys Lys Ser
                    485                 490                 495

Asp Val Ile Ile Phe Ala Gly Gly Ile Asp Asn Thr Leu Glu Ala Glu
                500                 505                 510

Ala Met Asp Arg Met Asn Ile Thr Trp Pro Gly Asn Gln Leu Gln Leu
            515                 520                 525

Ile Asp Gln Leu Ser Gln Leu Gly Lys Pro Leu Ile Val Leu Gln Met
        530                 535                 540

Gly Gly Gly Gln Val Asp Ser Ser Ser Leu Lys Ser Asn Lys Asn Val
545                 550                 555                 560

Asn Ser Leu Ile Trp Gly Gly Tyr Pro Gly Gln Ser Gly Gly Gln Ala
                565                 570                 575

Leu Leu Asp Ile Ile Thr Gly Lys Arg Ala Pro Ala Gly Arg Leu Val
                580                 585                 590

Val Thr Gln Tyr Pro Ala Glu Tyr Ala Thr Gln Phe Pro Ala Thr Asp
            595                 600                 605

Met Ser Leu Arg Pro His Gly Asn Asn Pro Gly Gln Thr Tyr Met Trp
        610                 615                 620

Tyr Thr Gly Thr Pro Val Tyr Glu Phe Gly His Gly Leu Phe Tyr Thr
625                 630                 635                 640

Thr Phe His Ala Ser Leu Pro Gly Thr Gly Lys Asp Lys Thr Ser Phe
                645                 650                 655

Asn Ile Gln Asp Leu Leu Thr Gln Pro His Pro Gly Phe Ala Asn Val
                660                 665                 670

Glu Gln Met Pro Leu Leu Asn Phe Thr Val Thr Ile Thr Asn Thr Gly
            675                 680                 685

Lys Val Ala Ser Asp Tyr Thr Ala Met Leu Phe Ala Asn Thr Thr Ala
        690                 695                 700

Gly Pro Ala Pro Tyr Pro Asn Lys Trp Leu Val Gly Phe Asp Arg Leu
705                 710                 715                 720

Ala Ser Leu Glu Pro His Arg Ser Gln Thr Met Thr Ile Pro Val Thr
                725                 730                 735

Ile Asp Ser Val Ala Arg Thr Asp Glu Ala Gly Asn Arg Val Leu Tyr
                740                 745                 750

Pro Gly Lys Tyr Glu Leu Ala Leu Asn Asn Glu Arg Ser Val Val Leu
            755                 760                 765

Gln Phe Val Leu Thr Gly Arg Glu Ala Val Ile Phe Lys Trp Pro Val
        770                 775                 780

Glu Gln Gln Gln Ile Ser Ser Ala
785                 790
```

POLYPEPTIDES HAVING CELLULOLYTIC ENHANCING ACTIVITY AND POLYNUCLEOTIDES ENCODING SAME

CROSS-REFERENCE TO RELATED APPLICATIONS

This application is a divisional application of U.S. application Ser. No. 14/437,472 filed on Apr. 21, 2015, now abandoned, which is a 35 U.S.C. § 371 national application of PCT/US2013/065485 filed on Oct. 17, 2013, which claims priority or the benefit under 35 U.S.C. § 119 of U.S. Provisional Application No. 61/717,989 filed on Oct. 24, 2012, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having cellulolytic enhancing activity, catalytic domains, and cellulose binding domains, and polynucleotides encoding the polypeptides, catalytic domains, and cellulose binding domains. The invention also relates to nucleic acid constructs, vectors, and host cells comprising the polynucleotides as well as methods of producing and using the polypeptides, catalytic domains, and cellulose binding domains.

Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose. Once the cellulose is converted to glucose, the glucose can easily be fermented by yeast into ethanol.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin.

WO 2005/074647, WO 2008/148131, and WO 2011/035027 disclose GH61 polypeptides having cellulolytic enhancing activity and the polynucleotides thereof from *Thielavia terrestris*. WO 2005/074656 and WO 2010/065830 disclose GH61 polypeptides having cellulolytic enhancing activity and the polynucleotides thereof from *Thermoascus aurantiacus*. WO 2007/089290 and WO 2012/149344 disclose GH61 polypeptides having cellulolytic enhancing activity and the polynucleotides thereof from *Trichoderma reesei*. WO 2009/085935, WO 2009/085859, WO 2009/085864, and WO 2009/085868 disclose GH61 polypeptides having cellulolytic enhancing activity and the polynucleotides thereof from *Myceliophthora thermophila*. WO 2010/138754 discloses a GH61 polypeptide having cellulolytic enhancing activity and the polynucleotide thereof from *Aspergillus fumigatus*. WO 2011/005867 discloses a GH61 polypeptide having cellulolytic enhancing activity and the polynucleotide thereof from *Penicillium pinophilum*. WO 2011/039319 discloses a GH61 polypeptide having cellulolytic enhancing activity and the polynucleotide thereof from *Thermoascus* sp. WO 2011/041397 discloses a GH61 polypeptide having cellulolytic enhancing activity and the polynucleotide thereof from *Penicillium* sp. WO 2011/041504 discloses GH61 polypeptides having cellulolytic enhancing activity and the polynucleotides thereof from *Thermoascus crustaceus*. WO 2012/030799 discloses GH61 polypeptides having cellulolytic enhancing activity and the polynucleotides thereof from *Aspergillus aculeatus*. WO 2012/113340 discloses GH61 polypeptides having cellulolytic enhancing activity and the polynucleotides thereof from *Thermomyces lanuginosus*. WO 2012/122477 discloses GH61 polypeptides having cellulolytic enhancing activity and the polynucleotides thereof from *Aurantiporus alborubescens*, *Trichophaea saccata*, and *Penicillium thomii*. WO 2012/135659 discloses a GH61 polypeptide having cellulolytic enhancing activity and the polynucleotide thereof from *Talaromyces stipitatus*. WO 2012/146171 discloses GH61 polypeptides having cellulolytic enhancing activity and the polynucleotides thereof from *Humicola insolens*. WO 2012/101206 discloses GH61 polypeptides having cellulolytic enhancing activity and the polynucleotides thereof from *Malbranchea cinnamomea*, *Talaromyces leycettanus*, and *Chaetomium thermophilum*. WO 2013/043910 discloses GH61 polypeptides having cellulolytic enhancing activity and the polynucleotides thereof from *Acrophialophora fusispora* and *Corynascus sepedonium*. WO 2008/151043 and WO 2012/122518 disclose methods of increasing the activity of a GH61 polypeptide having cellulolytic enhancing activity by adding a divalent metal cation to a composition comprising the polypeptide.

There is a need in the art for new enzymes to increase efficiency and to provide cost-effective enzyme solutions for saccharification of cellulosic material.

The present invention provides GH61 polypeptides having cellulolytic enhancing activity and polynucleotides encoding the polypeptides.

SUMMARY OF THE INVENTION

The present invention relates to isolated polypeptides having cellulolytic enhancing activity selected from the group consisting of:

(a) a polypeptide having at least 60% sequence identity to the mature polypeptide of SEQ ID NO: 6, at least 65% sequence identity to the mature polypeptide of SEQ ID NO: 8, at least 75% sequence identity to the mature polypeptide of SEQ ID NO: 2, or at least 80% sequence identity to the mature polypeptide of SEQ ID NO: 4;

(b) a polypeptide encoded by a polynucleotide that hybridizes under at least high stringency conditions with the mature polypeptide coding sequence of SEQ ID NO: 1 or the cDNA sequence thereof, the mature polypeptide coding sequence of SEQ ID NO: 3 or the cDNA sequence thereof, the mature polypeptide coding sequence of SEQ ID NO: 5 or the cDNA sequence thereof, or the mature polypeptide coding sequence of SEQ ID NO: 7; or the full-length complement thereof;

(c) a polypeptide encoded by a polynucleotide having at least 60% sequence identity to the mature polypeptide coding sequence of SEQ ID NO: 5 or the cDNA sequence thereof, at least 65% sequence identity to the mature polypeptide coding sequence of SEQ ID NO: 7 or the cDNA sequence thereof, at least 75% sequence identity to the mature polypeptide coding sequence of SEQ ID NO: 1 or the cDNA sequence thereof, or at least 80% sequence identity to the mature polypeptide coding sequence of SEQ ID NO: 3;

(d) a variant of the mature polypeptide of SEQ ID NO: 2, SEQ ID NO: 4, SEQ ID NO: 6, or SEQ ID NO: 8 comprising a substitution, deletion, and/or insertion at one or more (e.g., several) positions; and (e) a fragment of the polypeptide of (a), (b), (c), or (d) that has cellulolytic enhancing activity.

The present invention also relates to isolated polypeptides comprising a catalytic domain selected from the group consisting of:

(a) a catalytic domain having at least 80% sequence identity to amino acids 20 to 245 of SEQ ID NO: 2;

(b) a catalytic domain encoded by a polynucleotide that hybridizes under at least high stringency conditions with nucleotides 58 to 1122 of SEQ ID NO: 1; the cDNA sequence thereof; or the full-length complement thereof;

(c) a catalytic domain encoded by a polynucleotide having at least 80% sequence identity to nucleotides 58 to 1122 of SEQ ID NO: 1 or the cDNA sequence thereof;

(d) a variant of amino acids 20 to 245 of SEQ ID NO: 2 comprising a substitution, deletion, and/or insertion at one or more (e.g., several) positions; and (e) a fragment of the catalytic domain of (a), (b), (c), or (d) that has cellulolytic enhancing activity.

The present invention also relates to isolated polypeptides comprising a cellulose binding domain selected from the group consisting of:

(a) a cellulose binding domain having at least 80% sequence identity to amino acids 284 to 316 of SEQ ID NO: 2;

(b) a cellulose binding domain encoded by a polynucleotide that hybridizes under at least high stringency conditions with nucleotides 1237 to 1458 of SEQ ID NO: 1; the cDNA sequence thereof; or the full-length complement thereof;

(c) a cellulose binding domain encoded by a polynucleotide having at least 80% sequence identity to nucleotides 1237 to 1458 of SEQ ID NO: 1 or the cDNA sequence thereof;

(d) a variant of amino acids 284 to 316 of SEQ ID NO: 2 comprising a substitution, deletion, and/or insertion at one or more (e.g., several) positions; and (e) a fragment of the cellulose binding domain of (a), (b), (c), or (d) that has binding activity.

The present invention also relates to isolated polynucleotides encoding the polypeptides of the present invention; nucleic acid constructs, recombinant expression vectors, and recombinant host cells comprising the polynucleotides; and methods of producing the polypeptides.

The present invention also relates to processes for degrading a cellulosic material, comprising: treating the cellulosic material with an enzyme composition in the presence of a polypeptide having cellulolytic enhancing activity of the present invention.

The present invention also relates to processes of producing a fermentation product, comprising: (a) saccharifying a cellulosic material with an enzyme composition in the presence of a polypeptide having cellulolytic enhancing activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having cellulolytic enhancing activity of the present invention.

The present invention also relates to an isolated polynucleotide encoding a signal peptide comprising or consisting of amino acids 1 to 19 of SEQ ID NO: 2, amino acids 1 to 19 of SEQ ID NO: 4, amino acids 1 to 19 of SEQ ID NO: 6, or amino acids 1 to 16 of SEQ ID NO: 8, which is operably linked to a gene encoding a protein, wherein the protein is foreign to the signal peptide; nucleic acid constructs, expression vectors, and recombinant host cells comprising the polynucleotides; and methods of producing a protein.

DEFINITIONS

Figure 1:
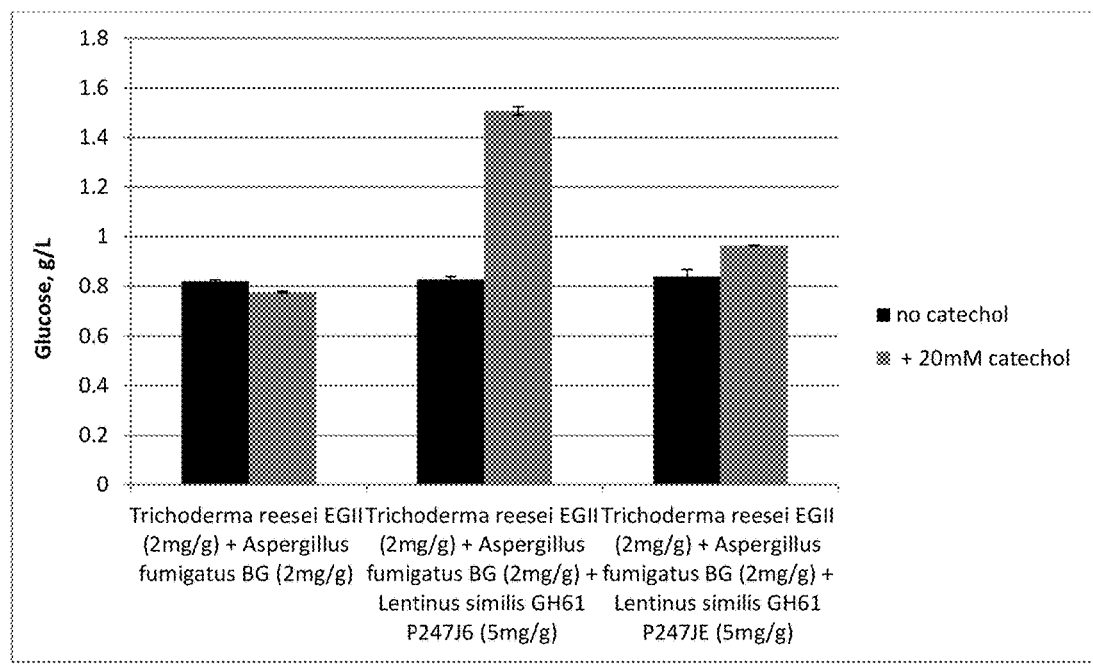
FIG. 1 shows the effect of *Lentinus similis* GH61 polypeptides on the hydrolysis of microcrystalline cellulose at pH 5.0 by a composition of *Trichoderma reesei* GH5 endoglucanase II and *Aspergillus fumigatus* GH3 beta-glucosidase.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 µmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, *J. Basic Microbiol.* 42: 55-66. One unit of beta-glucosidase is defined as 1.0 µmole of p-nitrophenolate anion produced per minute at 37° C., pH 5.0 from 1 mM p-nitrophenyl-beta-D-glucopyranoside as substrate in 100 mM succinic acid, 100 mM HEPES, 100 mM CHES, 100 mM CABS, 1 mM $CaCl_2$, 150 mM KCl, 0.01% TRITON® X-100 (4-(1,1,3,3-tetramethylbutyl)phenyl-polyethylene glycol).

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, beta-xylosidase activity is determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 µmole of p-nitrophenolate anion produced per minute at 40° C., pH 5 from 1 mM p-nitrophenyl-beta-D-xyloside in 100 mM sodium citrate containing 0.01% TWEEN® 20.

Carbohydrate binding domain: The term "carbohydrate binding domain" means the region of an enzyme that mediates binding of the enzyme to amorphous regions of a cellulose substrate. The carbohydrate binding domain (CBD) is typically found either at the N-terminal or at the C-terminal extremity of an enzyme. The term "carbohydrate binding domain" is also referred herein as "cellulose binding domain".

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters*, 187: 283-288; and Tomme et al., 1988, *Eur. J. Biochem.* 170: 575-581. In the present invention, the Tomme et al. method can be used to determine cellobiohydrolase activity.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, *Pure Appl. Chem.* 59: 257-68).

For purposes of the present invention, cellulolytic enzyme activity is determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one aspect, the cellulosic material is any biomass material. In another aspect, the cellulosic material is lignocellulose, which comprises cellulose, hemicelluloses, and lignin.

In an embodiment, the cellulosic material is agricultural residue, herbaceous material (including energy crops), municipal solid waste, pulp and paper mill residue, waste paper, or wood (including forestry residue).

In another embodiment, the cellulosic material is arundo, bagasse, bamboo, corn cob, corn fiber, corn stover, miscanthus, rice straw, switchgrass, or wheat straw.

In another embodiment, the cellulosic material is aspen, eucalyptus, fir, pine, poplar, spruce, or willow.

In another embodiment, the cellulosic material is algal cellulose, bacterial cellulose, cotton linter, filter paper, microcrystalline cellulose (e.g., AVICEL®), or phosphoric-acid treated cellulose.

In another embodiment, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means a 4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, *Biochem. J.* 280: 309-316, and Henrissat B., and Bairoch A., 1996, *Biochem. J.* 316: 695-696. The enzymes in this family were originally classified as a glycoside hydrolase family based on measurement of very weak endo-1,4-beta-D-glucanase activity in one family member. GH61 polypeptides are now classified as a lytic polysaccharide monooxygenase (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061) and placed into a new family designated "Auxiliary Activity 9" or "AA9".

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase (FAE) is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide; wherein the fragment has cellulolytic enhancing activity. In one aspect, a fragment contains at least 250 amino acid residues, e.g., at least 265 amino acid residues or at least 280 amino acid residues of SEQ ID NO: 2. In another aspect, a fragment contains at least 180 amino acid residues, e.g., at least 190 amino acid residues or at least 200 amino acid residues of SEQ ID NO: 4. In another aspect, a fragment contains at least 205 amino acid residues, e.g., at least 215 amino acid residues or at least 225 amino acid residues of SEQ ID NO: 6. In another aspect, a fragment contains at least 260 amino acid residues, e.g., at least 275 amino acid residues or at least 290 amino acid residues of SEQ ID NO: 8.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 316 of SEQ ID NO: 2 (P247JE) based on the SignalP 3.0 program (Bendtsen et al., 2004, *J. Mol. Biol.* 340: 783-795) that predicts amino acids 1 to 19 of SEQ ID NO: 2 are a signal peptide. In another aspect, the mature polypeptide is amino acids 20 to 231 of SEQ ID NO: 4 (P247J6) based on the SignalP 3.0 program that predicts amino acids 1 to 19 of SEQ ID NO: 4 are a signal peptide. In another aspect, the mature polypeptide is amino acids 20 to 254 of SEQ ID NO: 6 (P247JK) based on the SignalP 3.0 program that predicts amino acids 1 to 19 of SEQ ID NO: 6 are a signal peptide. In another aspect, the mature polypeptide is amino acids 17 to 322 of SEQ ID NO: 8 (P24NHZ) based on the SignalP 3.0 program that predicts amino acids 1 to 16 of SEQ ID NO: 8 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having cellulolytic enhancing activity. In one aspect, the mature polypeptide coding sequence is nucleotides 58 to 1458 of SEQ ID NO: 1 (D82AZW) or the cDNA sequence thereof based on the SignalP 3.0 program (Bendtsen et al., 2004, supra) that predicts nucleotides 1 to 57 of SEQ ID NO: 1 encode a signal peptide. In another aspect, the mature polypeptide coding sequence is nucleotides 58 to 985 of SEQ ID NO: 3 (D82ATR) or the cDNA sequence thereof based on the SignalP 3.0 program that predicts nucleotides 1 to 57 of SEQ ID NO: 3 encode a signal peptide. In another aspect, the mature polypeptide coding sequence is nucleotides 58 to 1069 of SEQ ID NO: 5 (D82B12) or the cDNA sequence thereof based on the SignalP 3.0 program that predicts nucleotides 1 to 57 of SEQ ID NO: 5 encode a signal peptide. In another aspect, the mature polypeptide coding sequence is nucleotides 49 to 966 of SEQ ID NO: 7

(D134SM) based on the SignalP 3.0 program that predicts nucleotides 1 to 48 of SEQ ID NO: 7 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of a polypeptide having cellulolytic enhancing activity for 1-7 days at a suitable temperature, such as 40° C.-80° C., e.g., 50° C., 55° C., 60° C., 65° C., or 70° C., and a suitable pH, such as 4-9, e.g., 4.5, 5.0, 5.5, 6.0, 6.5, 7.0, 7.5, 8.0, or 8.5, compared to a control hydrolysis with equal total protein loading without cellulolytic enhancing activity (1-50 mg of cellulolytic protein/g of cellulose in PCS).

GH61 polypeptide enhancing activity can be determined using a mixture of CELLUCLAST® 1.5 L (Novozymes A/S, Bagsværd, Denmark) in the presence of 2-3% of total protein weight Aspergillus oryzae beta-glucosidase (recombinantly produced in Aspergillus oryzae according to WO 02/095014) or 2-3% of total protein weight Aspergillus fumigatus beta-glucosidase (recombinantly produced in Aspergillus oryzae as described in WO 02/095014) of cellulase protein loading is used as the source of the cellulolytic activity.

GH61 polypeptide enhancing activity can also be determined by incubating the GH61 polypeptide with 0.5% phosphoric acid swollen cellulose (PASC), 100 mM sodium acetate pH 5, 1 mM $MnSO_4$, 0.1% gallic acid, 0.025 mg/ml of Aspergillus fumigatus beta-glucosidase, and 0.01% TRITON® X-100 for 24-96 hours at 40° C. followed by determination of the glucose released from the PASC GH61 polypeptide enhancing activity can also be determined according to WO 2013/028928 for high temperature compositions.

GH61 polypeptide enhancing activity can also be determined according to Examples 11, 15, and 21 as described herein.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

The GH61 polypeptides of the present invention have at least 20%, e.g., at least 40%, at least 50%, at least 60%, at least 70%, at least 80%, at least 90%, at least 95%, and at least 100% of the cellulolytic enhancing activity of the mature polypeptide of SEQ ID NO: 2, SEQ ID NO: 4, SEQ ID NO: 6, or SEQ ID NO: 8.

Pretreated corn stover: The term "Pretreated Corn Stover" or "PCS" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0, 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0, 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having cellulolytic enhancing activity. In one aspect, a subsequence contains at least 750 nucleotides, e.g., at least 795 nucleotides or at least 840 nucleotides of SEQ ID NO:

1. In another aspect, a subsequence contains at least 540 nucleotides, e.g., at least 570 nucleotides or at least 600 nucleotides of SEQ ID NO: 3. In another aspect, a subsequence contains at least 615 nucleotides, e.g., at least 645 nucleotides or at least 675 nucleotides of SEQ ID NO: 5. In one aspect, a subsequence contains at least 780 nucleotides, e.g., at least 825 nucleotides or at least 870 nucleotides of SEQ ID NO: 7.

Variant: The term "variant" means a polypeptide having cellulolytic enhancing activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrmann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 and 200 mM sodium phosphate pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6.

DETAILED DESCRIPTION OF THE INVENTION

Polypeptides Having Cellulolytic Enhancing Activity

In an embodiment, the present invention relates to isolated polypeptides having a sequence identity to the mature polypeptide of SEQ ID NO: 2 of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 4 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide of SEQ ID NO: 6 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide of SEQ ID NO: 8 of at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In one aspect, the polypeptides differ by up to 10 amino acids, e.g., 1, 2, 3, 4, 5, 6, 7, 8, 9, or 10, from the mature polypeptide of SEQ ID NO: 2, SEQ ID NO: 4, SEQ ID NO: 6, or SEQ ID NO: 8.

A polypeptide of the present invention preferably comprises or consists of the amino acid sequence of SEQ ID NO: 2, SEQ ID NO: 4, SEQ ID NO: 6, or SEQ ID NO: 8 or an allelic variant thereof; or is a fragment thereof having cellulolytic enhancing activity. In another aspect, the polypeptide comprises or consists of the mature polypeptide of SEQ ID NO: 2, SEQ ID NO: 4, SEQ ID NO: 6, or SEQ ID NO: 8. In another aspect, the polypeptide comprises or consists of amino acids 20 to 316 of SEQ ID NO: 2. In another aspect, the polypeptide comprises or consists of amino acids 20 to 231 of SEQ ID NO: 4. In another aspect, the polypeptide comprises or consists of amino acids 20 to 254 of SEQ ID NO: 6. In another aspect, the polypeptide comprises or consists of amino acids 17 to 322 of SEQ ID NO: 8.

In another embodiment, the present invention relates to isolated polypeptides having cellulolytic enhancing activity encoded by polynucleotides that hybridize under very low stringency conditions, low stringency conditions, medium stringency conditions, medium-high stringency conditions, high stringency conditions, or very high stringency conditions with (i) the mature polypeptide coding sequence of SEQ ID NO: 1, SEQ ID NO: 3, SEQ ID NO: 5, or SEQ ID NO: 7, (ii) the cDNA sequence of SEQ ID NO: 1, SEQ ID NO: 3, or SEQ ID NO: 5, or (iii) the full-length complement of (i) or (ii) (Sambrook et al., 1989, *Molecular Cloning, A Laboratory Manual,* 2d edition, Cold Spring Harbor, N.Y.).

The polynucleotide of SEQ ID NO: 1, SEQ ID NO: 3, SEQ ID NO: 5, or SEQ ID NO: 7, or a subsequence thereof, as well as the polypeptide of SEQ ID NO: 2, SEQ ID NO: 4, SEQ ID NO: 6, or SEQ ID NO: 8, or a fragment thereof, may be used to design nucleic acid probes to identify and clone DNA encoding polypeptides having cellulolytic enhancing activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having cellulolytic enhancing activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, SEQ ID NO: 5, or SEQ ID NO: 7, the mature polypeptide coding sequence thereof, or a subsequence thereof, the carrier material is used in a Southern blot.

For purposes of the present invention, hybridization indicates that the polynucleotides hybridize to a labeled nucleic acid probe corresponding to (i) SEQ ID NO: 1, SEQ ID NO: 3, SEQ ID NO: 5, or SEQ ID NO: 7; (ii) the mature polypeptide coding sequence of SEQ ID NO: 1, SEQ ID NO: 3, SEQ ID NO: 5, or SEQ ID NO: 7; (iii) the cDNA sequence of SEQ ID NO: 1, SEQ ID NO: 3, or SEQ ID NO: 5; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2, SEQ ID NO: 4, SEQ ID NO: 6, or SEQ ID NO: 8; the mature polypeptide thereof; or a fragment thereof. In another aspect, the nucleic acid probe is SEQ ID NO: 1, SEQ ID NO: 3, SEQ ID NO: 5, or SEQ ID NO: 7; the mature polypeptide coding sequence thereof; or the cDNA sequence thereof.

In another embodiment, the present invention relates to isolated polypeptides having cellulolytic enhancing activity encoded by polynucleotides having a sequence identity to the mature polypeptide coding sequence of SEQ ID NO: 1 or the cDNA sequence thereof of at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide coding sequence of SEQ ID NO: 3 or the cDNA sequence thereof of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; the mature polypeptide coding sequence of SEQ ID NO: 5 or the cDNA sequence thereof of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%; or the mature polypeptide coding sequence of SEQ ID NO: 7 of at least at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2, SEQ ID NO: 4, SEQ ID NO: 6, or SEQ ID NO: 8 comprising a substitution, deletion, and/or insertion at one or more (e.g., several) positions. In one aspect, the number of amino acid substitutions, deletions and/or insertions introduced into the mature polypeptide of SEQ ID NO: 2, SEQ ID NO: 4, SEQ ID NO: 6, or SEQ ID NO: 8 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide and/or thermal activity of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for cellulolytic enhancing activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Cellulolytic Enhancing Activity A polypeptide having cellulolytic enhancing activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. In one aspect, the polypeptide is a *Lentinus* polypeptide. In another aspect, the polypeptide is a *Lentinus similis* polypeptide. In another aspect, the polypeptide is a *Bulgaria* polypeptide. In another aspect, the polypeptide is a *Bulgaria inquinans* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and *Agricultural Research* Service Patent Culture Collection, Northern Regional Research Center (NRRL).

A polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by Catalytic Domains In one embodiment, the present invention also relates to catalytic domains having a sequence identity to amino acids 20 to 245 of SEQ ID NO: 2 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 20 to 245 of SEQ ID NO: 2.

The catalytic domain preferably comprises or consists of amino acids 20 to 245 of SEQ ID NO: 2; or an allelic variant thereof; or is a fragment thereof having cellulolytic enhancing activity.

In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with nucleotides 58 to 1122 of SEQ ID NO: 1; the cDNA sequence thereof; or the full-length complement thereof (Sambrook et al., 1989, supra).

In another embodiment, the present invention also relates to catalytic domains encoded by polynucleotides having a sequence identity to nucleotides 58 to 1122 of SEQ ID NO: 1, or the cDNA sequence thereof, of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

The polynucleotide encoding the catalytic domain preferably comprises or consists of nucleotides 58 to 1122 of SEQ ID NO: 1; or the cDNA sequence thereof.

In another embodiment, the present invention also relates to catalytic domain variants of amino acids 20 to 245 of SEQ ID NO: 2 comprising a substitution, deletion, and/or insertion at one or more (e.g., several) positions. In one aspect, the number of amino acid substitutions, deletions and/or insertions introduced into the sequence of amino acids 20 to 245 of SEQ ID NO: 2 is up to 10, e.g., 1, 2, 3, 4, 5, 6, 8, 9, or 10.

Binding Domains

In one embodiment, the present invention also relates to cellulose binding domains having a sequence identity to amino acids 284 to 316 of SEQ ID NO: 2 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In one aspect, the cellulose binding domains comprise amino acid sequences that differ by up to 10 amino acids, e.g., 1, 2, 3, 4, 5, 6, 7, 8, 9, or 10, from amino acids 284 to 316 of SEQ ID NO: 2.

The cellulose binding domain preferably comprises or consists of amino acids 284 to 316 of SEQ ID NO: 2; or an allelic variant thereof; or is a fragment thereof having cellulose binding activity.

In another embodiment, the present invention also relates to cellulose binding domains encoded by polynucleotides that hybridize under very low stringency conditions, low stringency conditions, medium stringency conditions, medium-high stringency conditions, high stringency conditions, or very high stringency conditions (as defined above) with nucleotides 1237 to 1458 of SEQ ID NO: 1; the cDNA sequence thereof; or the full-length complement thereof (Sambrook et al., 1989, supra).

In another embodiment, the present invention also relates to cellulose binding domains encoded by polynucleotides having a sequence identity to nucleotides 1237 to 1458 of SEQ ID NO: 1, or the cDNA sequence thereof, of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

The polynucleotide encoding the cellulose binding domain preferably comprises or consists of nucleotides 1237 to 1458 of SEQ ID NO: 1 or the cDNA sequence thereof.

In another embodiment, the present invention also relates to cellulose binding domain variants of amino acids 284 to 316 of SEQ ID NO: 2 comprising a substitution, deletion, and/or insertion at one or more (e.g., several) positions. In one aspect, the number of amino acid substitutions, deletions and/or insertions introduced into the sequence of amino acids 284 to 316 of SEQ ID NO: 2 is up to 10, e.g., 1, 2, 3, 4, 5, 6, 8, 9, or 10.

A catalytic domain operably linked to the cellulose binding domain may be from a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase. The polynucleotide encoding the catalytic domain may be obtained from any prokaryotic, eukaryotic, or other source.

Polynucleotides

The present invention also relates to isolated polynucleotides encoding a polypeptide, a catalytic domain, or cellulose binding domain of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Lentinus* or *Bulgaria*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 3, SEQ ID NO: 5, or SEQ ID NO: 7, or the cDNA sequence of SEQ ID NO: 1, SEQ ID NO: 3, or SEQ ID NO: 5, by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia col* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive or Gram negative bacterium. Gram positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus*

*clausli, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp. 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally (b) recovering the polypeptide. In one aspect, the cell is a *Lentinus* cell. In another aspect, the cell is a *Lentinus similis* cell. In another aspect, the cell is a *Bulgaria* cell. In another aspect, the cell is a *Bulgaria inquinans* cell.

The present invention also relates to methods of producing a polypeptide of the present invention, comprising (a) cultivating a recombinant host cell of the present invention under conditions conducive for production of the polypeptide; and optionally (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a whole fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed (Sticklen, 2008, *Nature Reviews* 9: 433-443). For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and optionally (b) recovering the polypeptide or domain.

Removal or Reduction of Cellulolytic Enhancing Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV)

irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may also be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having cellulolytic enhancing activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO: 1, SEQ ID NO: 3, SEQ ID NO: 5, or SEQ ID NO: 7 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially cellulolytic enhancing activity-free product are of particular interest in the production of eukaryotic polypeptides, in particular fungal proteins such as enzymes. The cellulolytic enhancing activity-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from cellulolytic enhancing activity that is produced by a method of the present invention.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid (s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, a CIP, an esterase, an expansin, a laccase, a ligninolytic enzyme, a pectinase, a catalase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Enzyme Compositions

The present invention also relates to compositions comprising a polypeptide of the present invention. Preferably, the compositions are enriched in such a polypeptide. The term "enriched" indicates that the cellulolytic enhancing activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, a CIP, an esterase, an expansin, a laccase, a ligninolytic enzyme, a pectinase, a catalase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase. The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The present invention is also directed to the following processes for using the polypeptides having cellulolytic enhancing activity, or compositions thereof.

The present invention also relates to processes for degrading a cellulosic material, comprising: treating the cellulosic material with an enzyme composition in the presence of a polypeptide having cellulolytic enhancing activity of the present invention. In one aspect, the processes further comprise recovering the degraded cellulosic material. Soluble products of degradation of the cellulosic material can be separated from insoluble cellulosic material using a method known in the art such as, for example, centrifugation, filtration, or gravity settling.

The present invention also relates to processes of producing a fermentation product, comprising: (a) saccharifying a cellulosic material with an enzyme composition in the presence of a polypeptide having cellulolytic enhancing activity of the present invention; (b) fermenting the saccharified cellulosic material with one or more (e.g., several) fermenting microorganisms to produce the fermentation product; and (c) recovering the fermentation product from the fermentation.

The present invention also relates to processes of fermenting a cellulosic material, comprising: fermenting the cellulosic material with one or more (e.g., several) fermenting microorganisms, wherein the cellulosic material is saccharified with an enzyme composition in the presence of a polypeptide having cellulolytic enhancing activity of the present invention. In one aspect, the fermenting of the cellulosic material produces a fermentation product. In another aspect, the processes further comprise recovering the fermentation product from the fermentation.

The processes of the present invention can be used to saccharify the cellulosic material to fermentable sugars and to convert the fermentable sugars to many useful fermentation products, e.g., fuel (ethanol, n-butanol, isobutanol, biodiesel, jet fuel) and/or platform chemicals (e.g., acids, alcohols, ketones, gases, oils, and the like). The production of a desired fermentation product from the cellulosic material typically involves pretreatment, enzymatic hydrolysis (saccharification), and fermentation.

The processing of the cellulosic material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd et al., 2002, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technology* 100: 10-18; Mosier et al., 2005, *Bioresource Technology* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The cellulosic material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technology* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment.

Lime pretreatment is performed with calcium oxide or calcium hydroxide at temperatures of 85-150° C. and residence times from 1 hour to several days (Wyman et al., 2005, *Bioresource Technology* 96: 1959-1966; Mosier et al., 2005, *Bioresource Technology* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technology* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber expansion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. Biotechnol.* 105-108: 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic material is present during pretreatment in amounts preferably between 10-80 wt. %, e.g., 20-70 wt. % or 30-60 wt. %, such as around 40 wt. %. The pretreated cellulosic material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Adv. Appl. *Microbiol*. 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., *ACS Symposium Series* 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Saccharification.

In the hydrolysis step, also known as saccharification, the cellulosic material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. In one aspect, the sugar is selected from the group consisting of glucose, xylose, mannose, galactose, and arabinose. The hydrolysis is performed enzymatically by an enzyme composition as described herein in the presence of a polypeptide having cellulolytic enhancing activity of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzymes(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 4.5 to about 5.5. The dry solids content is in the range of preferably about 5 to about 50 wt. %, e.g., about 10 to about 40 wt. % or about 20 to about 30 wt. %.

The enzyme compositions can comprise any protein useful in degrading the cellulosic material.

In one aspect, the enzyme composition comprises or further comprises one or more (e.g., several) proteins selected from the group consisting of a cellulase, a hemicellulase, a CIP, an esterase, an expansin, a laccase, a ligninolytic enzyme, a pectinase, a catalase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a cellobiohydrolase I, a cellobiohydrolase II, or a combination of a cellobiohydrolase I and a cellobiohydrolase II. In another aspect, the enzyme composition comprises a beta-glucosidase. In another aspect, the enzyme composition comprises an endoglucanase and a cellobiohydrolase. In another aspect, the enzyme composition comprises an endoglucanase and a cellobiohydrolase I, a cellobiohydrolase II, or a combination of a cellobiohydrolase I and a cellobiohydrolase II. In another aspect, the enzyme composition comprises an endoglucanase and a beta-glucosidase. In another aspect, the enzyme composition comprises a beta-glucosidase and a cellobiohydrolase. In another aspect, the enzyme composition comprises a beta-glucosidase and a cellobiohydrolase I, a cellobiohydrolase II, or a combination of a cellobiohydrolase I and a cellobiohydrolase II. In another aspect, the enzyme composition comprises an endoglucanase, a beta-glucosidase, and a cellobiohydrolase. In another aspect, the enzyme composition comprises an endoglucanase, a beta-glucosidase, and a cellobiohydrolase I, a cellobiohydrolase II, or a combination of a cellobiohydrolase I and a cellobiohydrolase II.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In an embodiment, the xylanase is a Family 10 xylanase. In another embodiment, the xylanase is a Family 11 xylanase. In another aspect, the enzyme composition comprises a xylosidase (e.g., beta-xylosidase).

In another aspect, the enzyme composition comprises a CIP. In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase.

In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a catalase. In another aspect, the enzyme composition comprises a peroxidase. In another aspect, the enzyme composition comprises a protease. In another aspect, the enzyme composition comprises a swollenin.

In the processes of the present invention, the enzyme(s) can be added prior to or during saccharification, saccharification and fermentation, or fermentation.

One or more (e.g., several) components of the enzyme composition may be native proteins, recombinant proteins, or a combination of native proteins and recombinant proteins. For example, one or more (e.g., several) components may be native proteins of a cell, which is used as a host cell to express recombinantly one or more (e.g., several) other components of the enzyme composition. It is understood herein that the recombinant proteins may be heterologous (e.g., foreign) and/or native to the host cell. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and a polypeptide having cellulolytic enhancing activity depend on several factors including, but not limited to, the mixture of cellulolytic enzymes and/or hemicellulolytic enzymes, the cellulosic material, the concentration of cellulosic material, the pretreatment(s) of the cellulosic material, temperature, time, pH, and inclusion of a fermenting organism (e.g., for Simultaneous Saccharification and Fermentation).

In one aspect, an effective amount of cellulolytic or hemicellulolytic enzyme to the cellulosic material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic material.

In another aspect, an effective amount of a polypeptide having cellulolytic enhancing activity to the cellulosic material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic material.

In another aspect, an effective amount of a polypeptide having cellulolytic enhancing activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic material (collectively hereinafter "polypeptides having enzyme activity") can be derived or obtained from any suitable origin, including, archaeal, bacterial, fungal, yeast, plant, or animal origin.

The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained by, e.g., site-directed mutagenesis or shuffling.

A polypeptide having enzyme activity may be a bacterial polypeptide. For example, the polypeptide may be a Gram positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia,* or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having enzyme activity.

In another aspect, the polypeptide is a *Streptococcus equisimilis, Streptococcus pyogenes, Streptococcus uberis,* or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus,* or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces,* or *Yarrowia* polypeptide having enzyme activity; or more preferably a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus,*

*Thielavia, Tolypocladium, Trichoderma, Trichophaea, Verticillium, Volvariella,* or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having enzyme activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host can be a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes A/S), CELLUCLAST™ (Novozymes A/S), NOVOZYM™ 188 (Novozymes A/S), SPEZYME™ CP (Genencor Int.), ACCELERASE™ TRIO (DuPont), FILTRASE® NL (DSM); METHAPLUS® S/L 100 (DSM), ROHAMENT™ 7069 W (Röhm GmbH), or ALTERNAFUEL® CMAX3™ (Dyadic International, Inc.). The cellulolytic enzyme preparation is added in an amount effective from about 0.001 to about 5.0 wt. % of solids, e.g., about 0.025 to about 4.0 wt. % of solids or about 0.005 to about 2.0 wt. % of solids.

Examples of bacterial endoglucanases that can be used in the processes of the present invention, include, but are not limited to, *Acidothermus cellulolyticus* endoglucanase (WO 91/05039; WO 93/15186; U.S. Pat. No. 5,275,944; WO 96/02551; U.S. Pat. No. 5,536,655; WO 00/70031; WO 05/093050), *Erwinia carotovara* endoglucanase (Saarilahti et al., 1990, *Gene* 90: 9-14), *Thermobifida fusca* endoglucanase III (WO 05/093050), and *Thermobifida fusca* endoglucanase V (WO 05/093050).

Examples of fungal endoglucanases that can be used in the present invention, include, but are not limited to, *Trichoderma reesei* endoglucanase I (Penttila et al., 1986, *Gene* 45: 253-263, *Trichoderma reesei* Cel7B endoglucanase I (GenBank:M15665), *Trichoderma reesei* endoglucanase II (Saloheimo et al., 1988, *Gene* 63:11-22), *Trichoderma reesei* Cel5A endoglucanase II (GenBank: M19373), *Trichoderma reesei* endoglucanase III (Okada et al., 1988, *Appl. Environ. Microbiol.* 64: 555-563, GenBank: AB003694), *Trichoderma reesei* endoglucanase V (Saloheimo et al., 1994, *Molecular Microbiology* 13: 219-228, GenBank:Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Fusarium oxysporum* endoglucanase (GenBank:L29381), *Humicola grisea* var. *thermoidea* endoglucanase (GenBank:AB003107), *Melanocarpus albomyces* endoglucanase (GenBank:MAL515703), *Neurospora crassa* endoglucanase (GenBank:XM_324477), *Humicola insolens* endoglucanase V, *Myceliophthora thermophila* CBS 117.65 endoglucanase, *Thermoascus aurantiacus* endoglucanase I (GenBank:AF487830) and *Trichoderma reesei* strain No. VTT-D-80133 endoglucanase (GenBank:M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Penicillium occitanis* cellobiohydrolase I (GenBank:AY690482), *Talaromyces emersonii* cellobiohydrolase I (GenBank:AF439936), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 02/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637).

Other useful endoglucanases, cellobiohydrolases, and beta-glucosidases are disclosed in numerous Glycosyl Hydrolase families using the classification according to Henrissat, 1991, *Biochem. J.* 280: 309-316, and Henrissat and Bairoch, 1996, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/

027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 5,457,046, 5,648,263, and 5,686,593.

In one aspect, the GH61 polypeptide having cellulolytic enhancing activity is used in the presence of a soluble activating divalent metal cation according to WO 2008/151043, e.g., manganese or copper.

In another aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothienopyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-6}$ to about 1, about $10^{-6}$ to about $10^{-1}$, about $10^{-4}$ to about $10^{-1}$, about 10- to about $10^{-1}$, or about $10^{-3}$ to about $10^{-2}$. In another aspect, an effective amount of such a compound described above is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-6}$ to about 1 g, about $10^{-6}$ to about $10^{-1}$ g, about $10^{-4}$ to about $10^{-1}$ g, about $10^{-}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), DEPOL™ 762P (Biocatalysts Limit, Wales, UK), ALTERNA FUEL 100P (Dyadic), and ALTERNA FUEL 200P (Dyadic).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Talaromyces lanuginosus* GH11 (WO 2012/130965), *Talaromyces thermophilus* GH11 (WO 2012/13095), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt:Q7SOW4), *Trichoderma reesei* (UniProtKB/TrEMBL:Q92458), *Talaromyces emersonii* (SwissProt:Q8X212), and *Talaromyces thermophilus* GH11 (WO 2012/13095).

Examples of acetylxylan esterases useful in the processes of the present invention include, but are not limited to, acetylxylan esterases from *Aspergillus aculeatus* (WO 2010/108918), *Chaetomium globosum* (UniProt:Q2GWX4), *Chaetomium gracile* (GeneSeqP:AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt:q7s259), *Phaeosphaeria nodorum* (UniProt:QOUHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt:A1D9T4), *Neurospora crassa* (UniProt:Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP: AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt: alcc12), *Aspergillus fumigatus* (SwissProt:Q4WW45), *Aspergillus niger* (UniProt:Q96WX9), *Aspergillus terreus* (SwissProt:QOCJP9), *Humicola insolens* (WO 2010/014706), *Penicillium aurantiogriseum* (WO 2009/068565), *Talaromyces emersonii* (UniProt:Q8X211), and *Trichoderma reesei* (UniProt:Q99024).

In a preferred embodiment, the enzyme composition is a high temperature composition, i.e., a composition that is able to hydrolyze a cellulosic material in the range of about 55° C. to about 70° C. In another preferred embodiment, the enzyme composition is a high temperature composition, i.e., a composition that is able to hydrolyze a cellulosic material at a temperature of about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., or about 70° C. In another preferred embodiment, the enzyme composition is a high temperature composition, i.e., a composition that is able to hydrolyze a cellulosic material at a temperature of at least 55° C., at least 56° C., at least 57° C., at least 58° C., at least 59° C., at least 60° C., at least 61° C., at least 62° C., at least 63° C., at least 64° C., at least 65° C., at least 66° C., at least 67° C., at least 68° C., at least 69° C., or at least 70° C.

In another preferred embodiment, the enzyme composition is a high temperature composition as disclosed in WO 2011/057140, which is incorporated herein in its entirety by reference.

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, C A, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, N Y, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous.

Any suitable hydrolyzed cellulosic material can be used in the fermentation step in practicing the present invention. The material is generally selected based on economics, i.e., costs per equivalent sugar potential, and recalcitrance to enzymatic conversion.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Yeast include strains of *Candida, Kluyveromyces,* and *Saccharomyces,* e.g., *Candida sonorensis, Kluyveromyces marxianus,* and *Saccharomyces cerevisiae.*

Examples of fermenting organisms that can ferment pentose sugars in their native state include bacterial and fungal organisms, such as some yeast. Xylose fermenting yeast include strains of *Candida,* preferably *C. sheatae* or *C. sonorensis;* and strains of *Pichia,* e.g., *P. stipitis,* such as *P. stipitis* CBS 5773. Pentose fermenting yeast include strains of *Pachysolen,* preferably *P. tannophilus.* Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocel-* *lum, Clostridium phytofermentans, Geobacillus* sp., *Thermoanaerobacter saccharolyticum,* and *Zymomonas mobilis* (Philippidis, 1996, supra).

Other fermenting organisms include strains of *Bacillus,* such as *Bacillus coagulans; Candida,* such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis,* and *C. scehatae; Clostridium,* such as *C. acetobutylicum, C. thermocellum,* and *C. phytofermentans; E. coli,* especially *E. coli* strains that have been genetically modified to improve the yield of ethanol; *Geobacillus* sp.; *Hansenula,* such as *Hansenula anomala; Klebsiella,* such as *K. oxytoca; Kluyveromyces,* such as *K. marxianus, K. lactis, K. thermotolerans,* and *K. fragilis; Schizosaccharomyces,* such as *S. pombe; Thermoanaerobacter,* such as *Thermoanaerobacter saccharolyticum;* and *Zymomonas,* such as *Zymomonas mobilis.*

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In an aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, *Appl. Biochem. Biotechnol.* 39-40: 135-147; Ho et al., 1998, *Appl. Environ. Microbiol.* 64: 1852-1859; Kotter and Ciriacy, 1993, *Appl. Microbiol. Biotechnol.* 38: 776-783; Walfridsson et al., 1995, *Appl. Environ. Microbiol.* 61: 4184-4190; Kuyper et al., 2004, *FEMS Yeast Research* 4: 655-664; Beall et al., 1991, *Biotech. Bioeng.* 38: 296-303; Ingram et al., 1998, *Biotechnol. Bioeng.* 58: 204-214; Zhang et al., 1995, *Science* 267: 240-243; Deanda et al., 1996, *Appl. Environ. Microbiol.* 62: 4465-4470; WO 03/062430).

In one aspect, the fermenting organism comprises an isolated polynucleotide encoding a polypeptide having cellulolytic enhancing activity of the present invention.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately 105 to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In one aspect, the fermentation product is an alcohol. It will be understood that the term "alcohol" encompasses a substance that contains one or more hydroxyl moieties. The alcohol can be, but is not limited to, n-butanol, isobutanol, ethanol, methanol, arabinitol, butanediol, ethylene glycol, glycerin, glycerol, 1,3-propanediol, sorbitol, xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, *World Journal of Microbiology and Biotechnology* 19(6): 595-603.

In another aspect, the fermentation product is an alkane. The alkane may be an unbranched or a branched alkane. The alkane can be, but is not limited to, pentane, hexane, heptane, octane, nonane, decane, undecane, or dodecane.

In another aspect, the fermentation product is a cycloalkane. The cycloalkane can be, but is not limited to, cyclopentane, cyclohexane, cycloheptane, or cyclooctane.

In another aspect, the fermentation product is an alkene. The alkene may be an unbranched or a branched alkene. The alkene can be, but is not limited to, pentene, hexene, heptene, or octene.

In another aspect, the fermentation product is an amino acid. The organic acid can be, but is not limited to, aspartic acid, glutamic acid, glycine, lysine, serine, or threonine. See, for example, Richard and Margaritis, 2004, *Biotechnology and Bioengineering* 87(4): 501-515.

In another aspect, the fermentation product is a gas. The gas can be, but is not limited to, methane, $H_2$, $CO_2$, or CO. See, for example, Kataoka et al., 1997, *Water Science and Technology* 36(6-7): 41-47; and Gunaseelan, 1997, *Biomass and Bioenergy* 13(1-2): 83-114.

In another aspect, the fermentation product is isoprene.

In another aspect, the fermentation product is a ketone. It will be understood that the term "ketone" encompasses a substance that contains one or more ketone moieties. The ketone can be, but is not limited to, acetone.

In another aspect, the fermentation product is an organic acid. The organic acid can be, but is not limited to, acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, or xylonic acid. See, for example, Chen and Lee, 1997, *Appl. Biochem. Biotechnol.* 63-65: 435-448.

In another aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptides

The present invention also relates to an isolated polynucleotide encoding a signal peptide comprising or consisting of amino acids 1 to 19 of SEQ ID NO: 2, amino acids 1 to 19 of SEQ ID NO: 4, amino acids 1 to 19 of SEQ ID NO: 6, or amino acids 1 to 16 of SEQ ID NO: 8. The polynucleotide may further comprise a gene encoding a protein, which is operably linked to the signal peptide. The protein is preferably foreign to the signal peptide. In one aspect, the polynucleotide encoding the signal peptide is nucleotides 1 to 57 of SEQ ID NO: 1, nucleotides 1 to 57 of SEQ ID NO: 3, nucleotides 1 to 57 of SEQ ID NO: 5, or nucleotides 1 to 48 of SEQ ID NO: 7.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and optionally (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The gene may be obtained from any prokaryotic, eukaryotic, or other source.

The present invention is further described by the following examples that should not be construed as limiting the scope of the invention.

EXAMPLES

Strains

*Lentinus similis* was used as the source of genomic DNA encoding GH61 polypeptides. The strain was isolated from a Chinese environmental sample.

*Bulgaria inquinans* O46TR was used as the source of genomic DNA encoding a GH61 polypeptide. The strain is a natural isolate from a sample obtained in Trorød Denmark. *Bulgaria inquinans* O46TR was propagated on PDA plates at 20° C.

*Aspergillus oryzae* MT3568 strain was used for expression of the GH61 polypeptides. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene.

Media and Solutions

COVE sucrose plates were composed of 342 g of sucrose, 20 g of agar powder, 20 ml of COVE salt solution, and deionized water to 1 liter. The medium was sterilized by autoclaving at 15 psi for 15 minutes (Bacteriological Analytical Manual, 8th Edition, Revision A, 1998). The medium was cooled to 60° C. and then acetamide to 10 mM, CsCl to 15 mM, and TRITON® X-100 (50 µl/500 ml) were added.

COVE top agarose was composed of 342.3 g of sucrose, 20 ml of COVE salt solution, 10 mM acetamide, 15 mM CsCl, 6 g of SEAKEM® GTG® agarose (Lonza Group Ltd., Basel, Switzerland), and deionized water to 1 liter.

COVE-2 plates for isolation were composed of 30 g of sucrose, 20 ml of COVE salt solution, 10 mM acetamide, 30 g of Noble agar, and deionized water to 1 liter.

COVE salt solution was composed of 26 g of $MgSO_4.7H_2O$, 26 g of KCl, 26 g of $KH_2PO_4$, 50 ml of COVE trace metals solution, and deionized water to 1 liter.

COVE trace metals solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4$—$H_2O$, 0.8 g of $Na_2MoO_4.2H_2O$, 10 g of $ZnSO_4.7H_2O$, and deionized water to 1 liter.

Dap-4C medium was composed of 20 g of dextrose, 10 g of maltose, 11 g of $MgSO_4.7H_2O$, 1 g of $KH_2PO_4$, 2 g of citric acid, 5.2 g of $K_3PO_4.H_2O$, 0.5 g of yeast extract (Difco), 1 ml of antifoam, 0.5 ml of KU6 trace metals solution, 2.5 g of $CaCO_3$, and deionized water to 1 liter. The medium was sterilized by autoclaving at 15 psi for 15 minutes (Bacteriological Analytical Manual, 8th Edition, Revision A, 1998). Before use, 3.5 ml of sterile 50% $(NH_4)_2HPO_4$ and 5 ml of sterile 20% lactic acid were added per 150 ml.

KU6 trace metals solution was composed of 0.13 g of $NiCl_2$, 2.5 g of $CuSO_4.5H_2O$, 13.9 g of $FeSO_4.7H_2O$, 8.45 g of $MnSO_4$—$H_2O$, 6.8 g of $ZnCl_2$, 3 g of citric acid, and deionized water to 1 liter.

LB medium was composed of 10 g of Bacto-Tryptone, 5 g of yeast extract, and 10 g of sodium chloride, and deionized water to 1 liter.

LB agar plates were composed of 10 g of Bacto-Tryptone, 5 g of yeast extract, 10 g of sodium chloride, 15 g of Bacto-agar, and deionized water to 1 liter.

PDA plates were composed of potato infusion made by boiling 300 g of sliced (washed but unpeeled) potatoes in water for 30 minutes and then decanting or straining the broth through cheesecloth. Distilled water was then added until the total volume of the suspension was one liter. Then 20 g of dextrose and 20 g of agar powder were added. The medium was sterilized by autoclaving at 15 psi for 15 minutes (Bacteriological Analytical Manual, 8th Edition, Revision A, 1998).

YP+2% glucose medium was composed of 1% yeast extract, 2% peptone, and 2% glucose in deionized water.

YP+2% maltodextrin medium was composed of 1% yeast extract, 2% peptone, and 2% maltodextrin in deionized water.

60% PEG solution was composed of 60% (w/v) polyethyleneglycol (PEG) 4000, 10 mM $CaCl_2$, and 10 mM Tris-HCl pH 7.5 in deionized water. The solution was filtered using a 0.22 µm PES membrane filter (Millipore Corp., Billerica, Mass., USA) for sterilization. After filter sterilization, the PEG 60% was stored in aliquots at −20 C until use.

Example 1: *Lentinus similis* Genomic DNA Extraction and Generation of DNA Sequence Information

*Lentinus similis* was grown on PDA plates at 26° C. for 7 days. Spores harvested from the PDA plates were inoculated into 25 ml of YP+2% glucose medium in a baffled shake flask and incubated at 26° C. for 4 days with agitation at 200 rpm.

Genomic DNA was isolated using a DNEASY® Plant Maxi Kit (QIAGEN Danmark, Copenhagen, Denmark) according to the following protocol. The fungal material from the above culture was harvested by centrifugation at 14,000×g for 2 minutes. The supernatant was removed and 0.5 g of the pellet was frozen in liquid nitrogen with quartz sand and ground to a fine powder in a pre-chilled mortar. The powder was transferred to a 15 ml centrifuge tube followed by 5 ml of AP1 buffer (QIAGEN Danmark, Copenhagen, Denmark) preheated to 65° C. and 10 µl of RNase A stock solution (100 mg/ml). The mix was then vigorously vortexed. After incubation for 10 minutes at 65° C. with regular inverting of the tube, 1.8 ml of AP2 buffer (QIAGEN Danmark, Copenhagen, Denmark) were added to the lysate by gentle mixing followed by incubation on ice for 10 minutes. The lysate was then centrifuged at 3000×g for 5 minutes at room temperature. The supernatant was decanted into a QIASHREDDER® Maxi Spin Column (QIAGEN Danmark, Copenhagen, Denmark) placed in a 50 ml collection tube and centrifuged at 3000×g for 5 minutes at room temperature. The flow-through was transferred to a new 50 ml tube and 1.5 volumes of AP3/E buffer (QIAGEN Danmark, Copenhagen, Denmark) were added followed by vortexing. A total of 15 ml of the sample was transferred into a DNEASY® Maxi Spin Column (QIAGEN Danmark, Copenhagen, Denmark) placed in a 50 ml collection tube and centrifuged at 3000×g for 5 minutes at room temperature. The flow-through was discarded and 12 ml of AW buffer (QIAGEN Danmark, Copenhagen, Denmark) were added to the DNEASY® Maxi Spin Column placed in a 50 ml collection tube and centrifuged at 3000×g for 10 minutes at room temperature. After discarding the flow-through, the centrifugation was repeated to dispose of the remaining alcohol. The DNEASY® Maxi spin column was transferred to a new 50 ml tube and 0.5 ml of AE buffer (QIAGEN Danmark, Copenhagen, Denmark) preheated to 70° C. was added. After incubation at room temperature for 5 minutes, the sample was eluted by centrifugation at 3000×g for 5 minutes at room temperature. Elution was repeated with an additional 0.5 ml of AE buffer and the eluates were combined. The concentration of the harvested DNA was measured by UV at 260 nm.

Example 2: Generation of *Lentinus similis* DNA Sequence Information

Two μg of the *Lentinus similis* genomic DNA (Example 1) was subjected to partial shotgun genome sequencing, using a service commercially available at FASTERIS SA, Switzerland. The genome sequence was analyzed for protein sequences that have GH61 glycosyl hydrolase domains (according to the CAZY definition above). Three genes and corresponding protein sequences were identified from the sequence information (SEQ ID NO: 1, SEQ ID NO: 3, and SEQ ID NO: 5).

Example 3: Construction of *Aspergillus oryzae* Expression Vectors Containing *Lentinus similis* Genomic Sequences Each Encoding a GH61 Polypeptide Two synthetic oligonucleotide primers, shown below, were designed for each of the three GH61 polypeptide genes to PCR amplify the *Lentinus similis* GH61 coding sequences from the genomic DNA prepared in Example 1. An IN-FUSION™ PCR Cloning Kit (BD Biosciences, Palo Alto, Calif., USA) was used to clone the fragments directly into the expression vector pDau109 (WO 2005/042735).

For amplification of the GH61 polypeptide coding sequence of SEQ ID NO: 1, the following primers were used:

```
Primer F-P247JE:
                                      (SEQ ID NO: 9)
5'-ACACAACTGGGGATCCACCATGCGCGGATTCGCTTCTCT-3'

Primer R-P247JE:
                                      (SEQ ID NO: 10)
5'-CCCTCTAGATCTCGAGGCTGAAGCTCCCTATCACGAAGTA-3'
```

For amplification of the GH61 polypeptide coding sequence of SEQ ID NO: 3, the following primers were used:

```
Primer F-P247J6:
                                      (SEQ ID NO: 11)
5'-ACACAACTGGGGATCCACCATGAAGCTCTCAGCTCTCGTAGCT-3'

Primer R-P247J6:
                                      (SEQ ID NO: 12)
5'-CCCTCTAGATCTCGAGTCAGCGTGGCACATGGGTT-3'
```

For amplification of the GH61 polypeptide coding sequence of SEQ ID NO: 5, the following primers were used:

```
Primer F-P247JK:
                                      (SEQ ID NO: 13)
5'-ACACAACTGGGGATCCACCATGAAGTACTCCATCCTCGGGCT-3'

Primer R-P247JK:
                                      (SEQ ID NO: 14)
5'-CCCTCTAGATCTCGAGCCTTGTCGAGCGACTCTATCCA-3'
```

Bold letters represent gene sequences. The underlined sequences are homologous to the insertion sites of pDau109.

A PHUSION® High-Fidelity PCR Kit (Finnzymes Oy, Espoo, Finland) was used for the PCR amplification. The PCR reactions were composed of 5 μl of 5×HF buffer (Finnzymes Oy, Espoo, Finland), 0.5 μl of dNTPs (10 mM), 0.5 μl of PHUSION® DNA polymerase (0.2 units/μl) (Finnzymes Oy, Espoo, Finland), 5 μM of each primer, 2 μl of *L. similis* genomic DNA (100 ng/μl), and 16.5 μl of deionized water in a total volume of 25 μl. The PCR reactions were performed using a PTC-200 DNA Engine (MJ Research Inc., Waltham, Mass., USA) programmed for 1 cycle at 95° C. for 2 minutes; 35 cycles each at 98° C. for 10 seconds, 60° C. for 30 seconds, and 72° C. for 2 minutes; and 1 cycle at 72° C. for 10 minutes. The samples were then held at 12° C. until removed from the PCR machine.

The reaction products were isolated by 1.0% agarose gel electrophoresis using 40 mM Tris base, 20 mM sodium acetate, 1 mM disodium EDTA (TAE) buffer where product bands of approximately 1200-1400 bp were excised from the gels and purified using an ILLUSTRA® GFX® PCR DNA and Gel Band Purification Kit (GE Healthcare Life Sciences, Brondby, Denmark). The fragments were then cloned into Bam HI and Xho I digested pDau109 using an IN-FUSION™ Cloning Kit resulting in plasmids pP247JE, pP247J6, and pP247JK for SEQ ID NO: 1, SEQ ID NO: 3, and SEQ ID NO: 5, respectively. Cloning of the genes into Bam HI-Xho I digested pDau 09 resulted in transcription of the *Lentinus similis* GH61 genes under the control of a NA2-tpi double promoter. NA2-tpi is a modified promoter from the gene encoding *Aspergillus niger* neutral alpha-amylase in which the untranslated leader has been replaced by an untranslated leader from the gene encoding *Aspergillus nidulans* triose phosphate isomerase.

The cloning protocol was performed according to the IN-FUSION™ Cloning Kit instructions generating three GH61 constructs. The treated plasmids and inserts were transformed into One Shot® TOP10F' Chemically Competent *E. coli* cells (Invitrogen, Carlsbad, Calif., USA) according to the manufacturer's protocol and spread onto LB plates supplemented with 0.1 mg of ampicillin per ml. After incubation at 37° C. overnight, colonies were observed growing under selection on the LB ampicillin plates. Colonies of each transformation were cultivated in LB medium supplemented with 0.1 mg of ampicillin per ml and plasmids were isolated using a QIAPREP® Spin Miniprep Kit (QIAGEN Inc., Valencia, Calif., USA).

Isolated plasmids were sequenced with vector primers and gene specific primers in order to determine representative plasmid expression clones that were free of PCR errors, and plasmids without errors were selected for expression of the GH61 polypeptides.

Example 4: Characterization of the *Lentinus similis* Genomic Sequences Encoding GH61 Polypeptides DNA sequencing of the *Lentinus similis* GH61 genomic clones was performed using an Applied Biosystems Model 3700 Automated DNA Sequencer and version 3.1 BIG-DYE™ terminator chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA). The sequences obtained were identical to the sequences from the genome sequencing (see Example 1).

The nucleotide sequence and deduced amino acid sequence of the *Lentinus similis* P247JE gene are shown in SEQ ID NO: 1 and SEQ ID NO: 2, respectively. The coding sequence of P247JE is 1461 bp including the stop codon and is interrupted by 9 introns of 59 bp (nucleotides 73 to 131), 56 bp (nucleotides 198 to 253), 56 bp (nucleotides 381 to 436), 52 bp (nucleotides 701 to 752), 54 bp (nucleotides 794 to 847), 57 bp (nucleotides 927 to 983), 53 bp (nucleotides 1044 to 1096), 62 bp (nucleotides 1263 to 1324), and 61 bp (nucleotides 1383 to 1443). The encoded predicted protein is 316 amino acids. Using the SignalP 3.0 program (Bendtsen et al., 2004, supra), a signal peptide of 19 residues was predicted. The SignalP prediction is in accord with the necessity for having a histidine reside at the N-terminus in order for proper metal binding and hence protein function to occur (See Harris et al., 2010, *Biochemistry* 49: 3305, and Quinlan et al., 2011, *Proc. Natl. Acad. Sci. USA* 108: 15079). The GH61 catalytic domain and CBM domain were predicted to be amino acids 20 to 245 and amino acids 284 to 316, respectively, by aligning the amino acid sequence of the full-length protein using BLAST to all CAZY-defined subfamily module subsequences (Cantarel et al., 2009, *Nucleic Acids Res.* 37: D233-238), where the single most significant alignment within a subfamily was used to predict the location of GH61 catalytic and CBM domains. The predicted mature protein contains 297 amino acids.

The nucleotide sequence and deduced amino acid sequence of the *Lentinus similis* P247J6 gene are shown in SEQ ID NO: 3 and SEQ ID NO: 4, respectively. The coding sequence of P247J6 is 988 bp including the stop codon and is interrupted by 5 introns of 63 bp (nucleotides 62 to 124), 55 bp (nucleotides 353 to 407), 58 bp (nucleotides 614 to 671), 54 bp (nucleotides 828 to 881), and 62 bp (nucleotides 909 to 970). The encoded predicted protein is 231 amino acids. Using the SignalP 3.0 program (Bendtsen et al., 2004, supra), a signal peptide of 19 residues was predicted. The SignalP prediction is in accord with the necessity for having a histidine reside at the N-terminus in order for proper metal binding and hence protein function to occur (See Harris et al., 2010, supra, and Quinlan et al., 2011, supra). The predicted mature polypeptide contains 212 amino acids.

The nucleotide sequence and deduced amino acid sequence of the *Lentinus similis* P247JK gene are shown in SEQ ID NO: 5 and SEQ ID NO: 6, respectively. The coding sequence of P247JK is 1072 bp including the stop codon and is interrupted by 5 introns of 76 bp (nucleotides 197 to 272), 55 bp (nucleotides 337 to 391), 50 bp (nucleotides 396 to 445), 63 bp (nucleotides 660 to 722), and 63 bp (nucleotides 785 to 847). The encoded predicted protein is 254 amino acids. Using the SignalP 3.0 program (Bendtsen et al., 2004, supra), a signal peptide of 19 residues was predicted. The SignalP prediction is in accord with the necessity for having a histidine reside at the N-terminus in order for proper metal binding and hence protein function to occur (See Harris et al., 2010, supra, and Quinlan et al., 2011, supra). The predicted mature polypeptide contains 235 amino acids.

Example 5: Expression of *Lentinus similis* GH61 Coding Sequences in *Aspergillus oryzae* MT3568

Error-free clones comprising the P247JE GH61 polypeptide coding sequence of SEQ ID NO: 1, the P247J6 GH61 polypeptide coding sequence of SEQ ID NO: 3, and the P247JK GH61 polypeptide coding sequence of SEQ ID NO: 5 were expressed in *Aspergillus oryzae* MT3568. Plasmid DNA was isolated as described in Example 3 and transformed into *Aspergillus oryzae* MT3568. *A. oryzae* MT3568 protoplasts were prepared according to the method of European Patent EP0238023, pages 14-15. Transformants resulting from the transformation of *A. oryzae* MT3568 with each of the three plasmids were inoculated into separate wells of a 96 microtiter deep well plate (Nunc A/S, Roskilde, Denmark) with each well containing 750 µl of YP+2% glucose medium or 750 µl of YP+2% maltodextrin medium. The plate was covered with Nunc pre scored vinyl sealing tape (Thermo Fisher Scientific, Roskilde, Denmark) and incubated at 26° C. stationary for 4 days. The transformants were also streaked onto COVE sucrose plates containing 10 mM acetamide, 15 mM CsCl, and TRITON® X-100 (50 µl/500 ml). The plates were incubated at 37° C. and this selection procedure was repeated in order to stabilize the transformants.

Several *Aspergillus oryzae* transformants produced the P247JE GH61 polypeptide of SEQ ID NO: 2, the P247J6 GH61 polypeptide of SEQ ID NO: 4, or the P247JK GH61 polypeptide of SEQ ID NO: 6 as judged by SDS PAGE analysis.

Example 6: Purification of the *Lentinus similis* P247JE Polypeptide

An *Aspergillus oryzae* transformant producing the recombinant P247JE GH61 polypeptide (Example 5) was inoculated in 2 liters of Dap-4C medium and incubated at 30° C. for 4 days. Mycelia were removed by filtration and the broth collected for purification of protein.

The broth was sterile filtered, washed, and concentrated by ultrafiltration first using a 0.1 m² polysulphone (PES) 10 kDa cutoff membrane on a Sartojet pump (Sartorius Stedim, Goettingen, Germany) and then using VIVASPIN® 20 (10 KDa MWCO) spin concentrators (Sartorius Stedium Biotech, Goettingen, Germany). The enzyme was purified using a 26/60 SUPERDEX™ 75 column (GE Healthcare BioSciences AB, Uppsala, Sweden) with isocratic elution using 20 mM 2-(N-morpholino)ethanesulfonic acid (MES)-125 mM sodium chloride pH 6.0. The injection volume was limited to 5 ml per run.

Fractions containing GH61 polypeptide were pooled based on $A_{280}$ absorption and concentrated by ultrafiltration using VIVASPIN® 20 (10 KDa MWCO) spin concentrators. Protein concentration was determined by $A_{280}$ absorption.

Example 7: Purification of the *Lentinus similis* P247J6 GH61 Polypeptide

An *Aspergillus oryzae* transformant producing the recombinant P247J6 GH61 polypeptide (Example 5) was inoculated into 2 liters of Dap-4C medium and incubated at 30° C. for 4 days. Mycelia were removed by filtration and the broth collected for purification of protein.

Ammonium sulfate (AMS) was added to the sterile filtered broth to 1 M and the pH adjusted to 7.5. The broth was applied to a 50/15 Butyl Toyopearl column (Tosoh Biosciences, Stuttgart, Germany) equilibrated with 25 mM trisaminomethane (Tris), 1.0 M AMS pH 7.5. The column was washed in the same buffer and eluted with a gradient from 0 to 25 mM Tris pH 7.5. Fractions containing GH61 polypeptide were pooled based on $A_{280}$ absorption and washed with 25 mM Tris pH 7.5 by ultrafiltration using VIVASPIN® 20 (10 KDa MWCO) spin concentrators to a conductivity of 2 mSi/cm. The pH was adjusted to 9.0 and applied to a 26/20 Q SEPHAROSE® column (GE Healthcare Bio-Sciences AB, Uppsala, Sweden) equilibrated with 20 mM Tris pH 9.0. The column was washed in the same buffer and the enzyme eluted with a gradient from 0 to 0.5 M sodium chloride in 20 mM Tris pH 9.0. Fractions containing GH61 polypeptide were pooled based on $A_{280}$ absorption and concentrated by ultrafiltration using VIVASPIN® 20 (10 KDa MWCO) spin concentrators. The enzyme was further purified on a 26/60 SUPERDEX™ 75 column with isocratic elution using 20 mM 2-(N-morpholino)ethanesulfonic acid (MES)-125 mM sodium chloride pH 6.0. The injection volume was limited to 5 ml per run. Protein concentration was determined by $A_{280}$ absorption.

Example 8: Purification of the *Lentinus similis* P247JK GH61 Polypeptide

An *Aspergillus oryzae* transformant producing the recombinant P247JK GH61 polypeptide (Example 5) was inoculated in 2 liters of Dap-4C medium and incubated at 30° C. for 4 days. Mycelia were removed by filtration and the broth collected for purification of protein.

Ammonium sulfate (AMS) was added to the sterile filtered broth to 1 M and the pH adjusted to 7.5. The broth was applied to a 50/15 Butyl Toyopearl column (Tosoh Biosciences, Stuttgart, Germany) equilibrated with 25 mM Tris, 1.0 AMS pH 7.5. The column was washed in the same buffer and eluted with a gradient from 0 to 25 mM Tris pH 7.5. Fractions containing GH61 polypeptide were pooled on $A_{280}$ absorption and washed with 25 mM Tris pH 7.5 by ultrafiltration using VIVASPIN® 20 (10 KDa MWCO) spin concentrators to a conductivity of 4.1 mSi/cm. The pH was adjusted to 8.0 and applied to a 26/2 Q SEPHAROSE® column equilibrated with 20 mM Tris pH 8.0. The column was washed in the same buffer and the enzyme eluted with a gradient from 0 to 0.5 M sodium chloride. Fractions containing GH61 polypeptide based on $A_{280}$ absorption were pooled and concentrated by ultrafiltration using VIVASPIN® 20 (10 KDa MWCO) spin concentrators. The enzyme was further purified on a 26/60 SUPERDEX™ 75 column with isocratic elution using 20 mM 2-(N-morpholino)ethanesulfonic acid (MES)-125 mM sodium chloride pH 6.0. The injection volume was limited to 5 ml per run. Fractions containing GH61 polypeptide were pooled based on $A_{280}$ absorption. Protein concentration determined by $A_{280}$ absorption.

Example 9: Preparation of *Trichoderma reesei* GH5 Endoglucanase II

The *Trichoderma reesei* GH5 endoglucanase II (SEQ ID NO: 15 [DNA sequence] and SEQ ID NO: 16 [deduced amino acid sequence]) was prepared recombinantly according to WO 2011/057140 using *Aspergillus oryzae* as a host. The filtered broth of the *T. reesei* endoglucanase II was desalted and buffer-exchanged into 20 mM Tris pH 8.0 using a tangential flow concentrator (Pall Filtron, Northborough, Mass., USA) equipped with a 10 kDa polyethersulfone membrane (Pall Filtron, Northborough, Mass., USA). The protein concentration was determined using a Microplate BCA™ Protein Assay Kit (Thermo Fischer Scientific, Waltham, Mass., USA) in which bovine serum albumin was used as a protein standard.

Example 10: Preparation of *Aspergillus fumigatus* Cel3A Beta-Glucosidase

The *Aspergillus fumigatus* NN055679 Cel3A beta-glucosidase. (SEQ ID NO: 17 [DNA sequence] and SEQ ID NO: 18 [deduced amino acid sequence]) was recombinantly prepared according to WO 2005/047499 using *Aspergillus oryzae* as a host. The filtered broth was adjusted to pH 8.0 with 20% sodium acetate, which made the solution turbid. To remove the turbidity, the solution was centrifuged at 20,000×g for 20 minutes, and the supernatant was filtered through a 0.2 µm filtration unit (Nalgene, Rochester, N.Y., USA). The filtrate was diluted with deionized water to reach the same conductivity as 50 mM Tris-HCl pH 8.0. The adjusted enzyme solution was applied to a Q SEPHAROSE® Fast Flow column (GE Healthcare, Piscataway, N.J., USA) equilibrated in 50 mM Tris-HCl pH 8.0 and eluted with a linear 0 to 500 mM sodium chloride gradient. Fractions were pooled and treated with 1% (w/v) activated charcoal to remove color from the beta-glucosidase pool. The charcoal was removed by filtration of the suspension through a 0.2 µm filtration unit. The filtrate was adjusted to pH 5.0 with 20% acetic acid and diluted 10 times with deionized water. The adjusted filtrate was applied to a SP SEPHAROSE® Fast Flow column (GE Healthcare, Piscataway, N.J., USA) equilibrated in 10 mM succinic acid pH 5.0 and eluted with a linear 0 to 500 mM sodium chloride gradient. Fractions were collected and analyzed for beta-glucosidase activity using p-nitrophenyl-beta-D-glucopyranoside as substrate. A p-nitrophenyl-beta-D-glucopyranoside stock solution was prepared by dissolving 50 mg of the substrate in 1.0 ml of DMSO. Just before use a substrate solution was prepared by mixing 100 µl of the stock solution with 4900 µl of 100 mM succinic acid, 100 mM HEPES, 100 mM CHES, 100 mM CABS, 1 mM $CaCl_2$, 150 mM KCl, 0.01% TRITON® X-100, pH 5.0 (assay buffer). A 200 µl volume of the substrate solution was dispensed into a tube and placed on ice followed by 20 µl of enzyme sample (diluted in 0.01% TRITON® X-100). The assay was initiated by transferring the tube to a thermomixer, which was set to an assay temperature of 37° C. The tube was incubated for 15 minutes on the thermomixer at its highest shaking rate (1400 rpm). The assay was stopped by transferring the tube back to the ice bath and adding 600 µl of a Stop solution (500 mM $H_3BO_3$/NaOH pH 9.7). Then the tube was mixed and allowed to reach room temperature. A 200 µl of supernatant was transferred to a microtiter plate and the absorbance at 405 nm was read as a measure of beta-glucosidase activity. A buffer control was included in the assay (instead of enzyme). Fractions with beta-glucosidase activity were further analyzed by SDS-PAGE using CRITERION™ 8-16% Stain-Free Tris-HCl gel (Bio-Rad Laboratories, Inc., Hercules, Calif., USA) Fractions, where only one band was seen on a Coomassie blue stained SDS-PAGE gel, were pooled as the purified product. The protein concentration was determined using a Microplate BCA™ Protein Assay Kit in which bovine serum albumin was used as a protein standard.

Example 11: Microcrystalline Cellulose Hydrolysis Assay

A 5% microcrystalline cellulose slurry was prepared by addition of 2.5 g of microcrystalline cellulose (AVICEL®

PH101; Sigma-Aldrich, St. Louis, Mo., USA) to a graduated 50 ml screw-cap conical tube followed by approximately 40 ml of double-distilled water. The conical tube was then mixed thoroughly by shaking/vortexing, and adjusted to 50 ml total with double-distilled water and mixed again. The contents of the tube were then quickly transferred to a 100 ml beaker and stirred rapidly with a magnetic stirrer.

The hydrolysis of microcrystalline cellulose was conducted using a 2.2 ml deep-well plate (Axygen, Union City, Calif., USA) in a total reaction volume of 1.0 ml. The hydrolysis was performed with 25 mg of the microcrystalline cellulose slurry (containing 100% cellulose) per ml of reaction. A 500 µl aliquot of the 5% microcrystalline cellulose slurry was pipetted into each well of the 2.2 ml deep-well plate using a 1000 µl micropipette with a wide aperture tip (end of tip cut off about 2 mm from the base). Each reaction was performed with and without the addition of catechol. In reactions not containing catechol, 200 µl of double-distilled water were added to each well. Then 100 µl of 500 mM ammonium acetate pH 5.0 containing 100 µM copper sulfate or 100 µl of 500 mM ammonium acetate pH 8.0 containing 100 µM copper sulfate were added to each well. An enzyme composition consisting of *Trichoderma reesei* GH5 endoglucanase II (loaded at 2 mg protein per g cellulose) and *Aspergillus fumigatus* GH3A beta-glucosidase (loaded at 2 mg protein per g cellulose) was prepared and then added simultaneously to each well in a volume of 100 µl. A solution containing the GH61 polypeptide (loaded at 5 mg protein per g cellulose) was then added to each well in a volume of 100 µl for a final volume of 1 ml in each reaction not containing catechol. In the reactions containing catechol, 200 µl of 100 mM catechol were added to each of the appropriate wells for a final volume of 1 ml and a final catechol concentration of 20 mM. The plate was then sealed using an ALPS-300™ plate heat sealer (Abgene, Epsom, United Kingdom), mixed thoroughly, and incubated at 50° C. for 72 hours. All experiments reported were performed in triplicate.

Following hydrolysis, samples were filtered using a 0.45 µm MULTISCREEN® 96-well filter plate (Millipore, Bedford, Mass., USA) and filtrates analyzed for glucose content as described below. When not used immediately, filtered aliquots were frozen at −20° C. The sugar concentrations of the samples were measured using a 4.6×250 mm AMINEX® HPX-87H column (Bio-Rad Laboratories, Inc., Hercules, Calif., USA) by elution with 0.05% w/w benzoic acid-0.005 M $H_2SO_4$ at 65° C. at a flow rate of 0.6 ml per minute, and quantitation by integration of the glucose signal from refractive index detection (CHEMSTATION®, AGILENT® 1100 HPLC, Agilent Technologies, Santa Clara, Calif., USA) calibrated by pure glucose samples.

All HPLC data processing was performed using MICROSOFT EXCEL™ software (Microsoft, Richland, Wash., USA). The resultant glucose was used for comparison of each reaction. Triplicate data points were averaged and standard deviation was calculated.

Example 12: Effect of the *Lentinus similis* GH61 Polypeptides on the Hydrolysis of Microcrystalline Cellulose The *Lentinus similis* P247JE and P247J6 GH61 polypeptides were each evaluated for the ability to enhance the hydrolysis of microcrystalline cellulose in the presence of *Trichoderma reesei* GH5 endoglucanase II (loaded at 2 mg protein per g cellulose) and *Aspergillus fumigatus* GH3A beta-glucosidase (loaded at 2 mg protein per g cellulose) with and without the addition of 20 mM catechol at 50° C. The *Lentinus similis* GH61 polypeptides were added separately at 5 mg protein per g cellulose. The composition of *T. reesei* GH5 endoglucanase II (loaded at 2 mg protein per g cellulose) and *A. fumigatus* GH3A beta-glucosidase (loaded at 2 mg protein per g cellulose) with and without 20 mM catechol was also run as controls without added GH61 polypeptide.

The assay was performed as described in Example 11. The 1 ml reactions with microcrystalline cellulose were conducted for 72 hours in 50 mM ammonium acetate pH 5.0 containing 10 µM copper sulfate or 50 mM ammonium acetate pH 8.0 containing 10 µM copper sulfate. All reactions were performed in triplicate and involved single mixing at the beginning of hydrolysis.

Figure 2:
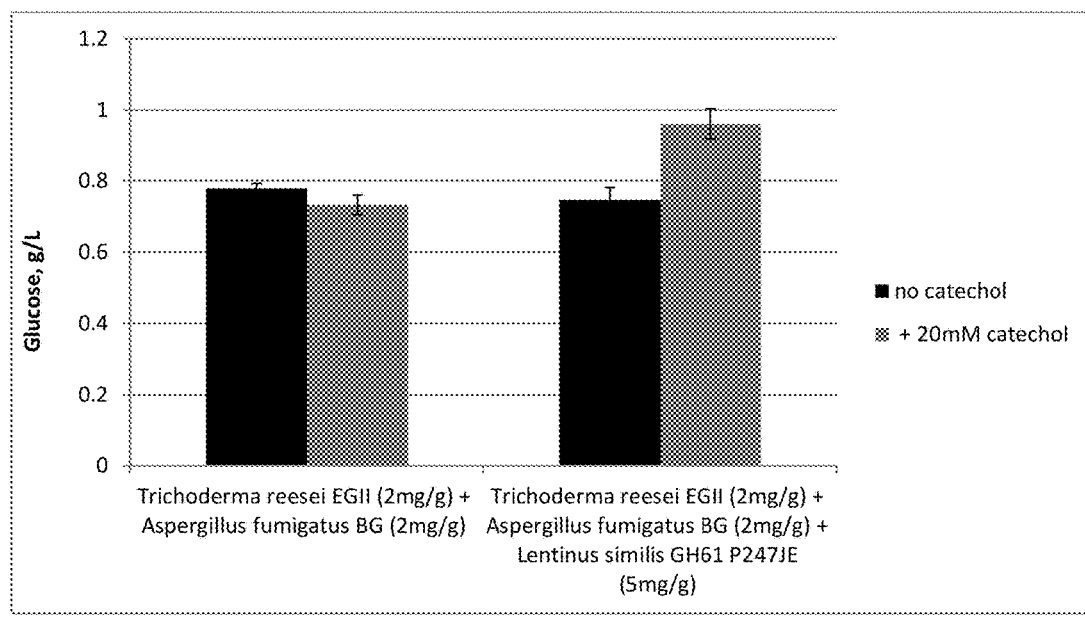
FIG. 2 shows the effect of *Lentinus similis* GH61 polypeptides on the hydrolysis of microcrystalline cellulose at pH 8.0 by a composition of *Trichoderma reesei* GH5 endoglucanase II and *Aspergillus fumigatus* GH3 beta-glucosidase.

As shown in FIGS. 1 and 2, hydrolysis of the microcrystalline cellulose by the composition of *T. reesei* GH5 endoglucanase II and *A. fumigatus* GH3A beta-glucosidase without catechol produced similar results as that obtained with either *L. similis* GH61 polypeptide added to the composition of *T. reesei* GH5 endoglucanase II and *A. fumigatus* GH3A beta-glucosidase without catechol. The addition of *L. similis* GH61 polypeptide to the composition of *T. reesei* GH5 endoglucanase II and *A. fumigatus* GH3A beta-glucosidase without catechol did not improve hydrolysis of the microcrystalline cellulose. However, as shown in FIGS. 1 and 2, the addition of either *L. similis* GH61 polypeptide to the composition of *T. reesei* GH5 endoglucanase II and *A. fumigatus* GH3A beta-glucosidase with 20 mM catechol resulted in a higher degree of glucose production (shown in g/L) compared to the addition of either *L. similis* GH61 polypeptide to the composition of *T. reesei* GH5 endoglucanase II and *A. fumigatus* GH3A beta-glucosidase without added catechol and compared to the composition of *T. reesei* GH5 endoglucanase II and *A. fumigatus* GH3A beta-glucosidase without GH61 polypeptide and with or without added catechol. As shown in FIG. 1, the results demonstrated a 1.82-fold improvement (or 82% increase) or 1.15-fold improvement (or 15% increase) in hydrolysis of the microcrystalline cellulose by *L. similis* GH61 polypeptide addition (*L. similis* GH61 polypeptide P247J6 and *L. similis* GH61 polypeptide P247JE, respectively) to the composition of *T. reesei* GH5 endoglucanase II and *A. fumigatus* GH3A beta-glucosidase with catechol compared to without catechol at pH 5.0. As shown in FIG. 2, the results demonstrated a 1.29-fold improvement (or 29% increase) in hydrolysis of the microcrystalline cellulose by *L. similis* P247JE GH61 polypeptide addition to the composition of *T. reesei* GH5 endoglucanase II and *A. fumigatus* GH3A beta-glucosidase with catechol compared to without catechol at pH 8.0.

Example 13: Preparation of Phosphoric Acid Swollen Cellulose (PASC)

A 1% phosphoric acid swollen cellulose (PASC) slurry was prepared from microcrystalline cellulose (AVICEL® PH101, Sigma-Aldrich, St. Louis, Mo., USA) using the protocol described by Zhang et al., 2006, *Biomacromolecules* 7: 644-648.

Example 14: Preparation of Copper(II) Preincubated GH61 Polypeptides

*Lentinus similis* GH61 polypeptides at 0.25 gram per liter were each preincubated with equal molar copper sulfate at 23° C. for 30 minutes, prior to addition to a PASC hydrolysis suspension.

Example 15: Evaluation of the Degradation of Phosphoric Acid Swollen Cellulose by *Lentinus similis* GH61 Polypeptides The activity of *Lentinus similis* GH61 polypeptides on phosphoric acid swollen cellulose (PASC) was evaluated according to the procedure described below.

The degradation of PASC was conducted using 2.0 ml deep-well plates (Axygen Scientific, Union City, Calif., USA) in a total reaction volume of 1.0 ml. Each hydrolysis was performed with 5 mg of PASC per ml of 100 mM sodium tartrate, Bis-Tris, glycylglycine (TBG) buffer at pH 5 (Molecular Dimensions Inc., Apopka, Fla., USA) containing *L. similis* P247JE, P247JK, or P247J6 GH61 polypeptide at 10 mg protein per gram of cellulose, 1 mM calcium chloride, plus pyrogallol, 4-hydroxy-5-methyl-3-furanone, cysteine, or ascorbate at 5 mM as cofactor for the GH61 polypeptide. The plate was then sealed using an ALPS-300™ or ALPS-3000™ plate heat sealer (Abgene, Epsom, United Kingdom), mixed thoroughly, and incubated at 50° C. for 1 day in an Isotemp Plus incubator (Thermo Fisher Scientific Inc., Waltham, Mass., USA). The final pH was measured after completion of the reactions. All experiments were performed at least in triplicate.

Following hydrolysis, samples were filtered using a 0.45 µm MULTISCREEN® 96-well filter plate (Millipore, Bedford, Mass., USA). The filtrates were reacted with *Aspergillus oryzae* GH3A beta-glucosidase at 50 mg protein per liter at 50° C. for at least 24 hours. As controls, a 1-hour beta-glucosidase reaction was compared to a 24-hour reaction, and the beta-glucosidase reaction without pH adjustment of the GH61-PASC reaction was compared to beta-glucosidase reaction with the pH of the GH61-PASC reaction adjusted to 5. No significant differences were observed.

Reacted samples were analyzed for glucose and cellobiose content as described below. When not used immediately, filtered aliquots were frozen at −20° C. The sugar concentrations of samples, diluted to appropriate concentrations in 0.005 M $H_2SO_4$, were measured using a 4.6×250 mm AMINEX® HPX-87H column by elution with 0.05% (w/w) benzoic acid-0.005 M $H_2SO_4$ at 65° C. at a flow rate of 0.6 ml per minute, and quantitated by integration of the glucose and cellobiose signals from refractive index detection calibrated by pure sugar samples. The resultant glucose and cellobiose equivalents were used to calculate the percentage of cellulose conversion for each reaction. Measured sugar concentrations were adjusted for the appropriate dilution factor. Data were processed using MICROSOFT EXCEL™ software.

Percent conversion was calculated based on the mass ratio of solubilized glucosyl units to the initial mass of insoluble cellulose. Only glucose and cellobiose were measured for soluble sugars, as cellodextrins longer than cellobiose were present in negligible concentrations (due to enzymatic hydrolysis). The extent of total cellulose conversion was calculated using the following equation:

$$\% \text{ conversion} = \frac{(([\text{cellobiose}](\text{mg/ml}) \times 1.053) + ([\text{glucose}](\text{mg/ml}))/1.111)}{[\text{cellulose}](\text{mg/ml})}$$

The 1.111 and 1.053 factors for glucose and cellobiose, respectively, take into account the increase in mass when the glucosyl units in cellulose (average molecular mass of 162 daltons) are converted to glucose (molecular mass of 180 daltons) or cellobiose glucosyl units (average molecular mass of 171 daltons).

Figure 3:
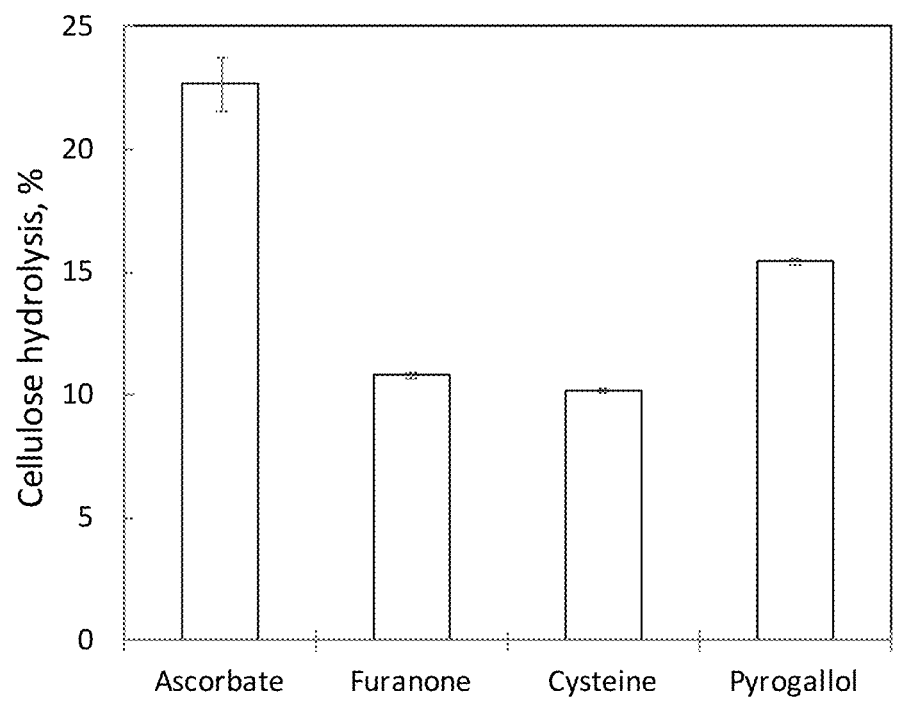
FIG. 3 shows the activity of *Lentinus similis* P247JE GH61 polypeptide in degrading phosphoric acid-swollen cellulose (PASC) at pH 5.
Figure 4:
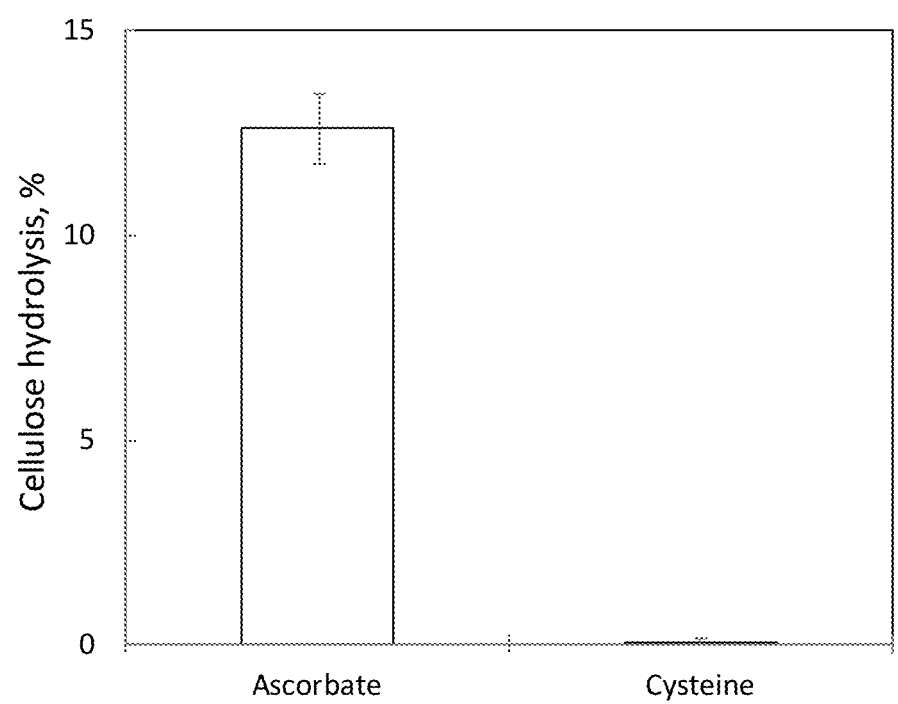
FIG. 4 shows the activity of *Lentinus similis* P247JK GH61 polypeptide in degrading phosphoric acid-swollen cellulose (PASC) at pH 5.
Figure 5:
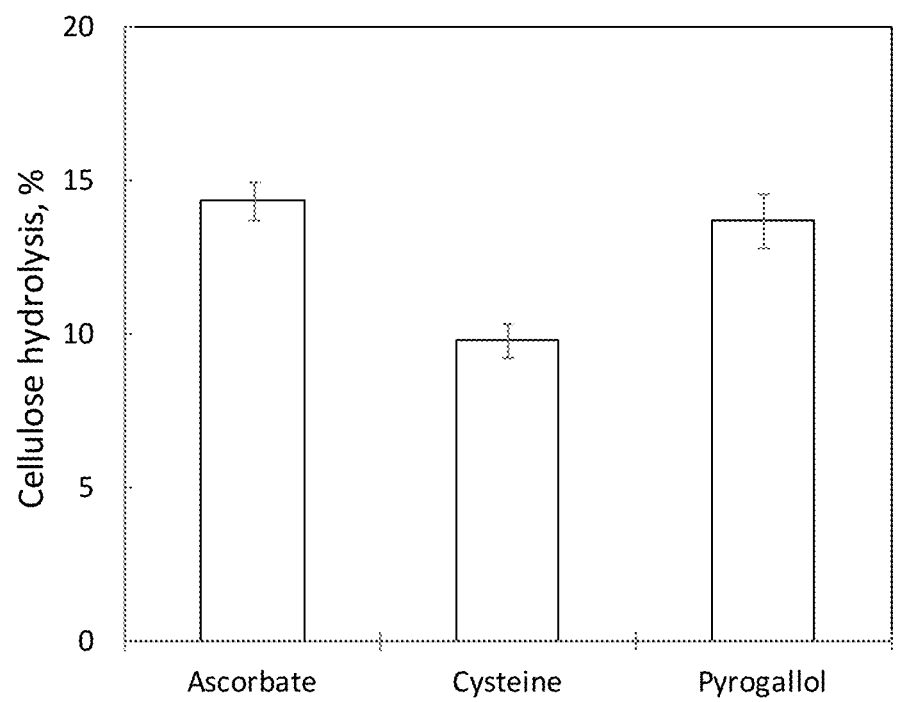
FIG. 5 shows the activity of *Lentinus similis* P247J6 GH61 polypeptide in degrading phosphoric acid-swollen cellulose (PASC) at pH 5.

The results are shown in FIGS. 3-5. FIGS. 3, 4, and 5 show the activity of the *Lentinus similis* P247JE, P247JK, and P247J6 GH61 polypeptide, respectively, in degrading phosphoric acid-swollen cellulose (PASC).

Example 16: Cloning of the P24NHZ GH61 Polypeptide Coding Sequence from *Bulgaria inquinans* O46TR The P24NHZ GH61 polypeptide coding sequence was cloned from *Bulgaria inquinans* O46TR genomic DNA by PCR.

*Bulgaria inquinans* O46TR was cultivated in 100 ml of YP+2% glucose medium in 1000 ml Erlenmeyer shake flasks for 5 days at 20° C. Mycelia were harvested from the flasks by filtration of the cultivation medium through a Buchner vacuum funnel lined with MIRACLOTH® (EMD Millipore, Billerica, Mass., USA). Mycelia were frozen in liquid nitrogen and stored at −80 C until further use. Genomic DNA was isolated using a DNEASY® Plant Maxi Kit according to the manufacturer's instructions.

Genomic sequence information was generated by Illumina HiSeq 2000 equipment at Fasteris SA, Switzerland, Plan-les-Ouates, Switzerland. Five µg of the isolated *Bulgaria inquinans* genomic DNA were sent to Fasteris for preparation and analysis and a 100 bp, paired end strategy was employed with a library insert size of 200-500 bp. One half of a HiSeq run was used for a total of 2×133,440,122 100 bp raw reads obtained. The reads were subsequently fractionated to 25% (leaving 2×33,360,030 reads) followed by trimming (extracting longest sub-sequences having Phred-scores of 10 or more). These reads were assembled using Idba version 0.18. Contigs shorter than 200 bp were discarded, resulting in 29,644,592 bp with an N-50 of 16,380. Genes were called using GeneMark.hmm ES version 2.3a and identification of the catalytic domain was made using "Glyco_hydro_61" Hidden Markov Model provided by Pfam. The P24NHZ GH61 polypeptide coding sequence for the entire coding region was cloned from *Bulgaria inquinans* genomic DNA by PCR using the primers shown below.

```
Primer KKSC0136-F:
                                       (SEQ ID NO: 19)
5'-ACACAACTGGGGATCCACCATGTCCACTTTGTTGGGCCT-3'

Primer KKSC0136-R:
                                       (SEQ ID NO: 20)
5'-AGATCTCGAGAAGCTTACTAAGCATCGCAGGTGTCGT-3'
```

Bold letters represent *Bulgaria inquinans* P24NHZ GH61 polypeptide coding sequence. Restriction sites are underlined. The sequence to the left of the restriction sites is homologous to the insertion sites of pDau109.

The amplification reaction (40 µl) was composed of 25 µl of 2× IPROOF™ HF Master Mix (Bio-Rad Laboratories, Inc., Hercules, Calif., USA), 1 µl of primer KKSC0136F (100 µM), 1 µl of primer KKSC0136R (100 µM), 1 µl of *Bulgaria inquinans* genomic DNA (100 ng/µl), and 22 µl of deionized water. The PCR reaction was incubated in a DYAD® Dual-Block Thermal Cycler (MJ Research Inc., Waltham, Mass., USA) programmed for 1 cycle at 98° C. for 30 seconds; 30 cycles each at 98° C. for 10 seconds, 55° C. for 20 seconds, and 72° C. for 30 seconds; and 1 cycle at 72°

C. for 10 minutes. Samples were cooled to 10° C. before removal and further processing.

Five µl of the PCR reaction were analyzed by 1% agarose gel electrophoresis using TAE buffer where a major band of about 1.1 kb was observed. The remaining PCR reaction was purified directly using an ILLUSTRA™ GFX™ PCR DNA and Gel Band Purification Kit according to the manufacturer's instructions.

Two µg of plasmid pDau109 were digested with Bam HI and Hind III and the digested plasmid was run on a 1% agarose gel using 50 mM Tris base-50 mM boric acid-1 mM disodium EDTA (TBE) buffer in order to remove the stuffer fragment from the restricted plasmid. The bands were visualized by the addition of SYBR® Safe DNA gel stain (Life Technologies Corporation, Grand Island, N.Y., USA) and use of a 470 nm wavelength transilluminator. The band corresponding to the restricted plasmid was excised and purified using an ILLUSTRA™ GFX™ PCR DNA and Gel Band Purification Kit. The plasmid was eluted into 10 mM Tris pH 8.0 and its concentration adjusted to 20 ng per µl. An IN-FUSION® PCR Cloning Kit was used to clone the 1170 bp PCR fragment into pDau109 digested with Bam HI and Hind III (20 ng). The IN-FUSION® total reaction volume was 10 µl. The IN-FUSION® reaction was transformed into FUSION-BLUE™ E. coli cells (Clontech Laboratories, Inc., Mountain View, Calif., USA) according to the manufacturer's protocol and spread onto LB agar plates supplemented with 50 µg of ampicillin per ml. After incubation overnight at 37° C., transformant colonies were observed growing under selection on the LB agar plates.

Several colonies were selected for analysis by colony PCR using the primers described below. Four colonies were transferred from the LB agar plates with a yellow inoculation pin (Nunc A/S, Denmark) to new LB agar plates supplemented with 50 µg of ampicillin per ml and incubated overnight at 37° C.

Primer 8653:
(SEQ ID NO: 21)
5'-GCAAGGGATGCCATGCTTGG-3'

Primer 8654:
(SEQ ID NO: 22)
5'-CATATAACCAATTGCCCTC-3'

Each of the four colonies were transferred directly into 200 µl PCR tubes composed of 6 µl of 2×HiFi RED-DYMIX™ PCR Master Mix (ThermoFisher Scientific, Rockford, Ill., USA), 0.5 µl of primer 8653 (10 pm/µl), 0.5 µl of primer 8654 (10 pm/µl), and 5 µl of deionized water. Each colony PCR was incubated in a DYAD® Dual-Block Thermal Cycler programmed for 1 cycle at 94° C. for 60 seconds; and 30 cycles each at 94° C. for 30 seconds, 55° C. for 30 seconds, 68° C. for 60 seconds, 68° C. for 10 minutes, and 10° C. for 10 minutes.

Four µl of each completed PCR reaction were submitted to 1% agarose gel electrophoresis using TAE buffer. All four E. coli transformants showed a PCR band of 1.1 kb. Plasmid DNA was isolated from each of the four colonies using a QIAPREP® Spin Miniprep Kit. The resulting plasmid DNA was sequenced with primers 8653 and 8654 using an Applied Biosystems Model 3730 Automated DNA Sequencer and version 3.1 BIG-DYE™ terminator chemistry (Applied Biosystems, Inc., Foster City, Calif., USA). The program Primer3 (SourceForge; http://primer3.sourceforge.net/releases.php) was used to design two internal primers for the coding region of P24NHZ to identify a plasmid free of sequencing errors.

Primer KKSC0136fw1:
(SEQ ID NO: 23)
5'-CACAGTGCAAGTAGCGAGGA-3'

Primer KKSC0136rw1:
(SEQ ID NO: 24)
5'-TCGCTACTTGCACTGTGGAG-3'

Combined with the vector primers 8653 and 8654, the spacing of the internal primers gave overlapping coverage of the entire open reading frame in both directions with an overlap coverage of 500 bp or less between primers. Reads were obtained from the ABI 3730 DNA sequencer used above and the nucleotide bases were called using the KB-basecaller (Applied Biosystems, Foster City, USA) that produces quality scores for the individual bases in the reads. All reads were assembled to a single sequence and phred-Phrap quality score (http://www.phrap.org).

One plasmid, pKKSC0136-1, in a colony designated E. coli KKSC136-1 was free of errors and chosen for expression.

Example 17: Expression of the P24NHZ GH61 Polypeptide Coding Sequence from Bulgaria inquinans O46TR A. oryzae MT3568 is an amdS (acetamidase) disrupted gene derivative of Aspergillus oryzae JaL355 (WO 2002/40694) in which pyrG auxotrophy was restored by inactivating the A. oryzae amdS gene. Protoplasts of A. oryzae MT3568 were prepared according to the method described in European Patent, EP0238023, pages 14-15.

E. coli KKSC136-1 containing pKKSC0136-1 was grown overnight according to the manufacturer's instructions (QIAGEN GMBH, Hilden Germany) and plasmid DNA of pKKSC0139-1 was isolated using a Plasmid Midi Kit (QIAGEN GMBH, Hilden Germany) according to the manufacturer's instructions. The purified plasmid DNA was transformed into Aspergillus oryzae MT3568 according to the method described in WO 2005/042735, pages 34-35. Briefly, 8 µl of plasmid DNA representing 3 µg of DNA were added to 100 µl of the A. oryzae MT3568 protoplasts. A 250 µl volume of 60% PEG solution was added and the tubes were gently mixed and incubated at 37° C. for 30 minutes. The mix was added to 10 ml of pre-melted COVE top agarose, which was melted and then temperature equilibrated to 40° C. in a warm water bath before being added to the protoplast mixture. The combined mixture was then spread onto two COVE sucrose plates containing 10 mM acetamide. The plates were incubated at 37° C. for 4 days. Single A. oryzae transformed colonies were identified by growth on acetamide as a carbon source. Four A. oryzae transformants were isolated and inoculated into 750 µl of YP+2% glucose medium, 750 µl of YP+2% maltodextrin medium, and DAP4C medium in 96 well deep plates and incubated at 37° C. stationary for 4 days. At the same time the four transformants were restreaked on COVE-2 plates.

Culture broth from the Aspergillus oryzae transformants were then analyzed for production of the P24GAB GH61 polypeptide by SDS-PAGE using NUPAGE® 10% Bis-Tris SDS gels (Invitrogen, Carlsbad, Calif., USA) according to the manufacturer. A band at approximately 60 kDa was observed for each of the Aspergillus oryzae transformants.

One *A. oryzae* transformant producing the P24NHZ GH61 polypeptide was designated *A. oryzae* EXP08201.

Alternatively, a synthetic gene based on the nucleotide sequence identified as SEQ ID NO: 7 can be obtained from a number of vendors such as Gene Art (GENEART AG BioPark, Josef-Engert-Str. 11, 93053, Regensburg, Germany) or DNA 2.0 (DNA2.0, 1430 O'Brien Drive, Suite E, Menlo Park, Calif. 94025, USA). The synthetic gene can be designed to incorporate additional DNA sequences such as restriction sites or homologous recombination regions to facilitate cloning into an expression vector.

Using the two synthetic oligonucleotide primers KKSC0136-F and KKSC0136-R described above, a simple PCR reaction can be used to amplify the full-length open reading frame from the synthetic gene of SEQ ID NO: 7. The gene can then be cloned into an expression vector as described herein and expressed in a host cell as described herein, e.g., *Aspergillus oryzae*.

Example 18: Characterization of the P24NHZ GH61 Polypeptide Coding Sequence from *Bulgaria inquinans* O46TR The genomic DNA sequence and deduced amino acid sequence of the *Bulgaria inquinans* P24NHZ GH61 polypeptide coding sequence are shown in SEQ ID NO: 7 and SEQ ID NO: 8, respectively. The coding sequence is 969 bp including the stop codon with no intervening introns. The encoded predicted protein is 322 amino acids. Using the SignalP 3.0 program (Bendtsen et al., 2004, supra), a signal peptide of 16 residues was predicted. The SignalP prediction is in accord with the necessity for having a histidine reside at the N-terminus in order for proper metal binding and hence protein function to occur (See Harris et al., 2010, supra, and Quinlan et al., 2011, supra). The predicted mature protein contains 306 amino acids with a predicted molecular mass of 31 kDa and a predicted isoelectric point of 3.68. An unusual C terminal extension is observed at positions 243 to 319 in the GH61 polypeptide. This extension is not part of the GH61 enzyme module.

A comparative pairwise global alignment of amino acid sequences was determined using the Needleman and Wunsch algorithm (Needleman and Wunsch, 1970, supra) with a gap open penalty of 10, a gap extension penalty of 0.5, and the EBLOSUM62 matrix. The alignment showed that the deduced amino acid sequence of the *Bulgaria inquinans* genomic DNA encoding the P24NHZ GH61 polypeptide shares 63.82% identity to (excluding gaps) to the deduced amino acid sequence of a GH61 polypeptide from *Acremonium cellulolyticus* (GENESEQP:AZF55171).

Example 19: Preparation of *Bulgaria inquinans* GH61 Polypeptide

*Aspergillus oryzae* EXP08201 was cultivated in 1000 ml Erlenmeyer shake flasks containing 100 ml of YP+2% glucose medium at 26° C. for 4 days with agitation at 85 rpm. The broth was filtered using a 0.22 μm EXPRESS™ Plus Membrane (Millipore, Bedford, Mass., USA). A 100 ml volume of the filtered broth was concentrated to about 10 ml using VIVASPIN® 20 (10 kDa MWCO) spin concentrators and centrifuging (Sorvall, Legend RT+Centrifuge, Thermo Scientific, Germany) at 3000 rpm for 15 minute intervals repeatedly. The total protein content of the GH61 polypeptide was determined by gel quantitation following quantitative desalting. A 3 ml volume of the concentrated GH61 polypeptide broth was desalted and buffer exchanged into 50 mM sodium acetate pH 5.0 using an ECONO-PAC® 10-DG desalting column (Bio-Rad Laboratories, Inc., Hercules, Calif., USA). Protein concentration was determined by SDS-PAGE using an 8-16% Tris HCl CRITERION STAIN FREE™ gel (Bio-Rad Laboratories, Inc., Hercules, Calif., USA) and a CRITERION STAIN FREE™ Imaging System (Bio-Rad Laboratories, Inc., Hercules, Calif., USA).

Example 20: Effect of the *Bulgaria inquinans* GH61 Polypeptide on the Hydrolysis of Microcrystalline Cellulose The *Bulgaria inquinans* GH61 polypeptide was evaluated for the ability to enhance the hydrolysis of microcrystalline cellulose by *Trichoderma reesei* GH5 endoglucanase II (loaded at 2 mg protein per g cellulose) and *Aspergillus fumigatus* GH3 beta-glucosidase (loaded at 2 mg protein per g cellulose) with and without the addition of 20 mM catechol at 50° C. The *B. inquinans* GH61 polypeptide was added at 5 mg protein per g cellulose. The composition of *T. reesei* GH5 endoglucanase II (loaded at 2 mg protein per g cellulose) and *A. fumigatus* GH3 beta-glucosidase (loaded at 2 mg protein per g cellulose) was also run as a control without added GH61 polypeptide.

The assay was performed as described in Example 11. The 1 ml reactions with microcrystalline cellulose were conducted for 72 hours in 50 mM ammonium acetate pH 5.0 containing 10 μM copper sulfate. All reactions were performed in triplicate and involved single mixing at the beginning of hydrolysis.

Figure 6:
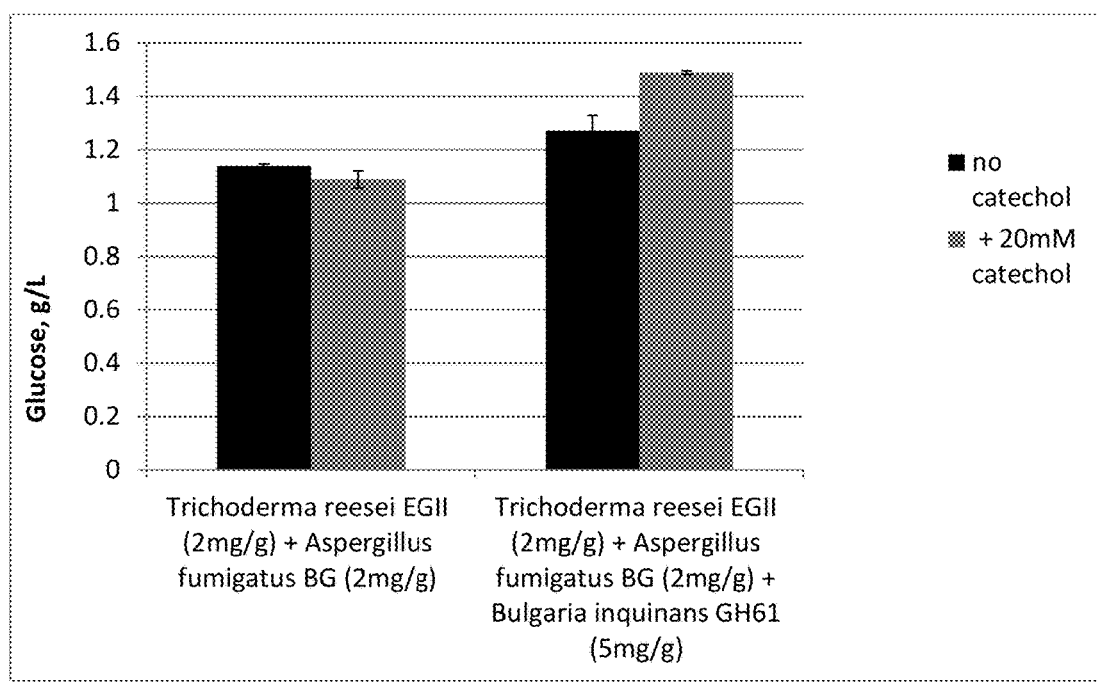
FIG. 6 shows the effect of the *Bulgaria inquinans* GH61 polypeptide on the hydrolysis of microcrystalline cellulose by a composition of *Trichoderma reesei* GH5 endoglucanase II and *Aspergillus fumigatus* GH3 beta-glucosidase.

As shown in FIG. 6, hydrolysis of the microcrystalline cellulose by the composition of *T. reesei* GH5 endoglucanase II and *A. fumigatus* GH3 beta-glucosidase without catechol produced similar results as that obtained with the *B. inquinans* GH61 polypeptide added to the composition of *T. reesei* GH5 endoglucanase II and *A. fumigatus* GH3 beta-glucosidase without catechol. The addition of *B. inquinans* GH61 polypeptide to the composition of *T. reesei* GH5 endoglucanase II and *A. fumigatus* GH3 beta-glucosidase without catechol did not improve hydrolysis of the microcrystalline cellulose. However, as shown in FIG. 6, the addition of *B. inquinans* GH61 polypeptide to the composition of *T. reesei* GH5 endoglucanase II and *A. fumigatus* GH3 beta-glucosidase with 20 mM catechol resulted in a higher degree of glucose production (shown in g/L) compared to the addition of *B. inquinans* GH61 polypeptide to the composition of *T. reesei* GH5 endoglucanase II and *A. fumigatus* GH3 beta-glucosidase without added catechol and compared to the composition of *T. reesei* GH5 endoglucanase II and *A. fumigatus* GH3 beta-glucosidase without GH61 polypeptide and without added catechol. The results demonstrated a 1.17-fold improvement (or 17% increase) in hydrolysis of the microcrystalline cellulose by *B. inquinans* GH61 polypeptide addition to the composition of *T. reesei* GH5 endoglucanase II and *A. fumigatus* GH3 beta-glucosidase with catechol compared to without catechol.

Example 21: Pretreated Corn Stover Hydrolysis Assay

Corn stover was pretreated at the U.S. Department of Energy National Renewable Energy Laboratory (NREL) using 1.4 wt. % sulfuric acid at 165° C. and 107 psi for 8 minutes. The water-insoluble solids in the pretreated corn stover (PCS) contained 56.5% cellulose, 4.6% hemicellulose and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003.

Unmilled, unwashed PCS (whole slurry PCS) was prepared by adjusting the pH of the PCS to 5.0 by addition of 10 M NaOH with extensive mixing, and then autoclaving for 20 minutes at 120° C. The dry weight of the whole slurry PCS was 29%. Milled unwashed PCS (dry weight 32.35%) was prepared by milling whole slurry PCS in a Cosmos ICMG 40 wet multi-utility grinder (EssEmm Corporation, Tamil Nadu, India).

The hydrolysis of PCS was conducted using 2.2 ml deep-well plates (Axygen, Union City, Calif., USA) in a total reaction volume of 1.0 ml. The hydrolysis was performed with 50 mg of insoluble PCS solids per ml of 50 mM sodium acetate pH 5.0 buffer containing 1 mM manganese sulfate and various protein loadings of various enzyme compositions (expressed as mg protein per gram of cellulose). Enzyme compositions were prepared and then added simultaneously to all wells in a volume ranging from 50 µl to 200 µl, for a final volume of 1 ml in each reaction. The plate was then sealed using an ALPS-300™ plate heat sealer, mixed thoroughly, and incubated at a specific temperature for 72 hours. All experiments reported were performed in triplicate.

Following hydrolysis, samples were filtered using a 0.45 µm MULTISCREEN® 96-well filter plate and the filtrates were analyzed for sugar content as described below. When not used immediately, filtered aliquots were frozen at −20° C. The glucose concentration of the samples diluted in 0.005 M $H_2SO_4$ was measured using a 4.6×250 mm AMINEX® HPX-87H column by elution with 0.05% w/w benzoic acid-0.005 M $H_2SO_4$ at 65° C. at a flow rate of 0.6 ml per minute, and quantitation by integration of the glucose signal from refractive index detection (CHEMSTATION®, AGILENT® 1100 HPLC) calibrated by a pure glucose standard. The resultant glucose equivalents were used to calculate the percentage of cellulose conversion for each reaction.

The measured glucose concentrations were adjusted for the appropriate dilution factor. The net concentrations of enzymatically-produced glucose from the milled unwashed PCS were determined by adjusting the measured glucose concentrations for corresponding background glucose concentrations in unwashed PCS at a zero time point. All HPLC data processing was performed using MICROSOFT EXCEL™ software.

The degree of cellulose conversion to glucose was calculated using the following equation: % conversion=(glucose concentration/glucose concentration in a limit digest)× 100. In order to calculate % conversion, a 100% conversion point was set based on a cellulase control (100 mg of Trichoderma reesei cellulase per gram cellulose), and all values were divided by this number and then multiplied by 100. Triplicate data points were averaged and standard deviation was calculated.

Example 22: Preparation of an Enzyme Composition

The *Aspergillus fumigatus* GH7A cellobiohydrolase I (SEQ ID NO: 25 [DNA sequence] and SEQ ID NO: 26 [deduced amino acid sequence]) was prepared recombinantly in *Aspergillus oryzae* as described in WO 2011/057140. The filtered broth of the *A. fumigatus* cellobiohydrolase I was concentrated and buffer exchanged using a tangential flow concentrator (Pall Filtron, Northborough, Mass., USA) equipped with a 10 kDa polyethersulfone membrane (Pall Filtron, Northborough, Mass., USA) with 20 mM Tris-HCl pH 8.0. The desalted broth of the *A. fumigatus* cellobiohydrolase I was loaded onto a Q SEPHAROSE® ion exchange column (GE Healthcare, Piscataway, N.J., USA) equilibrated in 20 mM Tris-HCl pH 8 and eluted using a linear 0 to 1 M NaCl gradient. Fractions were collected and fractions containing the cellobiohydrolase I were pooled based on SDS-PAGE analysis using 8-16% CRITERION® Stain-free SDS-PAGE gels (Bio-Rad Laboratories, Inc., Hercules, Calif., USA).

The *Aspergillus fumigatus* GH6A cellobiohydrolase II (SEQ ID NO: 27 [DNA sequence] and SEQ ID NO: 28 [deduced amino acid sequence]) was prepared recombinantly in *Aspergillus oryzae* as described in WO 2011/057140. The filtered broth of the *A. fumigatus* cellobiohydrolase II was buffer exchanged into 20 mM Tris pH 8.0 using a 400 ml SEPHADEX™ G-25 column (GE Healthcare, United Kingdom). The fractions were pooled and adjusted to 1.2 M ammonium sulphate-20 mM Tris pH 8.0. The equilibrated protein was loaded onto a PHENYL SEPHAROSE™ 6 Fast Flow column (high sub) (GE Healthcare, Piscataway, N.J., USA) equilibrated in 20 mM Tris pH 8.0 with 1.2 M ammonium sulphate, and bound proteins were eluted with 20 mM Tris pH 8.0 with no ammonium sulphate. The fractions were pooled.

The *Trichoderma reesei* GH5 endoglucanase II was prepared as described in Example 9.

The *Aspergillus fumigatus* GH10 xylanase (xyn3) (SEQ ID NO: 29 [DNA sequence] and SEQ ID NO: 30 [deduced amino acid sequence]) was prepared recombinantly according to WO 2006/078256 using *Aspergillus oryzae* BECh2 (WO 2000/39322) as a host. The filtered broth of the *A. fumigatus* xylanase was desalted and buffer-exchanged into 50 mM sodium acetate pH 5.0 using a HIPREP® 26/10 Desalting Column (GE Healthcare, Piscataway, N.J., USA).

The *Aspergillus fumigatus* NN055679 Cel3A beta-glucosidase was prepared as described in Example 10.

The *Aspergillus fumigatus* NN051616 GH3 beta-xylosidase (SEQ ID NO: 31 [DNA sequence] and SEQ ID NO: 32 [deduced amino acid sequence]) was prepared recombinantly in *Aspergillus oryzae* as described in WO 2011/057140. The filtered broth of the *A. fumigatus* beta-xylosidase was desalted and buffer-exchanged into 50 mM sodium acetate pH 5.0 using a HIPREP® 26/10 Desalting Column.

The protein concentration for each of the monocomponents described above was determined using a Microplate BCA™ Protein Assay Kit in which bovine serum albumin was used as a protein standard. An enzyme composition was prepared composed of each monocomponent as follows: 37% *Aspergillus fumigatus* Cel7A cellobiohydrolase I, 25% *Aspergillus fumigatus* Cel6A cellobiohydrolase II, 10% *Trichoderma reesei* GH5 endoglucanase II, 5% *Aspergillus fumigatus* GH10 xylanase, 5% *Aspergillus fumigatus* beta-glucosidase, and 3% *Aspergillus fumigatus* beta-xylosidase. The enzyme composition is designated herein as "cellulolytic enzyme composition".

Example 23: Effect of the *Bulgaria inquinans* GH61 Polypeptide on the Hydrolysis of Milled Unwashed PCS by a Cellulolytic Enzyme Composition The *Bulgaria inquinans* GH61 polypeptide was evaluated for the ability to enhance the hydrolysis of milled unwashed PCS (Example 21) by the cellulolytic enzyme composition (Example 22) at 2.55 mg total protein per g cellulose at 50° C., 55° C., 60° C., and 65° C. The *Bulgaria inquinans* GH61 polypeptide was added at 0.45 mg protein per g cellulose. The cellulolytic enzyme composition was also run without added GH61 polypeptide at 3.0 mg protein per g cellulose.

The assay was performed as described in Example 21. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

Figure 7:
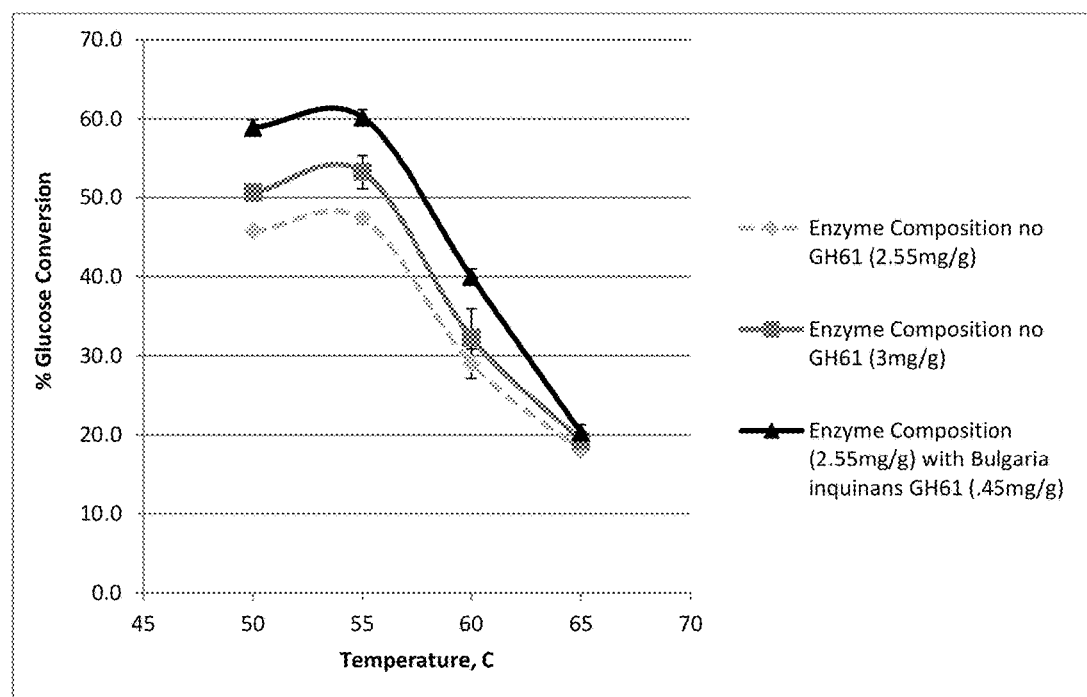
FIG. 7 shows the effect of the *Bulgaria inquinans* GH61 polypeptide on the hydrolysis of milled unwashed pretreated corn stover (PCS) by a cellulolytic enzyme composition.

As shown in FIG. 7, the cellulolytic enzyme composition that included the *B. inquinans* GH61 polypeptide significantly outperformed the cellulolytic enzyme composition (2.55 mg protein per g cellulose and 3.0 mg protein per g cellulose) without GH61 polypeptide. The degree of cellulose conversion to glucose for the *B. inquinans* GH61 polypeptide added to the cellulolytic enzyme composition was significantly higher than the cellulolytic enzyme composition without added GH61 polypeptide at 50° C., 55° C., 60° C., and 65° C., especially at 50° C., 55° C., and 60° C.

The present invention is further described by the following numbered paragraphs:

[1] An isolated polypeptide having cellulolytic enhancing activity, selected from the group consisting of: (a) a polypeptide having at least 60% sequence identity to the mature polypeptide of SEQ ID NO: 6, at least 65% sequence identity to the mature polypeptide of SEQ ID NO: 8, at least 75% sequence identity to the mature polypeptide of SEQ ID NO: 2, or at least 80% sequence identity to the mature polypeptide of SEQ ID NO: 4; (b) a polypeptide encoded by a polynucleotide that hybridizes under at least high stringency conditions with the mature polypeptide coding sequence of SEQ ID NO: 1 or the cDNA sequence thereof, the mature polypeptide of SEQ ID NO: 3 or the cDNA sequence thereof, the mature polypeptide of SEQ ID NO: 5 or the cDNA sequence thereof, or the mature polypeptide of SEQ ID NO: 7; or the full-length complement thereof; (c) a polypeptide encoded by a polynucleotide having at least 60% sequence identity to the mature polypeptide coding sequence of SEQ ID NO: 5 or the cDNA sequence thereof, at least 65% sequence identity to the mature polypeptide coding sequence of SEQ ID NO: 7, at least 75% sequence identity to the mature polypeptide coding sequence of SEQ ID NO: 1 or the cDNA sequence thereof, or at least 80% sequence identity to the mature polypeptide coding sequence of SEQ ID NO: 3 or the cDNA sequence thereof; (d) a variant of the mature polypeptide of SEQ ID NO: 2, SEQ ID NO: 4, SEQ ID NO: 6, or SEQ ID NO: 8 comprising a substitution, deletion, and/or insertion at one or more positions; and (e) a fragment of the polypeptide of (a), (b), (c), or (d) that has cellulolytic enhancing activity.

[2] The polypeptide of paragraph 1, having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 6; at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 8; at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2; or at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4.

[3] The polypeptide of paragraph 1, which is encoded by a polynucleotide that hybridizes under high or very high stringency conditions with the mature polypeptide coding sequence of SEQ ID NO: 1 or the cDNA sequence thereof, the mature polypeptide coding sequence of SEQ ID NO: 3 or the cDNA sequence thereof, the mature polypeptide coding sequence of SEQ ID NO: 5 or the cDNA sequence thereof, or the mature polypeptide coding sequence of SEQ ID NO: 7; or the full-length complement thereof.

[4] The polypeptide of paragraph 1, which is encoded by a polynucleotide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5 or the cDNA sequence thereof; at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 7; at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1 or the cDNA sequence thereof; or at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 3 or the cDNA sequence thereof.

[5] The polypeptide of any of paragraphs 1-4, comprising or consisting of SEQ ID NO: 2, SEQ ID NO: 4, SEQ ID NO: 6, or SEQ ID NO: 8 or the mature polypeptide of SEQ ID NO: 2, SEQ ID NO: 4, SEQ ID NO: 6, or SEQ ID NO: 8.

[6] The polypeptide of paragraph 5, wherein the mature polypeptide is amino acids 20 to 316 of SEQ ID NO: 2, amino acids 20 to 231 of SEQ ID NO: 4, amino acids 20 to 254 of SEQ ID NO: 6, or amino acids 17 to 322 of SEQ ID NO: 8.

[7] The polypeptide of paragraph 1, which is a variant of the mature polypeptide of SEQ ID NO: 2, SEQ ID NO: 4, SEQ ID NO: 6, or SEQ ID NO: 8 comprising a substitution, deletion, and/or insertion at one or more positions.

[8] The polypeptide of any of paragraphs 1-7, which is a fragment of SEQ ID NO: 2, SEQ ID NO: 4, SEQ ID NO: 6, or SEQ ID NO: 8, wherein the fragment has cellulolytic enhancing activity.

[9] An isolated polypeptide comprising a catalytic domain selected from the group consisting of: (a) a catalytic domain having at least 80% sequence identity to amino acids 20 to 245 of SEQ ID NO: 2; (b) a catalytic domain encoded by a polynucleotide that hybridizes under at least very high stringency conditions with nucleotides 58 to 1122 of SEQ ID NO: 1; the cDNA sequence thereof; or the full-length complement thereof; (c) a catalytic domain encoded by a polynucleotide having at least 80% sequence identity to nucleotides 58 to 1122 of SEQ ID NO: 1 or the cDNA sequence thereof; (d) a variant of amino acids 20 to 245 of SEQ ID NO: 2 comprising a substitution, deletion, and/or insertion at one or more positions; and (e) a fragment of the catalytic domain of (a), (b), (c), or (d) that has cellulolytic enhancing activity.

[10] The polypeptide of paragraph 9, further comprising a cellulose binding domain.

[11] An isolated polypeptide comprising a cellulose binding domain operably linked to a catalytic domain, wherein the binding domain is selected from the group consisting of: (a) a cellulose binding domain having at least 80% sequence identity to amino acids 284 to 316 of SEQ ID NO: 2; (b) a cellulose binding domain encoded by a polynucleotide that hybridizes under at least very high stringency conditions with nucleotides 1237 to 1458 of SEQ ID NO: 1; the cDNA sequence thereof; or the full-length complement thereof; (c) a cellulose binding domain encoded by a polynucleotide having at least 80% sequence identity to nucleotides 1237 to 1458 of SEQ ID NO: 1 or the cDNA sequence thereof; (d) a variant of amino acids 284 to 316 of SEQ ID NO: 2 comprising a substitution, deletion, and/or insertion at one or more positions; and (e) a fragment of the cellulose binding domain of (a), (b), (c), or (d) that has binding activity.

[12] The polypeptide of paragraph 11, wherein the catalytic domain is obtained from a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

[13] A composition comprising the polypeptide of any of paragraphs 1-12.

[14] An isolated polynucleotide encoding the polypeptide of any of paragraphs 1-12.

[15] A nucleic acid construct or expression vector comprising the polynucleotide of paragraph 14 operably linked to one or more control sequences that direct the production of the polypeptide in an expression host.

[16] A recombinant host cell comprising the polynucleotide of paragraph 14 operably linked to one or more control sequences that direct the production of the polypeptide.

[17] A method of producing the polypeptide of any of paragraphs 1-12, comprising: cultivating a cell, which in its wild-type form produces the polypeptide, under conditions conducive for production of the polypeptide.

[18] The method of paragraph 17, further comprising recovering the polypeptide.

[19] A method of producing a polypeptide having cellulolytic enhancing activity, comprising: cultivating the host cell of paragraph 16 under conditions conducive for production of the polypeptide.

[20] The method of paragraph 19, further comprising recovering the polypeptide.

[21] A transgenic plant, plant part or plant cell transformed with a polynucleotide encoding the polypeptide of any of paragraphs 1-12.

[22] A method of producing a polypeptide having cellulolytic enhancing activity, comprising: cultivating the transgenic plant or plant cell of paragraph 21 under conditions conducive for production of the polypeptide.

[23] The method of paragraph 22, further comprising recovering the polypeptide.

[24] A method of producing a mutant of a parent cell, comprising inactivating a polynucleotide encoding the polypeptide of any of paragraphs 1-12, which results in the mutant producing less of the polypeptide than the parent cell.

[25] A mutant cell produced by the method of paragraph 24.

[26] The mutant cell of paragraph 25, further comprising a gene encoding a native or heterologous protein.

[27] A method of producing a protein, comprising: cultivating the mutant cell of paragraph 25 or 26 under conditions conducive for production of the protein.

[28] The method of paragraph 27, further comprising recovering the protein.

[29] A double-stranded inhibitory RNA (dsRNA) molecule comprising a subsequence of the polynucleotide of paragraph 14, wherein optionally the dsRNA is an siRNA or an miRNA molecule.

[30] The double-stranded inhibitory RNA (dsRNA) molecule of paragraph 29, which is about 15, 16, 17, 18, 19, 20, 21, 22, 23, 24, 25 or more duplex nucleotides in length.

[31] A method of inhibiting the expression of a polypeptide having cellulolytic enhancing activity in a cell, comprising administering to the cell or expressing in the cell the double-stranded inhibitory RNA (dsRNA) molecule of paragraph 29 or 30.

[32] A cell produced by the method of paragraph 31.

[33] The cell of paragraph 32, further comprising a gene encoding a native or heterologous protein.

[34] A method of producing a protein, comprising: cultivating the cell of paragraph 32 or 33 under conditions conducive for production of the protein.

[35] The method of paragraph 35, further comprising recovering the protein.

[36] An isolated polynucleotide encoding a signal peptide comprising or consisting of amino acids 1 to 19 of SEQ ID NO: 2, amino acids 1 to 19 of SEQ ID NO: 4, amino acids 1 to 19 of SEQ ID NO: 6, or amino acids 1 to 16 of SEQ ID NO: 8.

[37] A nucleic acid construct or expression vector comprising a gene encoding a protein operably linked to the polynucleotide of paragraph 36, wherein the gene is foreign to the polynucleotide encoding the signal peptide.

[38] A recombinant host cell comprising a gene encoding a protein operably linked to the polynucleotide of paragraph 36, wherein the gene is foreign to the polynucleotide encoding the signal peptide.

[39] A method of producing a protein, comprising: cultivating a recombinant host cell comprising a gene encoding a protein operably linked to the polynucleotide of paragraph 36, wherein the gene is foreign to the polynucleotide encoding the signal peptide, under conditions conducive for production of the protein.

[40] The method of paragraph 39, further comprising recovering the protein.

[41] A process for degrading a cellulosic material, comprising: treating the cellulosic material with an enzyme composition in the presence of the polypeptide having cellulolytic enhancing activity of any of paragraphs 1-12.

[42] The process of paragraph 41, wherein the cellulosic material is pretreated.

[43] The process of paragraph 41 or 42, wherein the enzyme composition comprises one or more enzymes selected from the group consisting of a cellulase, a polypeptide having cellulolytic enhancing activity, a hemicellulase, a CIP, an esterase, an expansin, a laccase, a ligninolytic enzyme, a pectinase, a peroxidase, a protease, and a swollenin.

[44] The process of paragraph 43, wherein the cellulase is one or more enzymes selected from the group consisting of an endoglucanase, a cellobiohydrolase, and a beta-glucosidase.

[45] The process of paragraph 43, wherein the hemicellulase is one or more enzymes selected from the group consisting of a xylanase, an acetylxylan esterase, a feruloyl esterase, an arabinofuranosidase, a xylosidase, and a glucuronidase.

[46] The process of any of paragraphs 41-45, further comprising recovering the degraded cellulosic material.

[47] The process of paragraph 46, wherein the degraded cellulosic material is a sugar.

[48] The process of paragraph 47, wherein the sugar is selected from the group consisting of glucose, xylose, mannose, galactose, and arabinose.

[49] A process for producing a fermentation product, comprising: (a) saccharifying a cellulosic material with an enzyme composition in the presence of the polypeptide having cellulolytic enhancing activity of any of paragraphs 1-12; (b) fermenting the saccharified cellulosic material with one or more fermenting microorganisms to produce the fermentation product; and (c) recovering the fermentation product from the fermentation.

[50] The process of paragraph 49, wherein the cellulosic material is pretreated.

[51] The process of paragraph 49 or 50, wherein the enzyme composition comprises the enzyme composition comprises one or more enzymes selected from the group consisting of a cellulase, a polypeptide having cellulolytic enhancing activity, a hemicellulase, a CIP, an esterase, an expansin, a laccase, a ligninolytic enzyme, a pectinase, a peroxidase, a protease, and a swollenin.

[52] The process of paragraph 51, wherein the cellulase is one or more enzymes selected from the group consisting of an endoglucanase, a cellobiohydrolase, and a beta-glucosidase.

[53] The process of paragraph 51, wherein the hemicellulase is one or more enzymes selected from the group consisting of a xylanase, an acetylxylan esterase, a feruloyl esterase, an arabinofuranosidase, a xylosidase, and a glucuronidase.

[54] The process of any of paragraphs 49-53, wherein steps (a) and (b) are performed simultaneously in a simultaneous saccharification and fermentation.

[55] The process of any of paragraphs 49-54, wherein the fermentation product is an alcohol, an alkane, a cycloalkane, an alkene, an amino acid, a gas, isoprene, a ketone, an organic acid, or polyketide.

[56] A process of fermenting a cellulosic material, comprising: fermenting the cellulosic material with one or more fermenting microorganisms, wherein the cellulosic material is saccharified with an enzyme composition in the presence of the polypeptide having cellulolytic enhancing activity of any of paragraphs 1-12.

[57] The process of paragraph 56, wherein the fermenting of the cellulosic material produces a fermentation product.

[58] The process of paragraph 57, further comprising recovering the fermentation product from the fermentation.

[59] The process of paragraph 57 or 58, wherein the fermentation product is an alcohol, an alkane, a cycloalkane, an alkene, an amino acid, a gas, isoprene, a ketone, an organic acid, or polyketide.

[60] The process of any of paragraphs 56-59, wherein the cellulosic material is pretreated before saccharification.

[61] The process of any of paragraphs 56-60, wherein the enzyme composition comprises one or more enzymes selected from the group consisting of a cellulase, a polypeptide having cellulolytic enhancing activity, a hemicellulase, a CIP, an esterase, an expansin, a laccase, a ligninolytic enzyme, a pectinase, a peroxidase, a protease, and a swollenin.

[62] The process of paragraph 61, wherein the cellulase is one or more enzymes selected from the group consisting of an endoglucanase, a cellobiohydrolase, and a beta-glucosidase.

[63] The process of paragraph 61, wherein the hemicellulase is one or more enzymes selected from the group consisting of a xylanase, an acetylxylan esterase, a feruloyl esterase, an arabinofuranosidase, a xylosidase, and a glucuronidase.

[64] A whole broth formulation or cell culture composition comprising the polypeptide of any of paragraphs 1-12.

The invention described and claimed herein is not to be limited in scope by the specific aspects herein disclosed, since these aspects are intended as illustrations of several aspects of the invention. Any equivalent aspects are intended to be within the scope of this invention.

Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A nucleic acid construct, comprising a polynucleotide encoding a GH61 polypeptide having cellulolytic enhancing activity, wherein the polynucleotide is operably linked to one or more heterologous control sequences that direct the production of the GH61 polypeptide in a recombinant host cell, and wherein the GH61 polypeptide having cellulolytic enhancing activity is selected from the group consisting of:
   (a) a GH61 polypeptide having at least 95% sequence identity to the mature polypeptide of SEQ ID NO: 4;
   (b) a GH61 polypeptide encoded by a polynucleotide that hybridizes under very high stringency conditions with the full-length complement of the mature polypeptide coding sequence of SEQ ID NO: 3 or the cDNA sequence of the mature polypeptide coding sequence of SEQ ID NO: 3, wherein the very high stringency conditions are defined as prehybridization and hybridization at 42° C. in 5×SSPE, 0.3% SDS, 200 micrograms/ml sheared and denatured salmon sperm DNA, and 50% formamide, for 12 to 24 hours, and washing three times each for 15 minutes using 2×SSC, 0.2% SDS at 70° C.; and
(c) a GH61 polypeptide encoded by a polynucleotide having at least 99% sequence identity to the mature polypeptide coding sequence of SEQ ID NO: 3 or the cDNA sequence of the mature polypeptide coding sequence of SEQ ID NO: 3.

2. The nucleic acid construct of claim 1, wherein the GH61 polypeptide has at least 95% sequence identity to the mature polypeptide of SEQ ID NO: 4.

3. The nucleic acid construct of claim 1, wherein the GH61 polypeptide has at least 96% sequence identity to the mature polypeptide of SEQ ID NO: 4.

4. The nucleic acid construct of claim 1, wherein the GH61 polypeptide has at least 97% sequence identity to the mature polypeptide of SEQ ID NO: 4.

5. The nucleic acid construct of claim 1, wherein the GH61 polypeptide has at least 98% sequence identity to the mature polypeptide of SEQ ID NO: 4.

6. The nucleic acid construct of claim 1, wherein the GH61 polypeptide has at least 99% sequence identity to the mature polypeptide of SEQ ID NO: 4.

7. The nucleic acid construct of claim 1, wherein the GH61 polypeptide comprises SEQ ID NO: 4 or the mature polypeptide of SEQ ID NO: 4.

8. The nucleic acid construct of claim 1, wherein the GH61 polypeptide comprises amino acids 20 to 231 of SEQ ID NO: 4.

9. A recombinant host cell transformed with the nucleic acid construct of claim 1.

10. A method of producing a GH61 polypeptide having cellulolytic enhancing activity, comprising: (a) cultivating the recombinant host cell of claim 9 under conditions conducive for production of the polypeptide, and optionally (b) recovering the polypeptide.

11. A recombinant host cell, transformed with a nucleic acid construct comprising a polynucleotide encoding a GH61 polypeptide having cellulolytic enhancing activity, wherein the polynucleotide is operably linked to one or more control sequences that direct the production of the GH61 polypeptide in the recombinant host cell, wherein the GH61 polypeptide having cellulolytic enhancing activity is heterologous to the recombinant host cell, and wherein the GH61 polypeptide having cellulolytic enhancing activity is selected from the group consisting of:
(a) a GH61 polypeptide having at least 95% sequence identity to the mature polypeptide of SEQ ID NO: 4;
(b) a GH61 polypeptide encoded by a polynucleotide that hybridizes under very high stringency conditions with the full-length complement of the mature polypeptide coding sequence of SEQ ID NO: 3 or the cDNA sequence of the mature polypeptide coding sequence of SEQ ID NO: 3, wherein the very high stringency conditions are defined as prehybridization and hybridization at 42° C. in 5×SSPE, 0.3% SDS, 200 micrograms/ml sheared and denatured salmon sperm DNA, and 50% formamide, for 12 to 24 hours, and washing three times each for 15 minutes using 2×SSC, 0.2% SDS at 70° C.; and
(c) a GH61 polypeptide encoded by a polynucleotide having at least 99% sequence identity to the mature polypeptide coding sequence of SEQ ID NO: 3 or the cDNA sequence of the mature polypeptide coding sequence of SEQ ID NO: 3.

12. The recombinant host cell of claim 11, wherein the GH61 polypeptide has at least 95% sequence identity to the mature polypeptide of SEQ ID NO: 4.

13. The recombinant host cell of claim 11, wherein the GH61 polypeptide has at least 96% sequence identity to the mature polypeptide of SEQ ID NO: 4.

14. The recombinant host cell of claim 11, wherein the GH61 polypeptide has at least 97% sequence identity to the mature polypeptide of SEQ ID NO: 4.

15. The recombinant host cell of claim 11, wherein the GH61 polypeptide has at least 98% sequence identity to the mature polypeptide of SEQ ID NO: 4.

16. The recombinant host cell of claim 11, wherein the GH61 polypeptide has at least 99% sequence identity to the mature polypeptide of SEQ ID NO: 4.

17. The recombinant host cell of claim 11, wherein the GH61 polypeptide comprises SEQ ID NO: 4 or the mature polypeptide of SEQ ID NO: 4.

18. The recombinant host cell of claim 11, wherein the GH61 polypeptide comprises amino acids 20 to 231 of SEQ ID NO: 4.

19. A method of producing a GH61 polypeptide having cellulolytic enhancing activity, comprising: (a) cultivating the recombinant host cell of claim 11 under conditions conducive for production of the polypeptide, and optionally (b) recovering the polypeptide.

20. A transgenic plant, plant part or plant cell transformed with the nucleic acid construct of claim 1.

21. A method of producing a GH61 polypeptide having cellulolytic enhancing activity, comprising: (a) cultivating the transgenic plant or plant cell of claim 20 under conditions conducive for production of the polypeptide, and optionally (b) recovering the polypeptide.

* * * * *